(12) United States Patent
Kranz

(10) Patent No.: US 11,324,446 B2
(45) Date of Patent: May 10, 2022

(54) ADDITIVE EQUIPMENT TO BASIC EQUIPMENT WITH ADVANTAGE IN FORM OF MULTIMEDIAL, HEALTH, SPORT OR ANOTHER EQUIPMENT CONVENIENT FOR ADDING BY ADDITIVE EQUIPMENT

(71) Applicant: Vladimir Kranz, Prague (CZ)

(72) Inventor: Vladimir Kranz, Prague (CZ)

(73) Assignee: ING. VLADIMIR KRANZ, Prague (CZ)

( * ) Notice: Subject to any disclaimer, the term of this patent is extended or adjusted under 35 U.S.C. 154(b) by 546 days.

(21) Appl. No.: 14/759,208

(22) PCT Filed: Jan. 30, 2014

(86) PCT No.: PCT/CZ2014/000001
§ 371 (c)(1),
(2) Date: Dec. 9, 2015

(87) PCT Pub. No.: WO2014/106501
PCT Pub. Date: Jul. 10, 2014

(65) Prior Publication Data
US 2019/0192075 A1    Jun. 27, 2019

(30) Foreign Application Priority Data

| | | |
|---|---|---|
| Jan. 3, 2013 | (CZ) | 2013-9 |
| Mar. 4, 2013 | (CZ) | 2013-161 |
| May 7, 2013 | (CZ) | 2013-337 |

(51) Int. Cl.
*A61B 5/00* (2006.01)
*A61B 5/024* (2006.01)
(Continued)

(52) U.S. Cl.
CPC .......... *A61B 5/681* (2013.01); *A61B 5/0006* (2013.01); *A61B 5/02438* (2013.01);
(Continued)

(58) Field of Classification Search
CPC ......... A61B 5/681; A61B 5/044; A61B 5/746; A61B 5/04012; A61B 5/0006;
(Continued)

(56) References Cited

U.S. PATENT DOCUMENTS 5,619,775 A * 4/1997 Klinck .................. A61F 5/4407
 24/30.5 R
5,907,354 A * 5/1999 Cama .................. G11B 31/006
 348/231.7

(Continued)

*Primary Examiner* — Catherine M Voorhees

(57) ABSTRACT

An addition of auxiliary functions to the multimedia equipment not included inside. These functions can be function of physiological data processing, extended and/or uninterrupted operations with regard to monitored and processed data. Auxiliary functions are implemented by the auxiliary equipment and circuits solutions physically placed in the original equipment or out of it but mechanically and electrically connected by it, whereas can it formed one compact unit. The parts, which are necessary to be during operation changed to get uninterrupted functions, are user friendly and simply exchangeable from the aspects of users.

9 Claims, 44 Drawing Sheets

(51) Int. Cl.
*H04M 1/21* (2006.01)
*A61B 5/0408* (2006.01)
*A61B 5/04* (2006.01)
*A61B 5/0404* (2006.01)
*A61B 5/044* (2006.01)
*H04M 1/02* (2006.01)
*A61B 5/0245* (2006.01)

(52) U.S. Cl.
CPC ............ *A61B 5/044* (2013.01); *A61B 5/0404* (2013.01); *A61B 5/04012* (2013.01); *A61B 5/04087* (2013.01); *A61B 5/6898* (2013.01); *A61B 5/746* (2013.01); *H04M 1/21* (2013.01); *A61B 5/0245* (2013.01); *A61B 5/6805* (2013.01); *A61B 5/6895* (2013.01); *A61B 2503/10* (2013.01); *A61B 2505/07* (2013.01); *A61B 2560/045* (2013.01); *A61B 2562/221* (2013.01); *A61B 2562/227* (2013.01); *H04M 1/0262* (2013.01)

(58) Field of Classification Search
CPC .............. A61B 5/0404; A61B 5/02438; A61B 5/04087; H04M 1/21
See application file for complete search history.

(56) References Cited

U.S. PATENT DOCUMENTS

| | | | | |
|---|---|---|---|---|
| 7,612,997 | B1* | 11/2009 | Diebel | G06F 1/1632 361/679.41 |
| 8,954,135 | B2* | 2/2015 | Yuen | A61B 5/0205 600/476 |
| 2008/0001735 | A1* | 1/2008 | Tran | G06F 19/3418 340/539.22 |
| 2012/0112903 | A1* | 5/2012 | Kaib | A61N 1/3993 340/539.12 |
| 2012/0116184 | A1* | 5/2012 | Shieh | A61B 5/01 600/301 |
| 2012/0283794 | A1* | 11/2012 | Kaib | A61N 1/3968 607/5 |
| 2013/0106603 | A1* | 5/2013 | Weast | G06F 1/163 340/539.11 |
| 2014/0018034 | A1* | 1/2014 | Lindberg | H04W 4/38 455/405 |
| 2014/0103083 | A1* | 4/2014 | Sitz | F42B 39/08 224/255 |
| 2014/0275888 | A1* | 9/2014 | Wegerich | A61B 5/6831 600/324 |
| 2015/0365756 | A1* | 12/2015 | Merenda | H04R 1/1033 381/375 |

* cited by examiner

| 100 | AUXILIARY DEVICE |
| --- | --- |
| 104a | MODIFIED AUXILIARY DEVICE |
| 199 | AUXILIARY DEVICE |

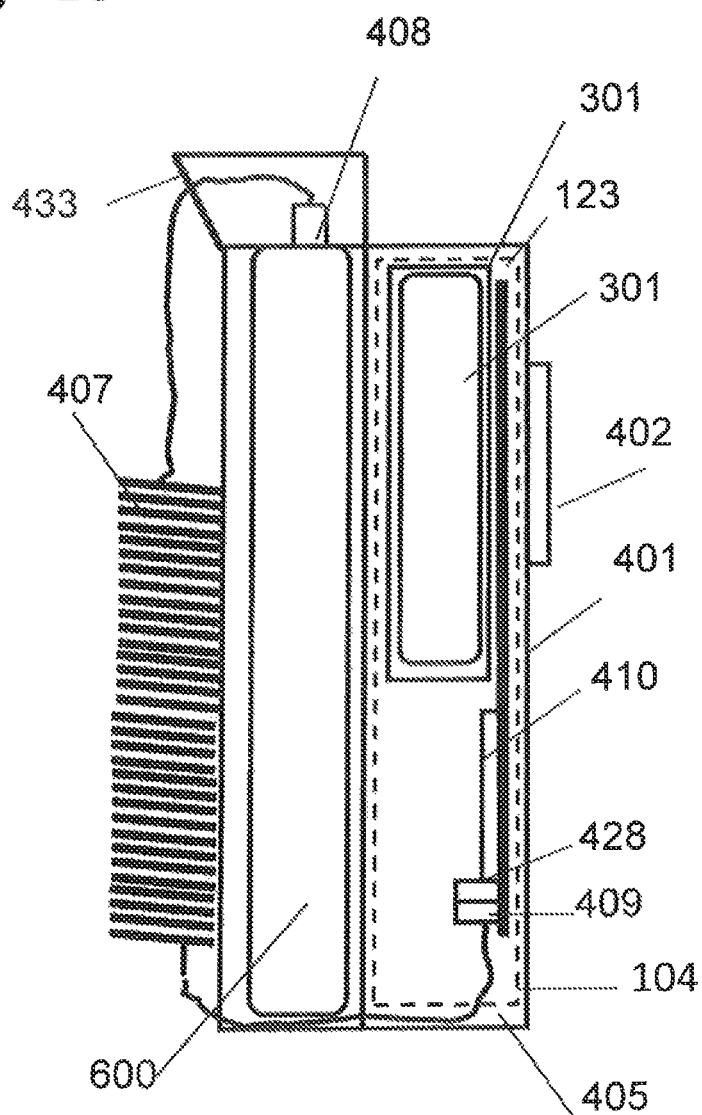

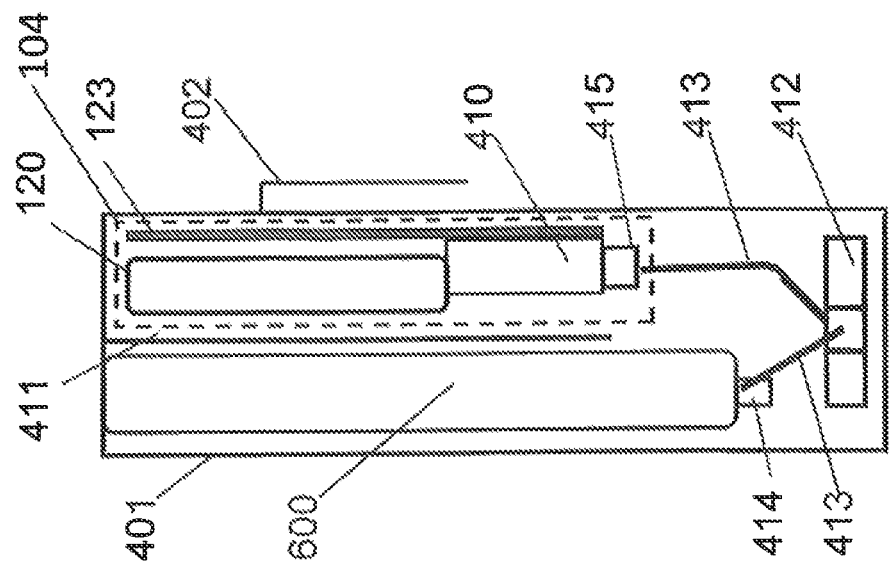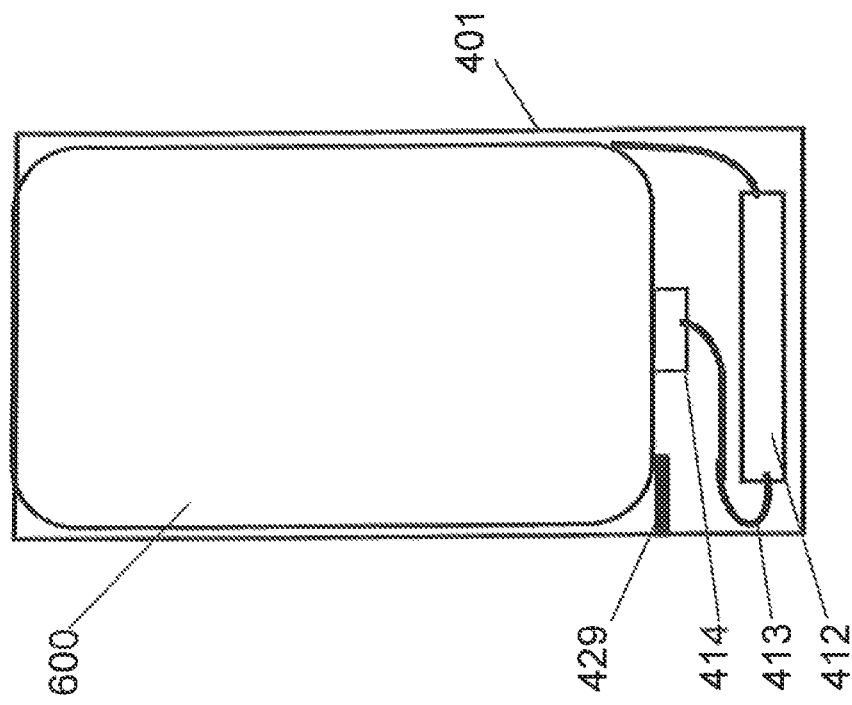

Fig. 19G
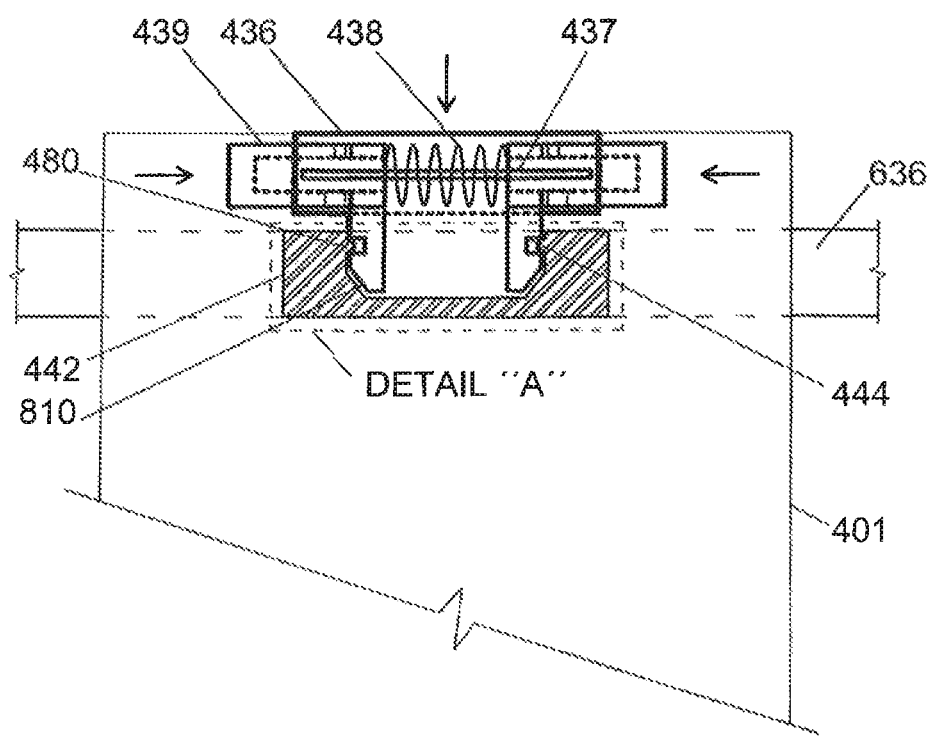
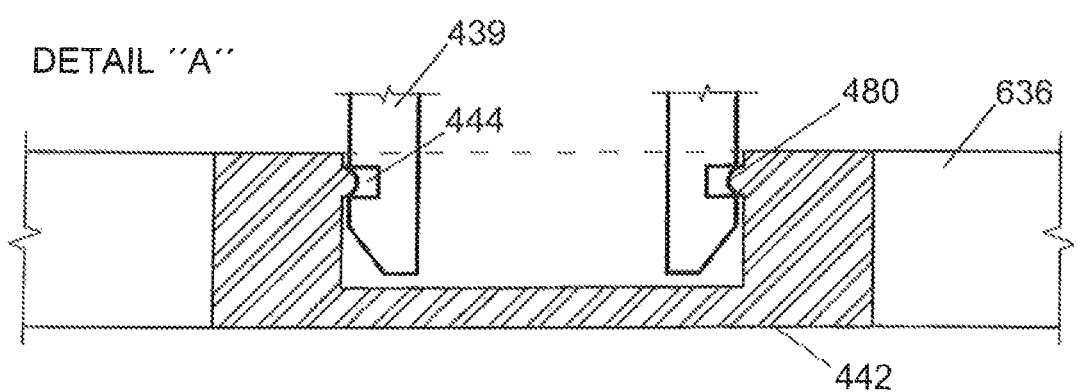

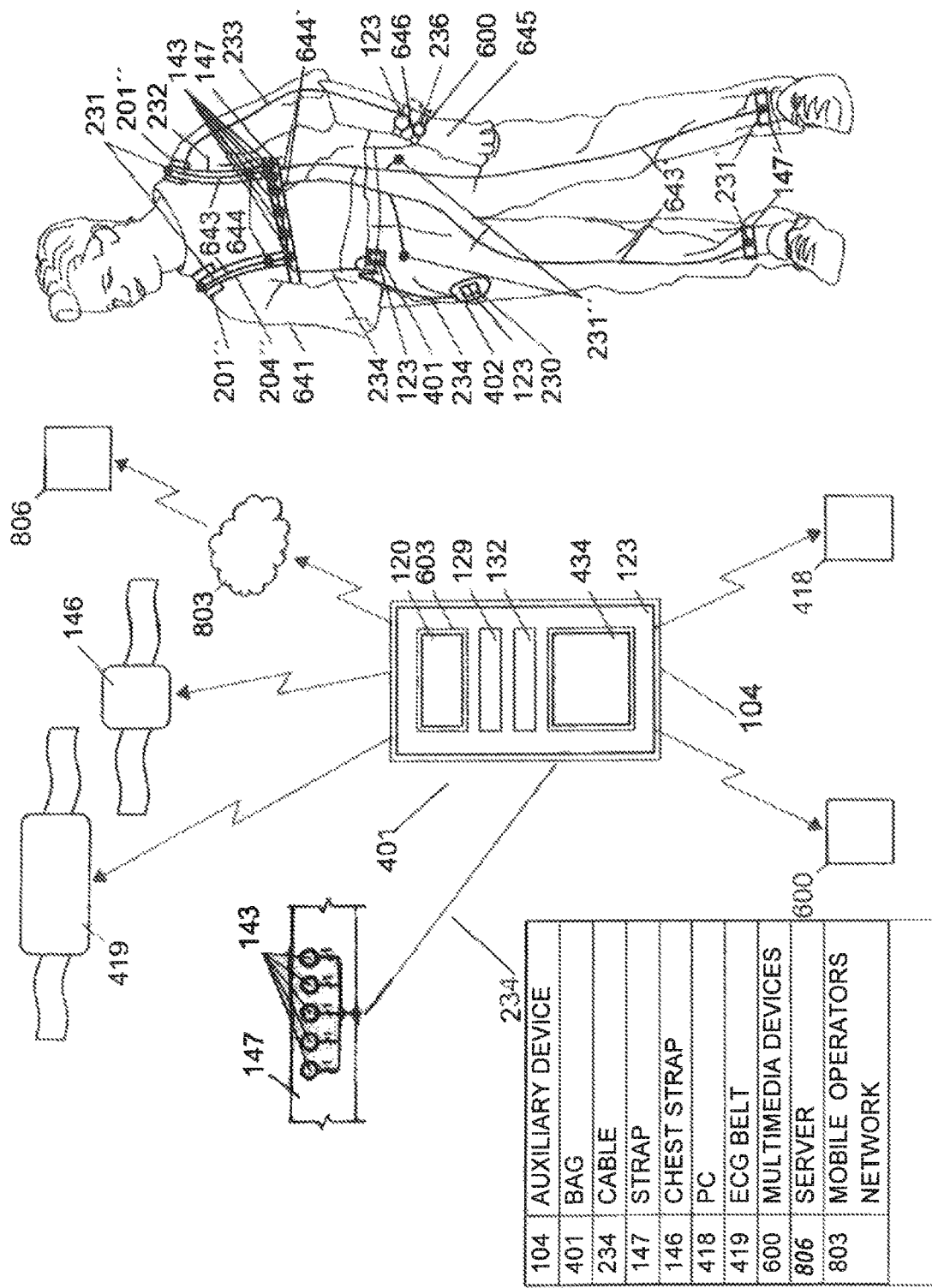

| 100 | AUXILIARY DEVICE |
| 123 | BOARD OF ELECTRONICS |
| 600 | MULTIMEDIA DEVICE |

Fig. 28
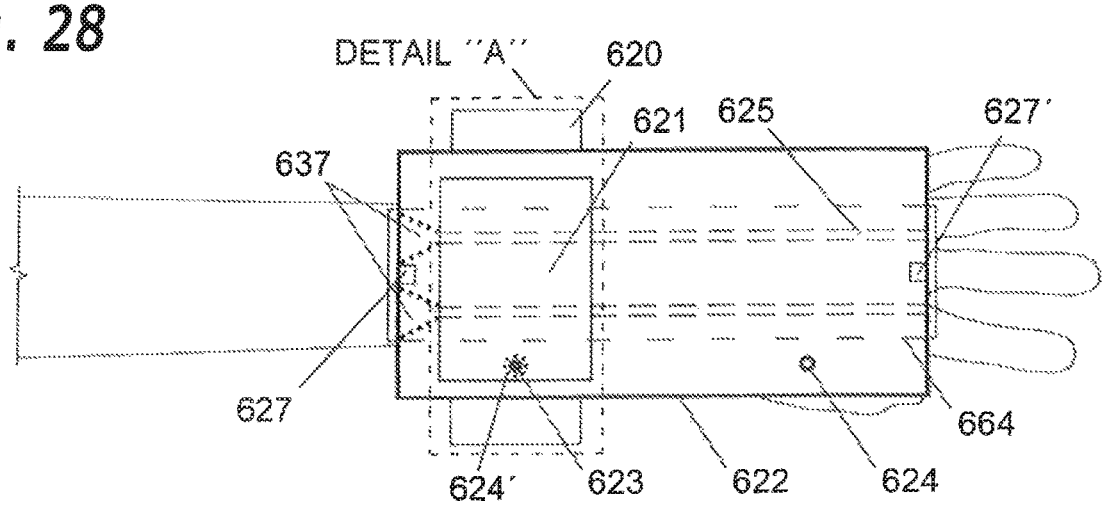
DETAIL "A"
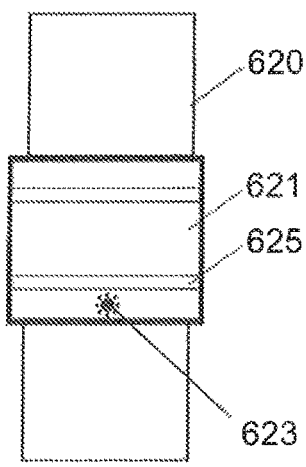
DETAIL "B"
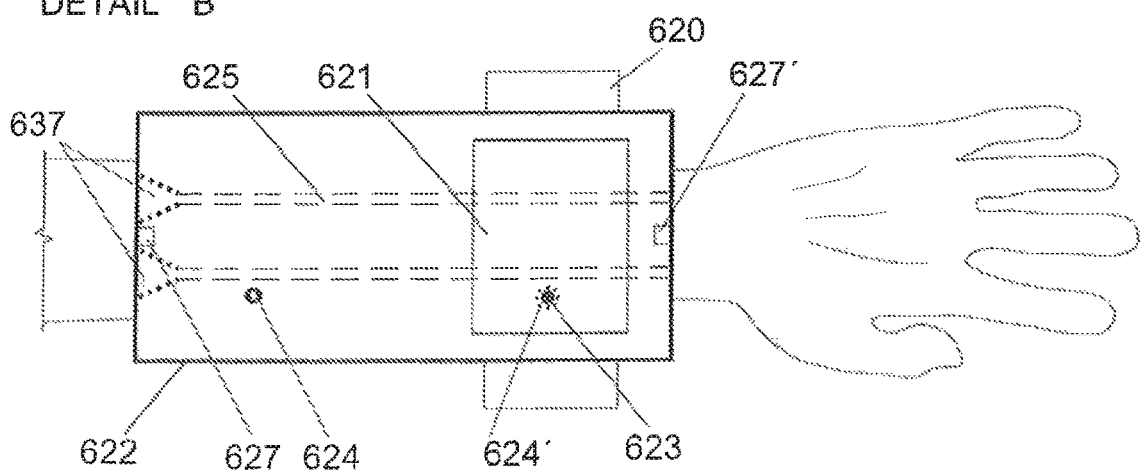

Fig. 29
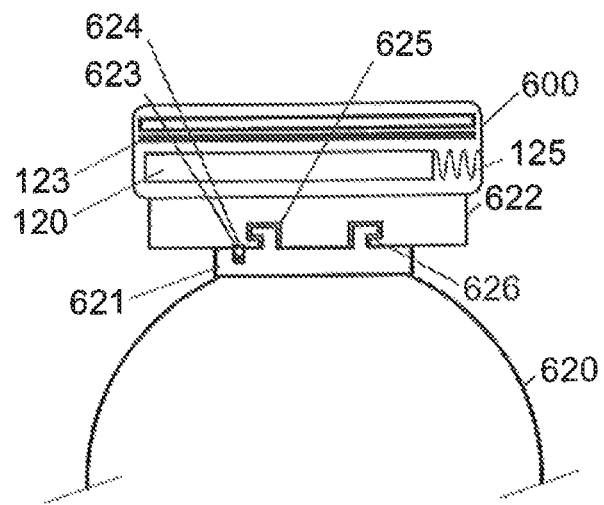
DETAIL 1
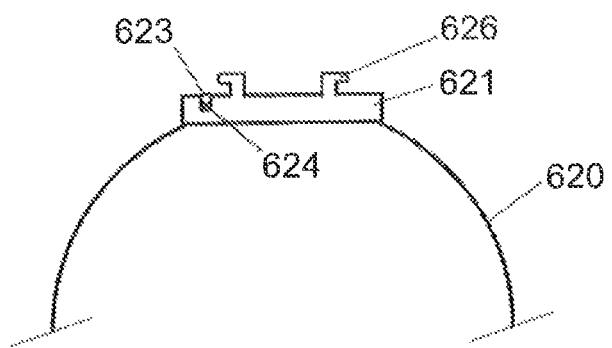

DETAIL 1

ADDITIVE EQUIPMENT TO BASIC EQUIPMENT WITH ADVANTAGE IN FORM OF MULTIMEDIAL, HEALTH, SPORT OR ANOTHER EQUIPMENT CONVENIENT FOR ADDING BY ADDITIVE EQUIPMENT

BACKGROUND OF THE INVENTION

Field of the Invention

The invention concerns the functions extension of multimedia equipment by auxiliary devices situated on them or separately. Solutions are elaborated also for sensing data of heart rate and transferring it into portable ECG or into a small size device for imaging of data or curve of heart rate, possibly on cellular phone, placed on detachably on bracelet with respect to deployment of electrodes and cables on the body of checked person so as they do not bother to ordinary motion and activity. It should be also easy for installation, bearable from aesthetic point of view and bearable and suitable for non-interrupted sensing for unlimited time.

Description of Related Art

Contemporary auxiliary equipment do not allow uninterrupted operation of multimedia devices and theirs auxiliary equipment, which are needed for monitoring of function, for instance physiological. ECG signals or displaying of heart rate are sensed by means of chest strap electrodes or single electrodes glued to skin or fastened by clips to limbs. The last named are not suitable for mobile use. Using of chest strap in mobile operation is uncomfortable to wear, and not aesthetic, because for installation there is necessary to remove clothing. Shifting of electrodes on skin causes jamming signals. Glued body contacts are very unpleasant at removing and the skin can be irritated. Contact cables for ECG are deployed in complicated way and are unarranged on the body, which is not aesthetic. The purpose of this invention is to find better deployment of electrodes so as the monitored person could watch heart signals uninterruptedly for long time.

Except inventions PV 2010-629, PV 2011-446 and PV 2011-581, the contemporary level of technology does not enable live monitoring of the course of hearth rate, arrhythmia, ECG and other biomedicine data in values, curves and graphs, especially at the same time. It does not enable such monitoring on units placed on wrist where it is immediate view. Units are not removable. They do not enable battery exchange without interrupting the operation. They do not enable data transmission at the same time to more units with cooperating software, which would be able to process and display the measured values in the same way. The purpose of this invention is to eliminate all these drawbacks and improve solution in patents PV 2010-629, PV 2011-446 and PV 2011-581.

BRIEF SUMMARY OF THE INVENTION

The drawback is removed by an auxiliary device to a multimedia device, where the multimedia device is created preferably by cellular phone or multimedia pocket computer or similar multimedia device, where multimedia device enables further described basic functions or some of them such as are voice and/or data communication on telephone or other wireless network, multimedia playback, taking snaps, or video recording, TV reception or/and radio broadcast, GPS determination, and contains basic units and/or parts such as control elements comprising with advantage push buttons or/and keyboard, or/and touch display, basic microprocessor unit, basic accumulator and other basic units allowing functions mentioned above, where auxiliary device contains at least one block composed of auxiliary mechanical, electric and electronic modules and units and/or parts preferably of control elements and storing mechanism of accumulator, which are mechanically, electrically and electronically connected with multimedia device, which extends basic functions of multimedia device by auxiliary functions which the auxiliary device, containing modules, units or parts enables, where multimedia device is preferably fully functional with basic functions for which it was designed and constructed even without connected auxiliary device.

In detachable and paired embodiment of auxiliary device connected to multimedia device from line-production, which means not factory adapted for connection with auxiliary device, is the auxiliary device detachably attached mechanically to the surface of multimedia device not factory adapted for connection with auxiliary device replacing it by the back cover situated currently at the opposite site of display or keyboard, serving for covering of parts such are, accumulator and/or SIM card and/or other parts for exchange of which the cover is removed, whereas the fastening elements are paired with fastening elements of cover of multimedia device. In general-purpose version the auxiliary device is removable connected to the surface of multimedia equipment non-adapted from the factory for connecting auxiliary device with fixing elements with advantage with a clip, Velcro, screws or other elements.

Another possibility of connecting the general purpose version of auxiliary device is to fix it to the cover of multimedia equipment non adapted for fixing of auxiliary device with which is removed and replaced with a spare cover of multimedia equipment, or with another installed device, with advantage with other functions than removable auxiliary device, where the fixing elements are with advantage formed by depressions, clips, joining layers, Velcro, glue layer, or fixing by glue, screws, or other suitable manner or by combination of them. Advantage of fixing of auxiliary device to the cover of multimedia equipment is the availability of covers, which are produced as spare parts, and fixing auxiliary device on them enables easy possibility of connection of one or more types of auxiliary devices to multimedia equipment by simply exchange of basic cover.

A great advantage of multi-purpose auxiliary device is the possibility of its connection to any multimedia device from line production, which does not need to be adapted for using auxiliary device. Preferably with mechanical connection is connected also electronically by plugging connector into connector of multimedia device, or can be connected subsequently. In such a case. A "U" connector can connect multimedia and auxiliary devices. For multi-purpose version can be preferably used two connectors; one for multimedia device, second for auxiliary device joined with electric cable in order to avoid placing connector at the auxiliary device accordingly to connector position at the multimedia device. The particular auxiliary devices can be equipped with various functions and can be preferably placed accordingly to needs of various levels of extension functions of multimedia devices. The auxiliary devices are preferably placed on multimedia devices from line-production, which means that fixing elements are only for the back cover and not for auxiliary device. All electric and electronic units and parts for auxiliary functions are preferably situated in auxiliary device. This advantage is put into effect particularly when one acquires multimedia device where auxiliary functions are not needed in which manner it is cheaper in comparison when a part of units and parts for function extension would be installed in this multimedia device. An advantage of placing the auxiliary device on a line-produced multi-media device, where all electronics is contained in auxiliary device, which can bring down the price for acquiring the multimedia device in case when the auxiliary device is not acquired in the same time and can be bought anytime later. It is favorable in comparison with devices, which enable to install additional devices, but units for them are partly or fully placed in multimedia devices, so that when one does nor acquire auxiliary device, these units increase the price of multimedia device. This is also advantageous in comparison with multimedia devices which have additional equipment designed as permanent installation, where without it the multimedia device is not fully functional, or in case if not used would appear as incomplete or incompactly. In case when additional device were not used, the price of multimedia device uselessly would increase, because without it the multimedia device is incomplete.

Fixing elements made preferably for fixing the cover on multimedia device are fully or partly used for detachable fixing of auxiliary device, which is equipped with counterparts again fixing points on multimedia devices. Original fixing elements on line produced multimedia devices are advantageously used, or are adapted afterwards after they are produced, which enables cheap line-production of multimedia devices regardless if it will be used for connecting to auxiliary device which enables its line production in big series which make is cheaper in comparison with multimedia devices for which the connection with the auxiliary devices would be proposed in other way than by replacing the back cover where the fixing elements would be solved in different way already in the factory, which increases the price and is not produced for broad use and is suitable for applications with auxiliary devices. Another design of detachable auxiliary device is installation at factory adapted multimedia device for a specific auxiliary device, which forms common equipment, where is supposed that auxiliary device will be used with this multimedia device, or at least prevailing time and will be also commonly sold. In this case the advantage of savings will be lost in comparison with connection of auxiliary device with multimedia device from line production without adjustment for auxiliary device which can be named as optional equipment, on the other hand many benefits will be preserved, especially the exchange of accumulator without removing the auxiliary device and further extension of functions of multimedia device. In principle the cooperation and benefits of specific auxiliary device and putting blocks on, remain in principle the same as at paired or multi-purpose auxiliary device during the production. If the auxiliary device is not connected, the uncovered parts of multimedia device can be preferably covered by especially produced cover. Since it is taken into account with contemporary usage of auxiliary and multimedia devices, there a possibility exists to place a part or all electronic needed for proper operation in multimedia device. This is an advantage to use more auxiliary devices with different auxiliary functions for extension of multimedia device according to needs. Then can be saved units and parts, which are common for more auxiliary devices, which need not be placed in all auxiliary devices. It is preferably possible at removable auxiliary device to use additional controlling elements at auxiliary device, where statuses are detected by auxiliary microprocessor and transmitted to basic microprocessor unit. It can be preferably used the pushbutton for emergency call, which is mechanical, sufficiently large, highly visible, placed on auxiliary device, so that the endangered person can immediately send an emergency call without complicated manipulation on display or keyboard of multimedia device comprising a cellular phone, where especially the touch screen need complicate manipulation for displaying the adequate push button, where push buttons are small and situated very dense. Respectively also reset button can be placed on the auxiliary device. In integrated version is the auxiliary device built into multimedia device without possibility of easy disconnection. The advantage of lowering the price of multimedia device is lost in case that all or some auxiliary modules, units or parts are at its acquisition not needed, because they are already built in a compact multimedia device in some certain version and after the product is finished, they cannot be changed by attaching of various auxiliary devices, but the advantage of extended functions in compact multimedia devices enabled by auxiliary modules, units and/or parts remains in the contrary with functions enabled by basic units in current multimedia devices. The issue is the extension of basic accumulator capacity by an auxiliary accumulator easy exchangeable during operation of multimedia device without removing the back cover of the multimedia device, which is enabled by storing mechanism of accumulator, which is in multimedia device firmly installed. The issue is also putting two or more microprocessor units, communication block, and "front end" unit for processing ECG curve and other auxiliary units and parts, as described at detachable auxiliary device. At next version is an auxiliary device detachable from compact multimedia device, where differently equipped auxiliary devices can be changed. Disassembling is more complicated then at detachable auxiliary device, but there is an advantage of making use of differently equipped auxiliary device according to demand and so lower the price because there are acquired only relevantly equipped auxiliary device, or nothing. Detachable auxiliary device is placed on printed circuit board and id removable separately or together with the board of basic modules, units and parts of compact multimedia devices. The detachable auxiliary device is preferably made in shape of a cassette, which can be inserted into the body of multimedia device.

Advantage of this solution is in easy exchange of removable auxiliary device for another, differently equipped. Removed can be all or a part of auxiliary device. At all types of compact multimedia devices is preferably used storing mechanism of auxiliary accumulator for easy exchange of discharged accumulator for charged one during uninterrupted operation of compact multimedia device for charging the basic accumulator without opening the back cover. At line-produced multimedia devices, the auxiliary devices enable add other functions, such as increasing capacity of basic accumulator by capacity of auxiliary accumulator placed in auxiliary device. In this function the auxiliary accumulator charges accumulator of multimedia device through an electronic unit made preferably by voltage converter or regulator by means of electric connection the auxiliary device with multimedia device. The auxiliary device preferably enables easy exchange of auxiliary accumulator without removing auxiliary device, by means of storing mechanism of accumulator comprising small door or a small lever, which simultaneously locks accumulator at the moment of inserting it, or by mechanism reacting to squeeze when inserted accumulator is pressed and by doing this, it is released and ejected and at new inserting is locked by a latch. This advantage is evident in contrary to the standard multimedia device without auxiliary device when exchange of accumulator is complicated and needs to remove the cover, which takes longer time. The basic accumulator preferably supplies the multimedia device during the replacement of auxiliary accumulator so that the replacement is realized without the interruption of operation of multimedia device. The easy replacement of auxiliary accumulator is further supported by the possibility of charging several auxiliary accumulators at the same time, which after charging can be carry in the pocket or in a case and be disposal for replacement of auxiliary accumulator in the auxiliary device connected to multimedia device during operation, which provides an advantage of any prolongation of uninterrupted operation. This means that in case of discharge of the basic accumulator, here is not necessary to search for source of charging or uneasy replace the basic accumulator with removing the back cover of the multimedia device and to interrupt the operation, or to replace the auxiliary device. This means savings due to the fact that in case of replacing the entire auxiliary equipment, for sake of replacing the discharged accumulator, the other auxiliary equipment must be kept in reserve for this purpose, but the auxiliary equipment is more expensive and larger than the accumulator also due to the fact that it also contains the electronics for charging, or other additional functions. The costs reducing solution is to keep in reserve and exchange only the auxiliary accumulators provided by the solution of the present invention. Placing the charging electronics in the multimedia device, as applicable in the current state of technology, increases the costs of multimedia device, which becomes evident, when the auxiliary equipment is not purchased for the multimedia device. The solution specified in this invention, where all the electronics ensuring the functions of auxiliary equipment is located in the auxiliary device, thus representing the savings. Moreover, the solution of replacing the accumulator from the storing mechanism, preferably by small door, induces other advantage that the serially produced auxiliary accumulators may be used so as they can be utilized in their unchanged form of the specified utilization, thereby reducing significantly the purchase price of the accumulator compared to the price of accumulator, which would have to be manufactured specifically for this purpose, and so in much smaller series. In the auxiliary equipment, preferably beyond the accumulator, other units and parts extending the original functions of the massively produced multimedia device can be placed. The utilization of one or more auxiliary microprocessor units, which preferably operates with different operating systems than the basic microprocessor unit of multimedia device, thus allowing not only to extend the performance of basic microprocessor unit, but also working with a wider range of operating systems, programs and applications, induces a particular advantage. This allows, for example, in relation to multimedia device comprised of the cellular phone with the Symbian operation system in the basic microprocessor unit to use the Android operation system in the additional microprocessor unit of the additional device, hence to enable the operation or programs and applications in both OSs where by means of communication via connector interconnecting the multimedia device and the auxiliary equipment, preferably through a USB port, or multi-pin connector, or by means of interconnecting conductors in the auxiliary device integrated in the multimedia device. So it is possible preferably to control the auxiliary microprocessor from the multimedia device by use of control elements in the multimedia device and also displaying requested data from auxiliary microprocessor unit. Preferably it is possible to use even more microprocessor units and so extend the number of operational systems. In auxiliary device there is preferably situated a communication block, which extends communication functions of multimedia device. So, it can be with advantage used receiver 5.5 kHz for reception pulses of heart beat or other signals from a chest strap working in low frequency band 5.5 kHz, which has advantage in low power consumption in both, reception and transmission sides. For instance, the battery in chest strap for measuring heart rate and working on 5.5 kHz frequency has the live-time one year, which is the same at the reception end, whereas chest straps for measuring heart rate equipped with system Bluetooth work with the same battery only a few hours. The low energy consumption is resulting also at supplying receiver or transmitter 5.5 kHz in auxiliary device. Another advantage using transmission 5.5 kHz for hart rate data is that this signal can be received simultaneously by more devices which enables contemporary displaying the heart rate and its graphical displaying on more devices. This is advantageous especially at using wristwatches for emergency displaying of heart rate and other functions derived of it with displaying of the same or adapted data on multimedia device, which is usually larger then wristwatch display, so it is operatively possible to watch heart rate and data derived of it on display at wristwatches and in the same time on multimedia device advantageously made by a cellular phone, which can be stored in a pocket or a small bag. The cellular phone can be taken out and switched on for current watching only in needs of more detailed information in case when data is out of limit and display of wrist watches does not provide as full information such as provides multimedia device with larger display. Extension of information can be used using further communication working preferably with further units using ANT, WIFI, Further Blue Tooth and other units using further communication systems and media. An auxiliary and basic microprocessor cooperate through data connection by means of connector connecting multimedia device with auxiliary device preferably through USB or multipin connectors or with wires at auxiliary device integrated in multimedia device, which enables to use further functions of auxiliary device. One of further functions of microprocessor unit can be preferably ECG processing, where body signals sensed by electrodes and preprocessed in "front-end" unit situated preferably in chest strap are transferred by means of Bluetooth or similar communication protocol into communication block in auxiliary device, where this signal is processed in auxiliary microprocessor unit and send through data connection into basic microprocessor unit for further processing for displaying ECG curve on display of multimedia device, where control of display and choice of other functions can be done from display or keyboard of multimedia device. This enables with advantage watching the ECG curves, other values and further evaluation. It is an advantage, that received and processed and displayed ECG is mobile and the monitored person can carry it in a small bag or pocket with him/here and find out his/her state of health, especially when warning signal sounds in case when heart pulse or ECG or other monitored health functions, preferably detected and transferred by chest strap exceed allowed limits. Similarly is ECG processed by auxiliary device, where electrodes are connected with a cable with auxiliary device, which has an advantage in higher reliability and elimination of jamming of transfer through BT, where ECG can be processed in auxiliary device and control and display on multimedia device. In this case is "front-end" in auxiliary device. ECG and other health or other data is preferably transferred from auxiliary or multimedia device to remote server placed preferably in surveillance center or other data storage, where from it is possible data display on a PC locally or by means of data network remotely.

The auxiliary device for the basic device, formed preferably by multimedia, health, sport or other one is preferably placed in a small bag, which can be fastened at waist, belt, in pocket or can be hanged on neck. Multimedia device can be embedded in the small bag, where it can be connected by means with multi-wire cable or connector or Bluetooth or other wireless medium. Auxiliary device embedded in the small bag contains auxiliary mechanical, electric or electronic modules, units or parts with controlling elements and/or or storing mechanism for accumulator which extends basic functions of multimedia device as described at auxiliary device fastened to multimedia device for instance in similar way as auxiliary accumulator placed in the small bag which charges the basic accumulator placed in multimedia device. Auxiliary accumulator is placed in storing mechanism from where it is easy replaceable during uninterrupted operation of multimedia device, which is backed-up by basic accumulator, which is charged by the auxiliary accumulator. In electronic part of auxiliary device situated in the small bag is placed one or more microprocessor units, which work on one or more operating systems, differently from the system of basic microprocessor unit in multimedia auxiliary device. They communicate with multimedia device, which with they are connected as mentioned above, and mediate preferably transfer of status of "panic button" and "reset button" and also with communication units 5.5 kHz for reception of heart rate pulses and a communication block with different communication media, preferably Bluetooth, ANT and other. The button "Panic" and "Reset" on the auxiliary device are preferably mechanic and of bigger size, i.e. easy accessible and reliable in comparison with keyboard formed by touch display, which is advantage in cause of emergency call. After pushing "Panic" button, a warning signal lasting a few second is triggered. If this signal is not cancelled during time when warning signal sounds by the "Reset" button, the system sends emergency call to preprogrammed phone numbers or surveillance center. To the USB connector for interconnection the small bag with the multimedia device by a cable, preferably another USB connector is fixed for contemporary charging the basic accumulator of the cellular phone. It allows also connection with a computer.

The auxiliary device in the small bag enables connection of an ECG in the chest strap wirelessly preferably by Bluetooth, whereas the so-called "front end" for ECG is preferably placed in the chest strap with the control unit with electrodes. Signal ECG is further processed in microprocessor unit of auxiliary device located in the small bag. The front end of ECG can be placed preferably in chest strap which is saving energy and enables longer accumulator operation. The data transfer from ECG or heart beat pulses or other medical or other data can be preferably realized by means of mobile operator network from the multimedia device or auxiliary device located in the small bag, or from chest strap with help of a unit for data transfer into mobile operator network by means of SIM card in communication module. On the body are preferably deployed only ECG electrodes, which are connected by cables with auxiliary device in small bag where is located a complete electronic device for heart pulse or ECG evaluation. The shape of ECG curve is displayed together with heart rate, which allows more detailed observing of regularity or for longer time, for instance 30 sec, where for ECG is displayed smaller time period, for instance 5 sec in order to enable distinguishing the ECG shape. Displaying can be made on multimedia device or local computer, or remote computer by means of data network as live data from current measurement, or recorded data from memory of auxiliary device located in the small bag, or from server or computer.

Also microprocessor, or microprocessors located in microprocessor unit work preferably on diverse systems, differing from protocol in multimedia device, which offers the advantage to work with more databases. The printed circuit board with microprocessor units or communication modules or other units is preferably removable, which enables to use another printed circuit board according to the needs or in case of failure. Multifunction multimedia device is inserted into the small bag which can be preferably equipped with removable inlet attachment with extending pitch for easy inserting, which is favorable especially in case when the small bag is placed in a pocket where is a clip fastening it. In the multimedia device, it is preferably put a mechanical element with contacts which freely and without resistance fit into counterparts located in the small bag. This allows easy connection the multimedia device into the small bag.

Location of 5.5 kHz receiver in the small bag enables contemporary receiving heart rate in wristwatch working on this frequency and receiving this signal preferably from the chest strap of multimedia device, which is connected to the small bag by elongated cable or wirelessly.

At the same time is enabled simultaneously reception of both heart rate and signal ECG by cellular phone located on a bracelet, which is joined by means of Bluetooth placed in the small bag on multimedia device. Signal for cellular phone on the bracelet is possible to send preferably from multimedia by means of Bluetooth. An elongated cable for connection of multimedia with the small bag can be composed of a twisted cord, or cable on a spinning reel located out or inside of the small bag.

It is possible to use preferably the display of multifunction device for displaying data, curves and pictures produced by auxiliary device in the small bag and use control elements in multimedia device for control microprocessor units, preferably ECG or heart rate monitor placed in auxiliary device in the small bag. Small bag contains preferably a display, located preferably on a printed circuit board where microprocessor units, communication modules and control elements are placed. It is also pull it out from the small bag for displaying data or pictures, or display can be placed on a separate removable board. Display is preferable located on the small bag and is visible even unless is removed from the small bag. In version with touch display it is possible to control from the display also units in the small bag as well as multimedia device, which is of course possible preferably also by mechanical push button "PANIC" and "RESET" which are placer on the small bag so as they are accessible without pulling out display or electronic units.

Auxiliary device fastened to the multimedia device or inserted in it as mentioned above, or placed in the small bag, can be preferably placed in multimedia device composed of a cellular phone, or by a healthy device located in the bracelet, where all described functions are applied also in this case. Connection with the basic device is preferably realized through connector USB on the bracelet, or on other part of the cellular phone. The auxiliary device is fixed on the bracelet from the body or to the body below the cellular phone. In case off the body is from the connector on the bracelet conduced to the case of auxiliary device. In version "at the body" is preferably lead from the connector placed "off the body" by a cable into the case of auxiliary device where it is situated. In the version "below cellular phone" is preferably lead by a cable from the connector as described. In adapted multimedia device is the cable installed into multimedia device or bracelet, so it is not visible. The case of auxiliary device preferably contains storing mechanism of auxiliary accumulator which is easily removable through small door without interrupting the operation. The auxiliary accumulator charges preferably the basic accumulator. On printed circuit board blocks and units of electronic devices and microprocessor and communication are located. All is located in mentioned case. All of them are with advantage replaceable so it is possible blocks equipped in accordance with needs. If USB connector is placed in other part than on the bracelet, the basic device is connected with an appropriate cable to the auxiliary device. On the top of the case for auxiliary device in version at the body or below hand which is placed at the bottom part of the bracelet, preferably a display is placed, which can display data processed by one or more processor units of auxiliary device or in the basic device. Preferably one or more microprocessor units and also other units can be controlled by cellular phone or they have their own control elements. This is advantageous at "PANIC" a d "RESET" buttons, which are preferably located on the case of the auxiliary device and so they can be of bigger size and distinctly separated from other control elements. This prevent erroneous call for help or reset in case if "PANIC" was pushed and is evaluated that emergency signal should not be sent off. The multimedia device in the bracelet is preferably placed on a sliding mechanism which is preferably adapted for easy removal of multimedia device, which enables the multimedia device slide out to hand when is necessary to watch display or to slide it back to forearm in order to hide it below the shirt if it is not necessary to watch the display. Multimedia device preferably constituted by a cellular phone on a bracelet can be used for evaluation of ECG which is preferably placed on chest strap likewise described at auxiliary device placed in small bag. Connection is preferably ensured by Bluetooth transmitted from chest strap where ECG is located including front end or multimedia is on the bracelet connected with a connector by cable. In this case front end can be located at microprocessor, located in a cellular phone on a bracelet and detectors on the body connected by a cable. In case of wire connection it is possible to place the complete control unit of ECG into cellular phone at the bracelet and on the body there are only electrodes partly on chest strap. ECG can be placed in a special unit preferably at a bracelet near the cellular phone at the bracelet whereas with electrodes is connected by cable or Bluetooth. Scanning of hearth pulses is done by five electrode system, where 3 electrodes are preferably situated on the chest strap below chest nipple and 2 further electrodes are on area of shoulder sockets preferably fastened on braces where are connected with the chest strap by a cable covered by aesthetic appearance by braces. This version offers a three lead ECG record. For one lead ECG record can be used 2 electrodes located on the chest strap below chest nipple where can be added in the middle third electrode for zero reference voltage. For highlighting display of wave P is preferably placed another further electrode in shoulder socket connected by a cable with a connector with chest strap, which can be disconnected in case if wave P is not needed. In both cases one and three lead is cable lead to the bracelet or ECG preferably from chest strap where are connected all electrodes through a cable laid around the neck and further on arm. In this way it is achieved that after putting on the shirt or blouse the chest strap as well as electrodes and all camel network is not visible from outside.

For quality measuring it is necessary electrodes with contacts provide with a thin layer of conducting gel. For a chest strap mentioned above there are designed electrodes with a popper system fastening which are in shipping cartridges in which they are fastened to the strap by clicking on and then when the strap is in proper position around the body the cartridge is removed which reveals the contact surface provided with a layer of contact gel. Subsequently the strap pushes into working position on the body of monitored person. Alternatively can be used electrodes glued on conducting surface of chest strap, whereas the shape of gluing part of the contact ensures, that at increasing pressure the gel leaks through the middle part and makes contact with the body of monitored person.

The storing mechanism of the accumulator enables easy exchange of accumulator for another charged without opening and removing the back cover of multimedia or health device or exchange of all auxiliary device or its part preferably without interruption the operation. This is enabled by means of a module of charging and supplying with which it preferably comprises a block of accumulator filled in by a further auxiliary device. Fastening mechanism of accumulator or block of accumulator is replaceable so as they can be used in different, preferably more modern models of multimedia or health or auxiliary devices and saves expenses for their acquisition by using them from older models. The exchange is easy to do by inserting, screwing, clicking on and inserting contemporary into counterpart connector. The fastening mechanism of accumulator is preferably based on principle of small doors which ensures by clicking them, or on principle of moving away a latch ensuring the accumulator, or by automatic ensuring accumulator at inserting and releasing by repeatedly pushing, where the side of accumulator makes the wall which covers the aperture for inserting accumulator in case when there are not used doors.

Hinges of doors are made of metal or plastic and are preferably equipped by pivot hinges or hinges are preferably made of a flexible resilient material preferably plastic which is used for the rest and in place of hinges is made thinner. As an electrode of ECG or pulse monitor it can serve preferably a contact with conducting elastic material, preferably conducting gel i.e. a gel electrode. Electrode is fastened on a pressure chest or leg element, braces or pressure clothing or harness. Electrode is removable and exchangeable for a new one by means of its fixing mechanism, which can be preferably based on a principle of press stud or by gluing by means of a foil or by another suitable manner. Advantage of placing the electrode by means of fixing mechanism on pressing element is that the electrode is not glued on skin which can produce possible allergic reactions and painful removing, but it is fastened on pressing belt, preferably elastic, which can press the electrode to the skin by suited preset pressure for reliable contact which improves the conductivity or adherence of gel material.

Storing mechanism for auxiliary parts enables to use the same part on more models, preferably new models and so save expenses for its acquisition. Removable fastening is ensured by inserting, snapping, screwing or gluing or by another way. The auxiliary device is mounted on multimedia device by means of fastening mechanism of the auxiliary device. This enables fasten the auxiliary device on different types of multimedia devices, preferably also new ones, which brings the advantage that also for new types can be used the present devices and so save expenses for acquisition in case of changing the type.

A next example of fastening mechanism is fixing of auxiliary device by screws or gluing on the back cover of multimedia device, whereas the leveling the bumpiness out of the cover can be carried out by a flexible underlayment fixed by screws or glued. The auxiliary device is preferably smaller in terms of area then multimedia device, which enables to use a great spectrum of multimedia devices. Electric interconnection is preferably made by means of electric cable on one side with a USB connector which is inserted into connector of multimedia device where it is inside covered a reserve of electric cable for adaptation for different types of multimedia devices.

The present chest straps for sensing heart rate or ECG have deficiency in jamming caused by motion of the body, when a part of the strap with electrodes surrounding the body moves which changes the contact. This drawback can be eliminated a sliding chest strap consisting preferably of parts with sensing electrodes with fixative part which surrounds chest and freely slides on fixative part with which is not mechanically joint and by body motion is not shifted on skin. For better slippage there is used sliding material, preferably on both parts of the strap. Principle of sliding strap is used preferably also with braces which are connected with chest strap and by its elasticity press the sensing part with electrodes located in area of shoulders in order to comprise together with electrodes on chest strap a system of electrodes for 3 lead ECG and further 2 electrodes and 2 additional electrodes on leg strap they form 12 lead ECG. Electrodes are connected by electric cable with a board of electronics which serves for processing heart signals for ECG or/and a curve of heart rate, which is located preferably in the small bag near waist or in the pocket or on wrist where electric cable is preferably laid through the sleeve and placed preferably on the bracelet with sliding mechanism where from which van be removed for easy manipulation. Connecting with the board of electronics enables elongated twisted cord or spinning reel. Connection with multimedia device, PC and servers is ensured wirelessly.

BRIEF DESCRIPTION OF THE SEVERAL VIEWS OF THE DRAWINGS

FIG. 15 depicts an option of leading and placing the twisted cord outside the bag.

FIG. 18A depicts the configuration of the bag using the self-acting reel and the cord with the connector to enable the link of the multimedia device to the electronics module of the bag.

FIG. 18B depicts side view of the bag shown on FIG. 18A

FIG. 19G depicts the pin/unpin procedure of the bag by mean of fixture mechanism.

FIG. 19I The circuit board, equipped with the display, placed in the bag.

FIG. 19J depicts an example of distribution of electrodes of the three-lead ECG sensing, i.e. placing the ECG electrodes on the chest belt with the shoulder straps with the electrodes.

FIG. 28 depicts the bracelet with the eject mechanism for the ejecting attachment of multimedia device.

FIG. 29 depicts the side view of the ejecting mechanism with the placement of the multimedia device made visible.

FIG. 39 depicts the portion of the pushing element to enable that the electrodes are pulled on.

DETAILED DESCRIPTION OF THE INVENTION

Figure 1:
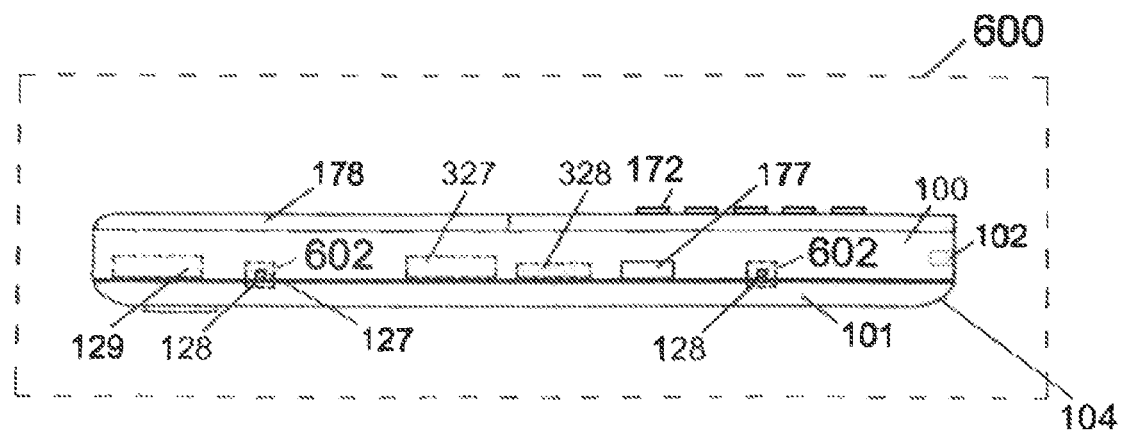
FIG. 1 is example of connection of an auxiliary device with multimedia device.

FIG. 1 is example of connection of an auxiliary device 104 with multimedia device 600. The multimedia device 600 formed by a cellular phone 100 from line production is not adapted for connecting of the auxiliary device 100. The auxiliary device 100 according to advantageous embodiment of the invention is placed in removable cover 101 and the connecting of the multimedia device 600 with the auxiliary device 100 is done by fastening elements 602 made by hitches 128 of cover fitting into counterparts 127 made by depressions on cellular phone 100 where cover is situated at the adverse side of display 178 and keyboard 172 covering SIM card 177 and accumulator 129 placed inside of the cellular phone. On the cellular phone 100 is situated a connector 102 for connecting USB cable; inside the cellular phone 100 is accumulator 129, microprocessor unit 327 and basic communication block 328. The multimedia equipment 600 without the auxiliary device 104 can be made into a multimedia pocket computer or similar multimedia equipment that contains functions such as mobile communication via the internet, communication via a mobile phone network or other data communication media, multimedia playback, photo-camera, TV camera, GPS detection with virtual keyboard equipped with keyboard and display or touch display.

Figure 2A:
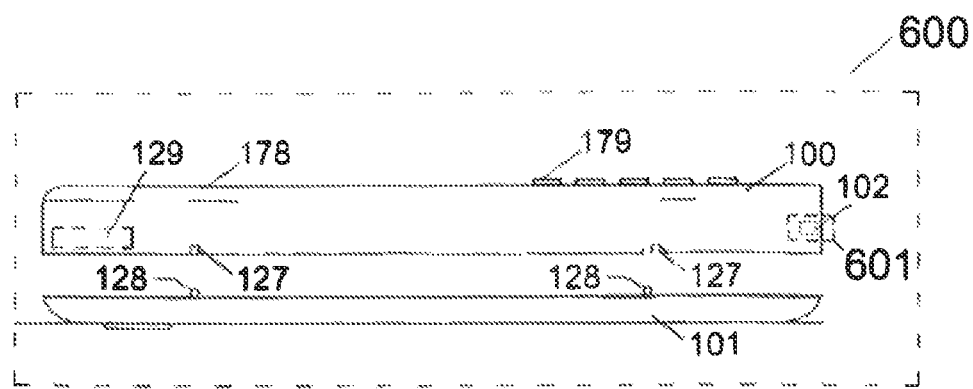
FIG. 2A shows a multimedia device formed by cellular phone, with removed back cover and auxiliary device individual.
Figure 2B:
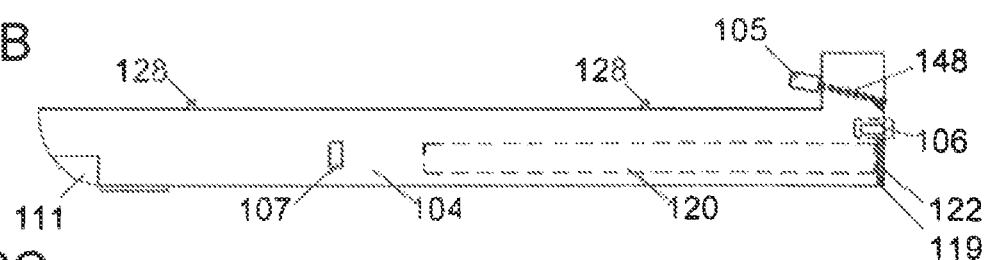
FIG. 2B—the part of the auxiliary device exceeding the shape of the cellular phone
Figure 2C:
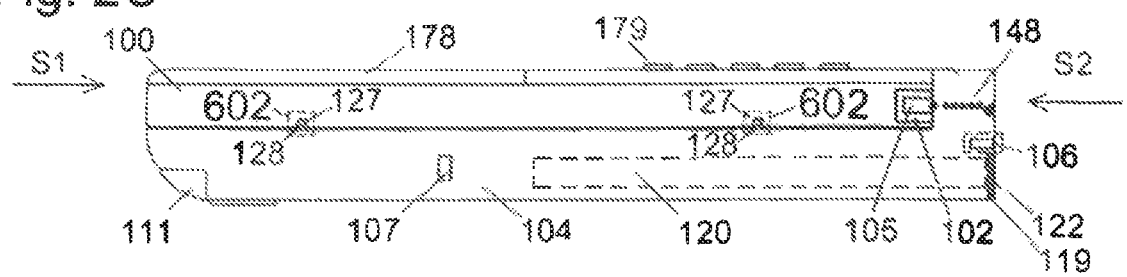
FIG. 2C depicts a composition made of multimedia device with connected auxiliary device.
Figure 2D:
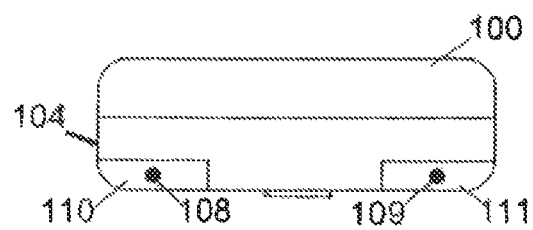
FIG. 2D depicts a view in direction "S1" on a composition made of multimedia device with connected auxiliary device.
Figure 2E:
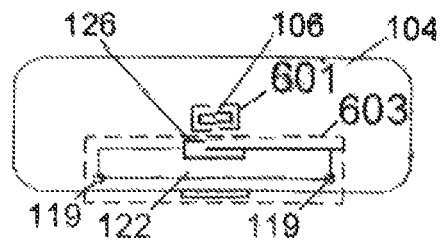
FIG. 2E depicts a view in direction "S2" on a composition made of multimedia device with connected auxiliary device.

FIG. 2A shows a multimedia device 600 formed by cellular phone 100, with removed back cover 101 and auxiliary device 104 individual, which extends functions of not adapted multimedia device 600. Connection of auxiliary device 104 on multimedia device 600 formed by cellular phone 100 is achieved by removing cover 101 and replacing it with auxiliary device 104. This solution preferably enables its easy electric, electronic and mechanic disconnection from auxiliary device 104. When there is no intention to use functions provided by auxiliary device 104, it can be removed and the cover 101 is used instead. It is possible to combine the auxiliary device 104 with the cellular phone only when the capacity of basic accumulator 129 needs to be strengthened, or when functions found in the auxiliary device 104 are to be used. It is not necessary to acquire auxiliary device at the same time as the multimedia device, it can be purchased later according to the user's needs. Thus, the multimedia device can be acquired by itself which results in savings, because all electric, electronic and mechanical parts for operating, connecting and interface with the multimedia device are preferably placed in auxiliary device 104. The price of acquisition of the multimedia device is limited to those units and parts needed for the multimedia device to function, and the price is lower since it doesn't include the auxiliary device. In this example, depicted on FIG. 2B, the part of the auxiliary device 104 exceeding the shape of the cellular phone 100 includes a connector 105 USB, which is a mechanical connection of the auxiliary device 104 that is inserted into counterpart 102 of cellular phone 100. The connector 105 is mounted flexibly using a flexible element 418 and is inserted into connector 102 of the cellular phone 100 thereby connecting the cellular phone to the auxiliary device. The storing mechanism 603 of the auxiliary device 104 has a small door 122 so that a discharged accumulator 120 of the auxiliary device can be locked via lock 126 to prevent accumulator 120 from sliding out of auxiliary device. At the auxiliary device 104 is situated another connector 106 preferably USM connector common for external communication of the auxiliary device and the multimedia device with preferably external PC, which can be used as a source of 5V for charging of accumulator 120 of the auxiliary device from external source. Preferably can be used a data switch 107 of external USB for switching data stream transferred by internal USB connector 105 either from the processor of auxiliary device, or from connector 106. FIG. 2C depicts a composition made of multimedia device formed by cellular phone 100 with connected auxiliary device 104. FIG. 2D depicts a view in direction "S1" and FIG. 2E depicts a view in direction "S2". Pushbuttons 110 and 111 described at FIG. 2D enable to transfer into multimedia device order and LEDs 108 and 109 preferably situated inside pushbuttons can sign the reaction to order. Pushbutton 110 serves for emergency calls and pushbutton 111 for resetting. Pushbuttons are located at easy accessible place at auxiliary device 104 which has advantage for immediate use of them in comparison with situation with using pushbuttons on touch screen of cellular phone 100, where it would be necessary first manipulate for displaying it on screen. On FIG. 2E is showed connecting element 601 made of connector 106, further is depicted door 122 with hinge 119 a lock 126 of door and connector 106. Discharged accumulators 120 in auxiliary device 104 can be preferably replaced by charged ones without interruption the operation of multimedia device. Operating accumulators 129 can be charged by means of storing mechanism 603 of accumulator without removing the auxiliary device 104 from the multimedia device 600 preferably made by cellular phone 100. So it is not necessary to charge accumulator by relevant cable to USM connector 106 and this connector remains free for use. The user is not forced to charge the cellular phone 100 through connector 102 from charger an in this way the phone is still ready for use. Another advantage of auxiliary device is a lot of functions, which support and extend the possibility of multimedia device 600. Advantage is also usage of not adapted cellular phones from line production. The auxiliary device 104 is clicked on the multimedia device 600 instead of the back cover. Connection and disconnection of auxiliary device may be done during the operation of multimedia device 600 without loosing any ability of multimedia device 600. Advantage after connection of auxiliary device is continuous uninterrupted operation of multimedia device 600 without necessity of charging its internal accumulator 129 by external charger, which is ensured by auxiliary accumulators 120 located in auxiliary device 104 whereas in auxiliary device 104 can be used accumulators from line production currently available on the market.

Figure 3:
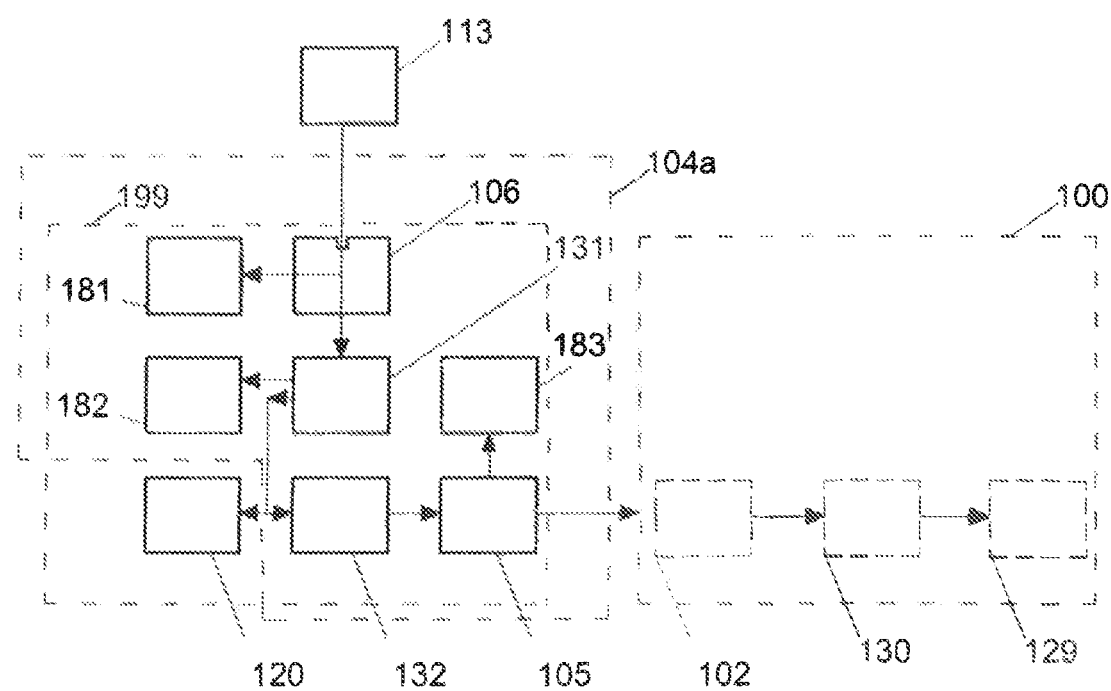
FIG. 3 illustrates block diagram of module continuously charging of basic accumulator, which is part of modified auxiliary device.

FIG. 3 illustrates block diagram of module 199 continuously charging of basic accumulator 129, which is part of modified auxiliary device 104a. This example illustrates charging of the basic accumulator 129 of cellular phone 100 and the auxiliary accumulator 120 at the same time from the charger 131, which simultaneously supplies the electric circuits of module 199 and also multimedia equipment 600 consisting with advantage of a cellular phone 100. In case when external source 113 is not connected, it is running recharging of the basic accumulator 129 of cellular phone 100 at the same time from the auxiliary accumulator 120, which is placed in the auxiliary device in the way, that is at first the voltage of auxiliary accumulator 120 modified by voltage transformer 132 to voltage by the specification for charging multimedia device, often 5V. Via second connector 105 USB of auxiliary device 104a and connector 102 USB of multimedia device with advantage formed by cellular phone 100 is this voltage used for recharging of the basic accumulator 129 via charger 130 of multimedia equipment. The advantage of this solution is based on fact that it is possible to use in the auxiliary device accumulators with different voltages regardless of voltage for recharging multimedia equipment accumulator. The auxiliary accumulator 120 placed inside in the auxiliary device is possible after discharging easily and quickly replace by another charged accumulator or recharge it from external source 113. Replacement of the auxiliary accumulator 120 of module 199, in which auxiliary device is placed inside can be realized during operation without removal of auxiliary device 104 or phone cover and without operation interruption of multimedia device preferably formed by cellular phone 100, because during auxiliary accumulator 120 replacement of auxiliary device, its operation is supplied from the basic accumulator 129. The auxiliary accumulator 120 can be replaced without limitation of operation and without separation of multimedia device with advantage formed by cellular phone 100 and auxiliary device 104a. The auxiliary accumulator 120 placed in auxiliary device can be recharged from external source 113 which is connected through next connector 106 to the charger 131, which ensures recharging by the way of the auxiliary accumulator 120 specification. All electronics related to accumulator recharging preferably placed in auxiliary device 199. The voltage states during accumulator recharging which is placed inside auxiliary device and presence of voltage on the voltage converter output is indicated by indicators 181, 182 and 183 which evaluate this voltages and with the advantage are monitoring this states and indicates by means of LED of various colors. Indicator 181 signals presence of connection to external voltage on next connector 106, in addition indicator 182 shows recharging of the auxiliary accumulator 120 situated in auxiliary device 199. The correct function of voltage transformer 132 and thus indirectly state of auxiliary accumulator 120, which is placed in auxiliary device, shows voltage indicator 183.

Figure 4:
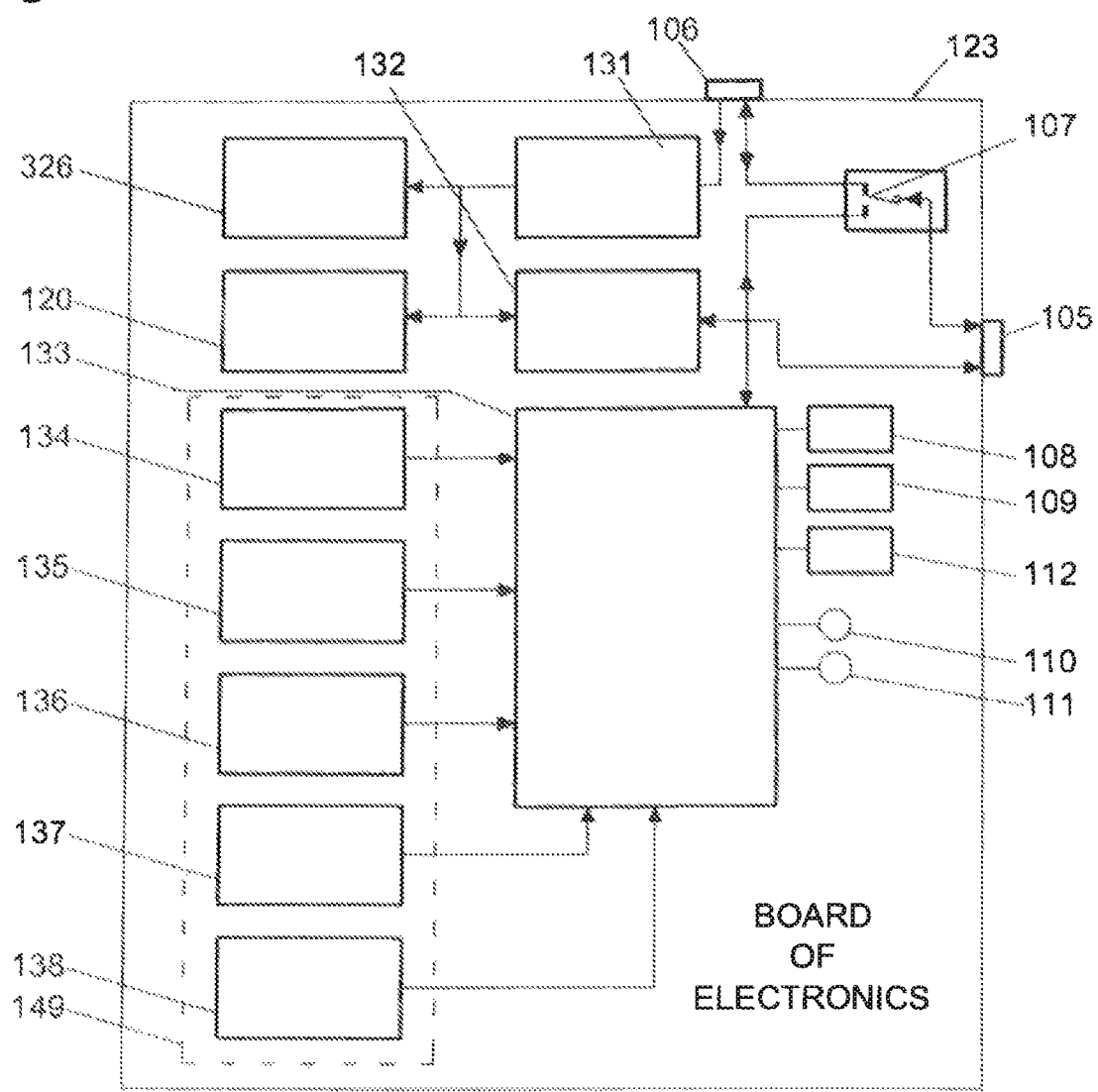
FIG. 4 illustrates block diagram of auxiliary device, electronics and all functions of which are placed on board of electronics on the auxiliary device board of electronics.

FIG. 4 illustrates block diagram of auxiliary device 104, illustrated on FIG. 2 and FIG. 4, electronics and all functions of which are placed on board of electronics 123 on the auxiliary device board of electronics. Auxiliary accumulator 120 placed in auxiliary device 104 can be very easily replaced by the use of small door 122 for the auxiliary device, without interruption of multimedia device operation and without separation of multimedia device from auxiliary device, is used for auxiliary device supplying through circuit 326, in which is auxiliary accumulator 120 placed and also used for charging of basic accumulator 129, which is placed inside the multimedia device. Auxiliary accumulator 120 can be in auxiliary device 199 placed directly on the board 123 of electronics or can be with this board connected and be recharged without removing it from auxiliary device 104 by the external power supply through next connector 106 of external USB of auxiliary device and charger 131. Continuous recharging of the basic accumulator 129, illustrated on FIG. 1, of multimedia equipment 600 is ensured from voltage transformer 132 and linked up USB connectors 105 and 102. This enables uninterrupted operation of multimedia device without necessity to recharge basic accumulator 129 by the external charger. The possibility to connect USB cable for data transfer is the main function of USB connector 102 of multimedia device, which is by connection with multimedia device and auxiliary device covered and is used by auxiliary device except charging the accumulator of multimedia device end as well for data transfer between microprocessor 133 of multimedia device and multimedia device which would limit using the cable of multimedia device for connecting USB cable. The problem of multimedia device connector USB covering solve the data switch 107 of external USB, which switches data path of multimedia device connector 102, which is inserted into the second connector 105, between microprocessor 133 and next connector 106 of auxiliary device, so next connector 106 can from the point of view of data transfer and USB cable connection fully substitute function of multimedia equipment connector 102, for example for PC connection. Preferably it is possible to place into auxiliary device 104a next modules and circuits, namely block 149 of communication modules which ensure data transfer by next communication protocols, which are in multimedia auxiliary device not available. This data is evaluated by microprocessor of auxiliary device 133 and is transferred into multimedia device and alternatively into next device. The block 149 of communication modules with advantage includes module 134 for signal transmission in the frequency band 5.5 kHz, which receives and transmits into cellular phone 100 data, which ordinary cellular phone is not able to receive. This data is preferably heart rate data, transmitted by chest belt, further a block o transmission 135 using Bluetooth Low Energy (BLE), ANT, alternatively Bluetooth (BT) and next communication protocols with advantage module 136 of RF transmission (band 800-900 MHz), module 137 of WiFi transmission and also module 138 of ZigBee protocol transmission.

Up to date multimedia equipment, for example cellular phones with touch display, have available for multimedia equipment applications control only virtual keyboard and icons displayed on touch display, which is not I the time of multimedia equipment sleeping regime active. Touch display operation is very energy demanding that is why it is required to operate multimedia equipment in the regime of automatic sleeping, as long as it is possible. But multimedia equipment activation, which is in the sleeping regime, requires from user a few operation, what is lengthy and makes substantial trouble in the moment in which it is necessary call for help for person with loss of consciousness health problem, loss of spectacles, in darkness and similar. This problem is solved by push buttons 110 and 111 placed on auxiliary equipment 104a. The advantage over current state is prompt accessibility and identification of push buttons by touch even in dark and immediate multimedia equipment activation, even if it is in the sleep regime. Push buttons 110 and 111 activate microprocessor 133 of auxiliary equipment, which immediately activate corresponding applications in multimedia equipment regardless if is in this moment the multimedia equipment active or in the sleeping regime. The advantage of push buttons 110 and 111 using for calling for help in the case of emergency, at what time is instantly after multimedia equipment activation send message to specified location including case that the multimedia equipment is in the energy saving sleeping regime. The advantage for fast help calling by the use of multimedia equipment is using push the buttons 110 and 111 on the auxiliary equipment with advantage labeled Panic and Reset, which in cooperation with microprocessor 113 of auxiliary equipment and its software, indicators 108 and 109 with advantage LED and acoustic signalization 112, controlled by microprocessor 133. With advantage is after the press of push button 110 by which is assigned function panic going on starting of acoustical and optical warning announcing that was activate request to send call for help by the acoustic signalization 112 and optical signalization by indicator 108 with advantage red color LED alert by blinks activation of request to call for help. During the period of which is warning signals activated it is possible to cancel the activation of request to send call for help by the use of push button 111 with advantage labeled Reset. After this the indicator 108 stops blinking and also stops warning signal of acoustic signalization. If the request to send call for help was not canceled by push button Reset, the blinking of indicator 108 is changed to permanent lighting until multimedia equipment accept request to send call for help. Acceptance of request to send call for help the multimedia equipment confirms, the indicator 108 stops lighting, stops acoustic signalization and for short time is lighting indicator 109 with advantage green color LED confirms call for help acceptance. Push buttons 110 and 111 in addition reduce energy consumption because both multimedia equipment and auxiliary equipment 104a can be in the sleeping regime also in the case of probability of incident requires urgent call for help.

Figure 5:
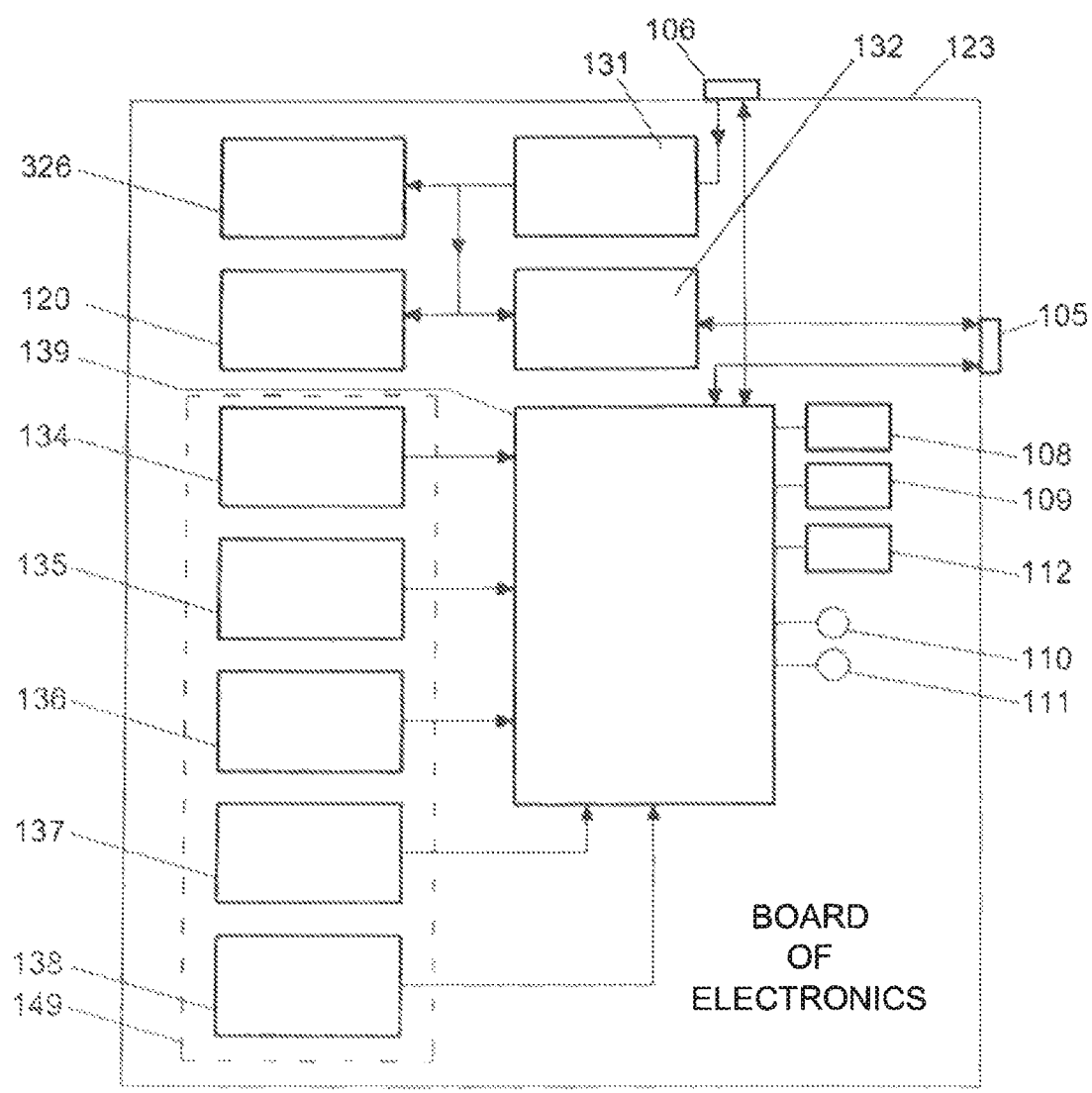
FIG. 5 shows block diagram of other auxiliary device, with board of electronics where ordinary microprocessor is substituted by microprocessor with two USB ports.

FIG. 5 shows block diagram of other auxiliary device, with board 123 of electronics where ordinary microprocessor 133, as presented in the FIG. 4, is substituted by microprocessor 139 with two USB ports, which can be used for connection with two USB connectors for controlling data flow transferred through these connectors. After inserting connector USB 102 of multimedia device into USB connector of auxiliary device the data stream is directed to the microprocessor or to the first USB connector 106 of two ports microprocessor which enables communication of multimedia device through connector 102 covered by auxiliary device and first USB connector 106 with another device connected with USB cable to auxiliary device. As an example of utilization of auxiliary module of receiver 134 of signal 5.5 kHz situated in auxiliary device is illustrated as connection of chest belt 145 for sensing heart rate and transmitting it wirelessly in frequency band 5.5 kHz. Another example of evaluation and further processing of heart rate by microprocessor in auxiliary device is utilization of chest strap 146 for sensing with wireless transmission using Bluetooth module with transmission module 135 of auxiliary device.

Figure 6:
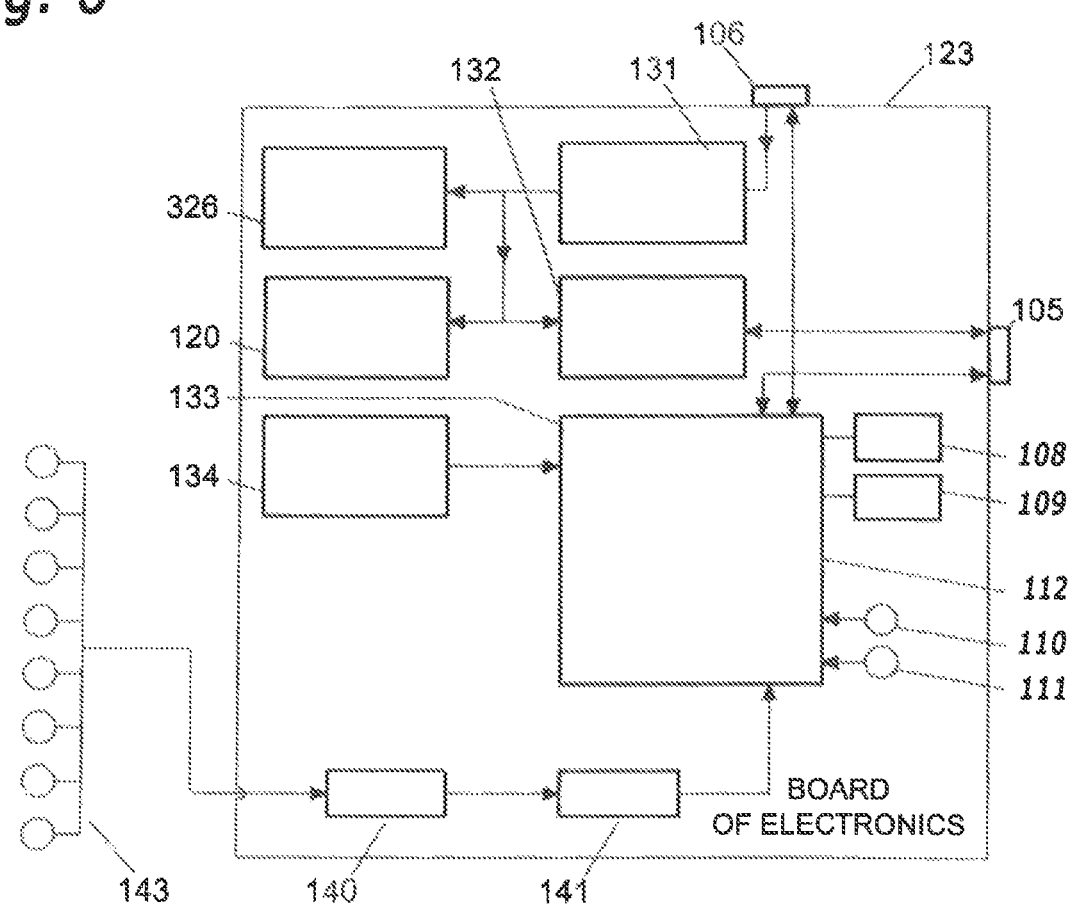
FIG. 6 illustrates extended block diagram for processing ECG signals by auxiliary device showing continuously the heart activity by means of auxiliary device.

FIG. 6 illustrates extended block diagram for processing ECG signals by auxiliary device showing continuously the heart activity by means of auxiliary device and transferring results for graphic displaying and achieving to multimedia device through connector 105. It can be preferably monitored if the heart activity is normal, or if occurs irregularities in it or if it reveals acute or proceeded any heart defect, especially defect of myocardium, specially infarct of myocardium and performs continuous screening of ischemic disease of heart at load and displays on display of cellular phone ECG curves, time slopes of heart pulses and that as long-duration program in conditions of common for patient for instance at sport. In this case auxiliary nodules and elements are used such as connector 140 for inputs of ECG leads and module 141 "Front End". ECG electrodes 143 placed on body skin of patient sense the low voltage originated by the heart activity are connected through connector 140 to the input of auxiliary module 141 Front-End which amplifies the signals, filters, digitizes ad adapted and transforms for consecutive processing by microprocessor 142.

Figure 7:
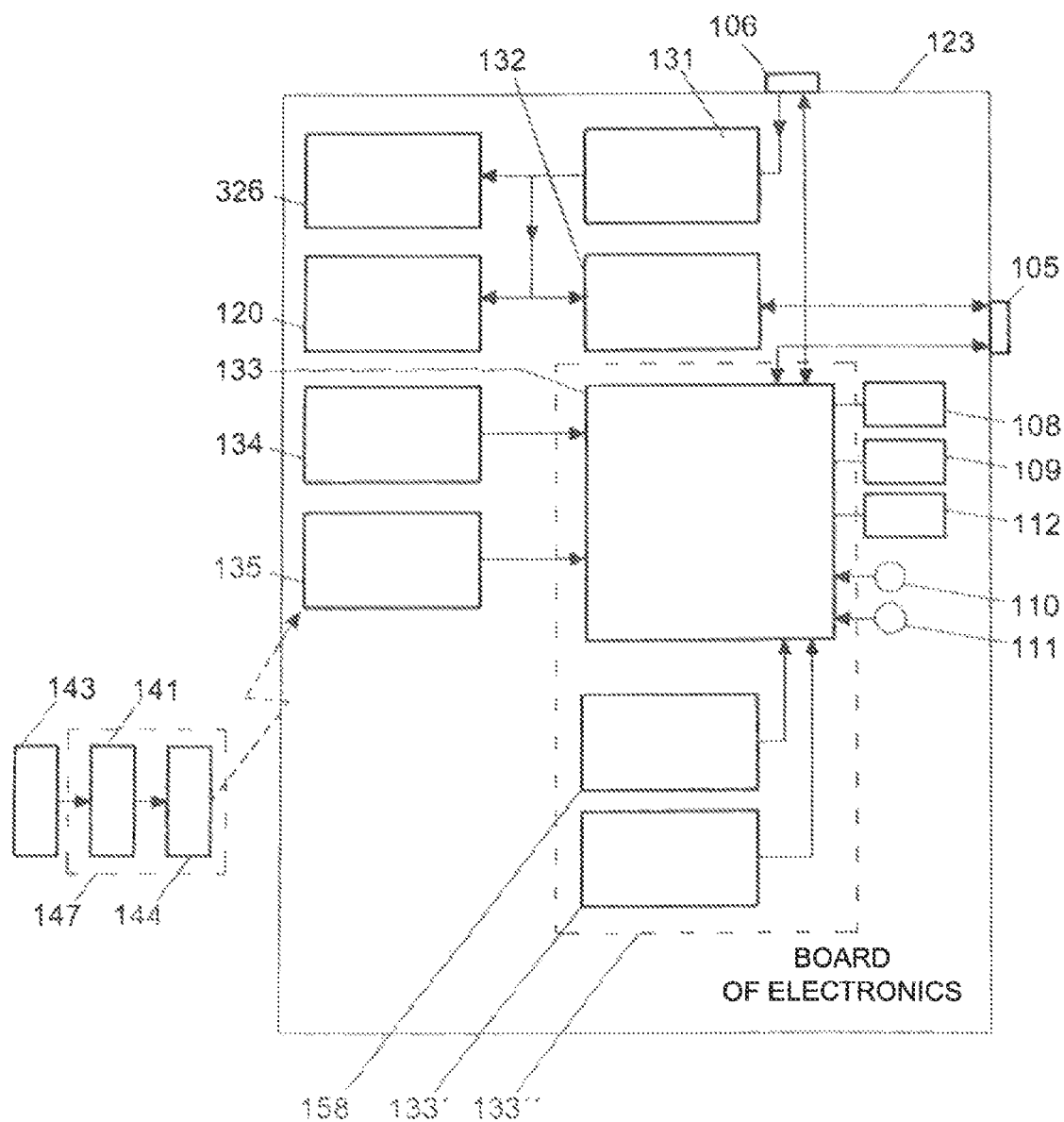
FIG. 7 shows arrangement of auxiliary device for evaluation ECG signals, which are preprocessed by electronics situated close to ECG electrodes.
Figure 8:
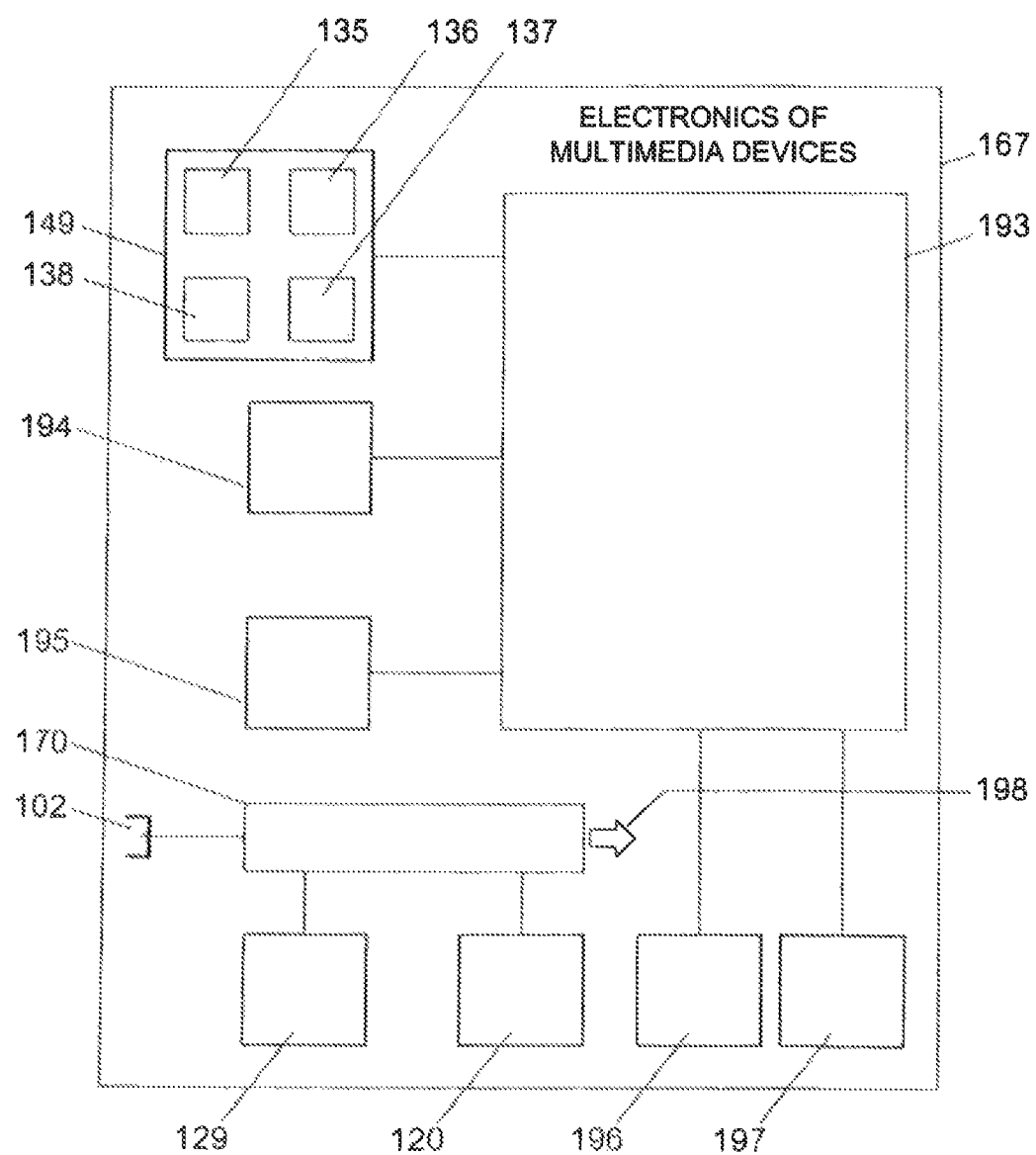
FIG. 8 presents block diagram of modules situated on board of electronics of multimedia device.

FIG. 7 shows arrangement of auxiliary device for evaluation ECG signals, which are preprocessed by electronics situated close to ECG electrodes 143, for instance of a strap 147 with EGC electronics where is also placer a module 141 Front-End with communication module BT/BLE 144 ensuring wireless processed data transfer from module 141 "Front End" into auxiliary transfer module 135 BT/BLE/ANT. Module 141 "Front End" is preferably fastened on chest strap so as the leads from contacts were as short as possible. Advantage of this arrangement is shortening of leads for reducing the level of signal jamming. The ECG electrodes can be with advantage as a part of strap with electronics. Using auxiliary module of microprocessors using one or more microprocessor the power can be enhance and the data processing speed can increase. Microprocessor 133, 158 communicate with other auxiliary units through microprocessor 142. In each microprocessor ca be used different operational system such as Android, Windows Mobile, Symbian and in this way to optimize possibilities of auxiliary device with regards to requested applications. FIG. 6 presents block diagram of modules situated on board of electronics 167 of multimedia device 600. To the operational module 193 of multimedia device are connected modules 196 of display, keyboard module 197, block 149 of communication modules, preferably containing modules of transfer including modules 135 of BT/BLC/ANT transmission, module 136 of RF transmission, module 137 of WiFi transmission, module 138 of ZigBee transmission and auxiliary module 194 of microprocessors and 195 module of multimedia device. Operational accumulator 161 and auxiliary accumulator 162 are connected to electronics 170 of accumulators charging, which aside from charging of both accumulators provide also supply circuits of multimedia device, which is figured by arrow 198.

Figure 9:
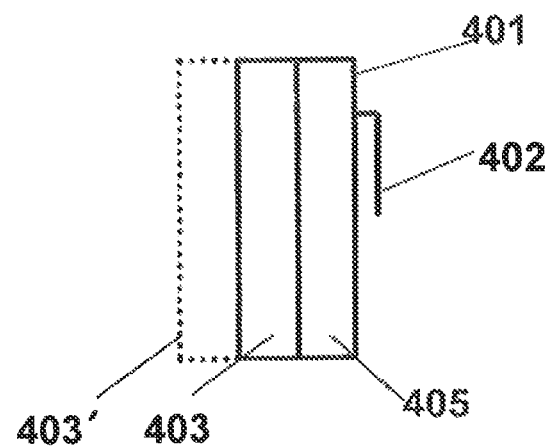
FIG. 9 depicts an example of the bag configuration of two multimedia devices, enhancing its potential use upon connecting the multimedia device by extending substantially its operation without interruption with continuous charging the accumulator of multimedia device.

FIG. 9 depicts an example of the bag configuration 401 of two multimedia devices 600, enhancing its potential use upon connecting the multimedia device 600 by extending substantially its operation without interruption with continuous charging the accumulator 129 of multimedia device. Furthermore, the bag 401 contains the additional electronic devices placed on the circuit board 123 that support applications of the connected multimedia device. The bag 401 is preferably made of plastic, leather, or other suitable material, and it can store the multimedia devices. In the period of not using the multimedia device 600, it is stored in the space 403, the second multimedia device is stored in the space 403', the space 405 is used to store the backup accumulator 120 and the clip 402 serves to attach the bag 401 to the clothes of user.

Figure 10:
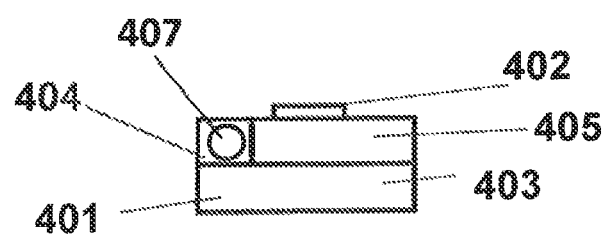
FIG. 10 depicts clearly the space to store the connecting cable-twisted cord.

FIG. 10 depicts clearly the space 404 to store the connecting cable-twisted cord 407.

Figure 11:
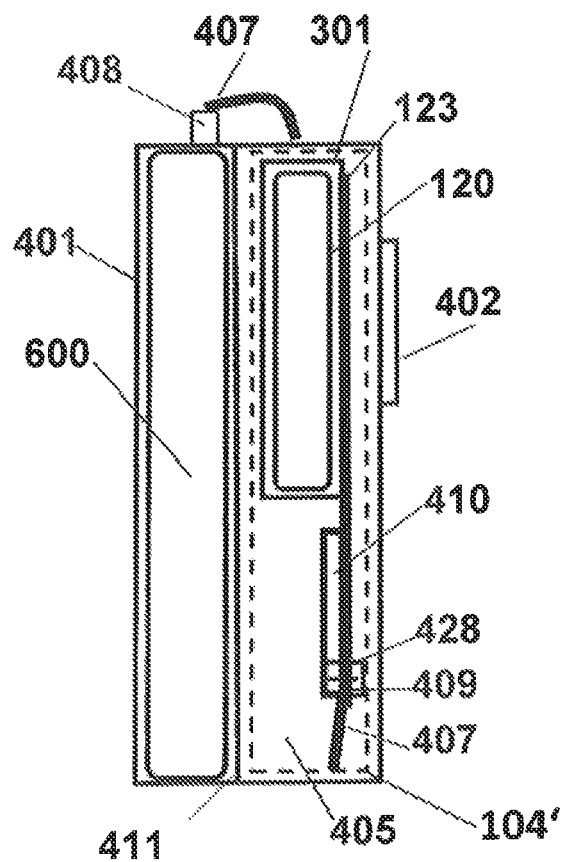
FIG. 11 depicts a configuration example of the bag, using it for connecting the multimedia device with the module of electronics by the twisted cord, enabling data connection and power supply.

FIG. 11 depicts a configuration example of the bag 401, using it for connecting the multimedia device 600 with the module of electronics 410 by the twisted cord 407, enabling data connection and power supply. The twisted cord 407 serving to connect the multimedia device 600 with the circuit board 123 of the bag stored in the space 404 for the patch cord. This cord allows easy handling. The twisted cord 407 may be stretched out when used. Upon release, it returns back to its original short form. The adjusted multimedia device 600 is connected to the circuit board 123 of the bag 401 by the twisted cord 407 with the USB connector 408, led to the multimedia device 600, and the USB connector 409 of the circuit board 123. The case 420 of the accumulator 120 is located on the circuit board 123 as well as the module of electronics 410 to include all electronic circuits of the bag 401 expanding the possibilities of multimedia device 600 including the continuous recharging its accumulator.

Figure 12:
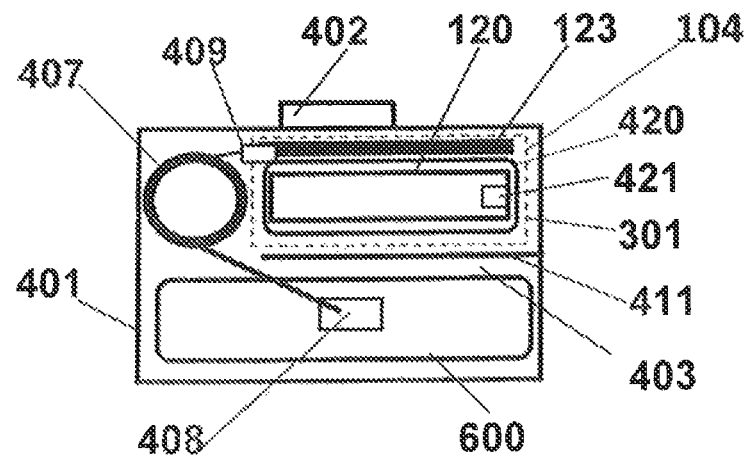
FIG. 12 depicts the top view of the bag, the accumulator is separated by the partition and it is connected through the circuit board with the electronics module.

FIG. 12 depicts the top view of the bag 401. The accumulator 120 is separated by the partition 411, and it is connected through the circuit board 123 with the electronics module 410 shown in the FIG. 11, interconnected to the multimedia device M. The accumulator is stored in the case 420 fitting to the printed circuit of electronics. Upon pushing the latch 421 away to secure the accumulator 120 in the retracted position, it is pushed out by the spring 125 enabling an easy and fast replacement. The bag is equipped with the detachable clip 402 to enable the attachment to the clothes of user.

Figure 13:
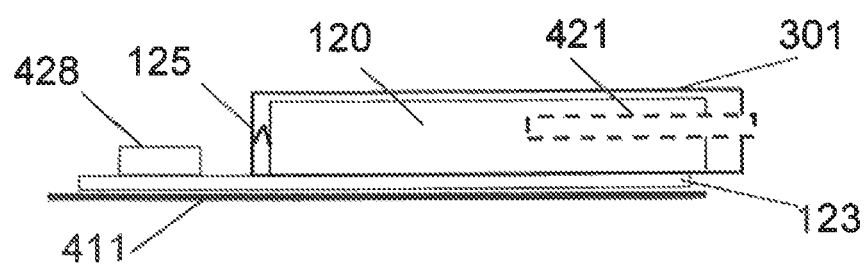
FIG. 13 depicts the location of the case of the accumulator on the circuit board.

FIG. 13 depicts the location of the case 420 of the accumulator 120 on the circuit board 123. The accumulator 120 is preferably inserted in the case 420, and it is secured against the movement by the latch mechanism 421. The USB connector 428 is intended to connect the circuit board 123 with the connector 409 of the bag, hence with the multimedia device 600. According to needs, or in case of failure, the circuit boards 123, equipped differently, are preferably replaced in the bag 401 for a spare part.

Figure 14:
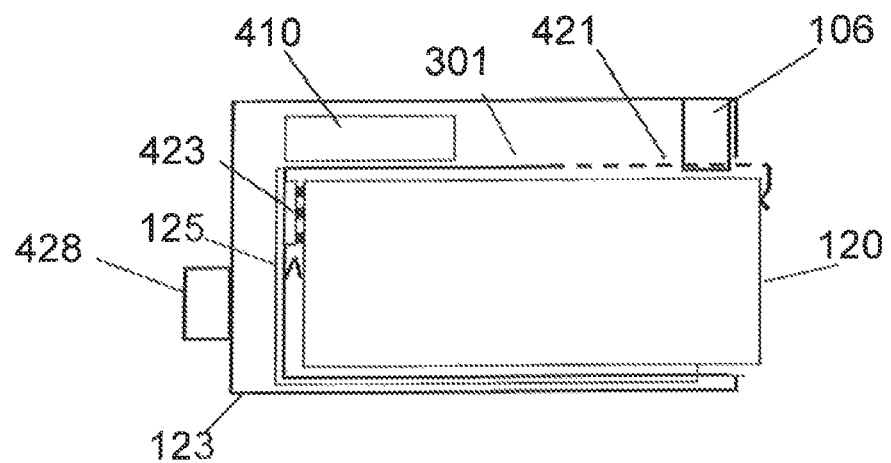
FIG. 14 specifies the location of latch in the case of the accumulator, containing the connector either to ensure electrical connection of the accumulator with the circuits either located on this board.

FIG. 14 specifies the location of latch 421 in the case 301 of the accumulator 120, containing the connector 423 either to ensure electrical connection of the accumulator 120 with the circuits either located on this board. Upon releasing the latch 421 manually, the spring 125 ejects the accumulator 120 out of the case 301. The electronic circuits, located on the circuit board 123, are marked like the module of electronics 410. The USB connector 106 serves to connect an external source of power to charge the accumulator 120, and it can also be used to communicate with an external PC, if the data signals of the USB connector 106 are connected to the electronic circuits of the electronic module 410. The advantage of solution lies in the fact that the circuit board 123 is electrically connected through the connector 428 only, hence to enable an easy replacement. It is therefore easy to place in the bag 401 and replace the circuit boards with various functions of the electronics module 410.

FIG. 15 depicts an option of leading and placing the twisted cord 407 outside the bag 401. In this case, the twisted cord 407, connecting the multimedia device 600 with the circuit board 123, extended by a passage created in the bottom part of bag 401; it depicts how the twisted cord 407 is led through the upper part of the bag 401. Moreover, the preferably removable inlet extension bit 433, enabling to speed up and facilitate the insertion of the multimedia device 600 into the bag 401 by its broadened end, is depicted.

Figure 16A:
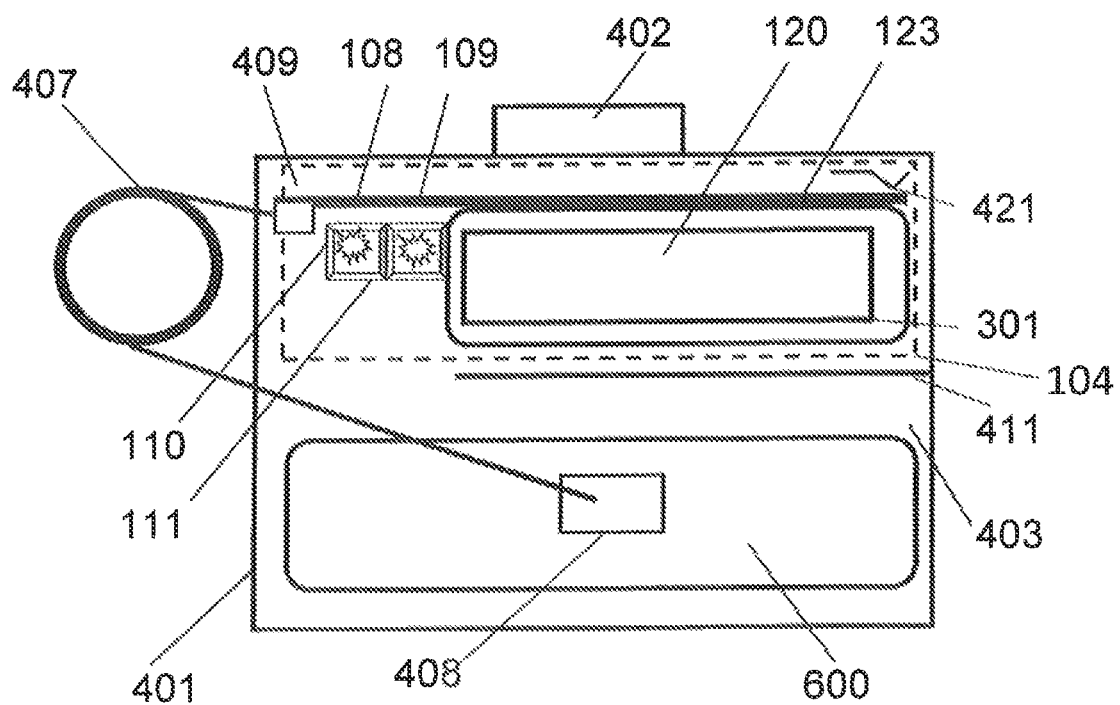
FIG. 16A depicts how the twisted cord with the connectors is led and located and their connection to the circuit board and the multimedia device.

FIG. 16A depicts how the twisted cord 407 with the connectors 408 and 409 is led and located and their connection to the circuit board 123 and the multimedia device 600. The buttons 110 and 111, preferably assigned by the Panic and Reset functions, as well as indicators 108 and 109 preferably the LED indicators, located in the buttons 110 and 111 are placed on the circuit board 123.

Figure 16B:
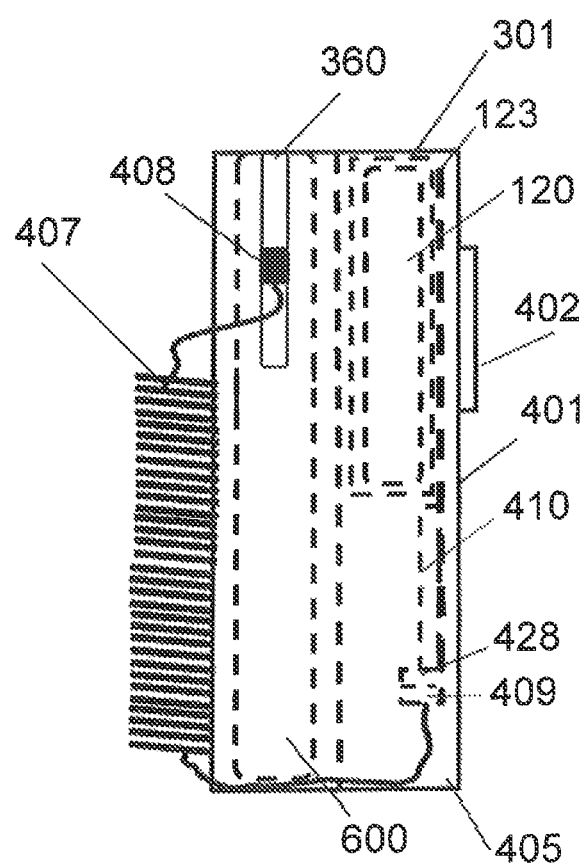
FIG. 16B depicts the option of using the twisted cord led outside the bag, if the multimedia device had a connector located on side of the case.

FIG. 16B depicts the option of using the twisted cord led outside the bag 401, if the multimedia device 600 had a connector located on side of the case. The connector 408 of the twisted cord, preferably a corner one, is inserted in the connector of multimedia device through the gauge 360 created to this end on side of the bag.

Figure 17B:
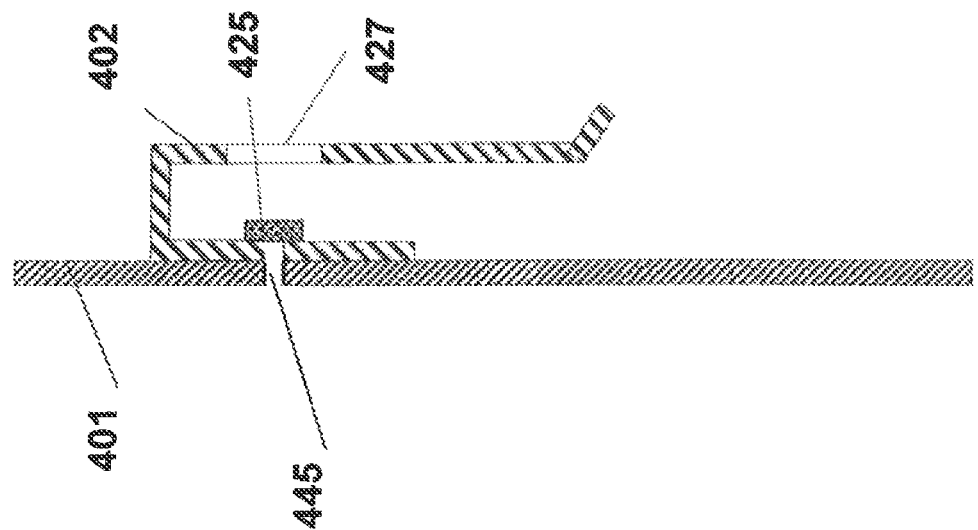
FIG. 17B depicts side view of the detachable clip.
Figure 17A:
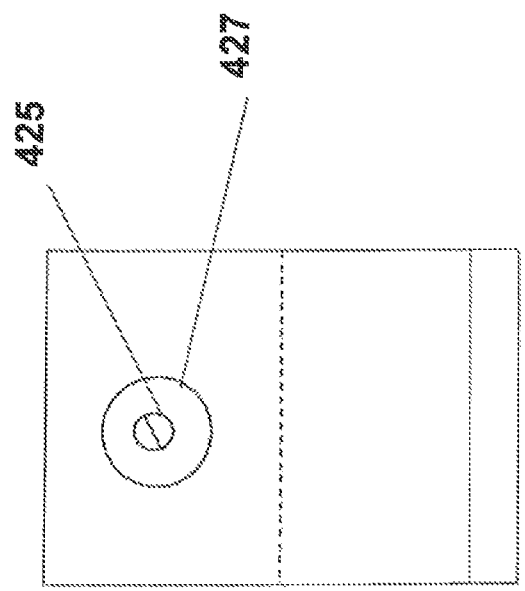
FIG. 17A depicts the detachable clip to ensure the attachment in the pocket able to be removed or fixed by the screw in the nut connected firmly with the wall of the bag.

FIG. 17A depicts the detachable clip 402 to ensure the attachment in the pocket able to be removed or fixed by the screw 425 in the nut 445 connected firmly with the wall of the bag 401. The hole 427 serves as an access area for the clip assembly and disassembly.

FIG. 17A depicts side view of the clip 402.

FIG. 18A depicts the configuration of the bag 401, using the self-acting reel 412 and the cord 413 with the connector 414 and/or the connector 415 to enable the link of the multimedia device 600 to the electronics module 410 of the bag 401. By pulling out the multimedia device 600, the connecting cord winds off the reel 412. By storing the multimedia device 600, the cord 413 itself is automatically re-winded on the reel 412 which is placed automatically on the bottom of the bag 401. The detail 1 depicts the side view of the bag 401.

FIG. 18B depicts side view of the bag 401 from FIG. 18A.

Figure 19B:
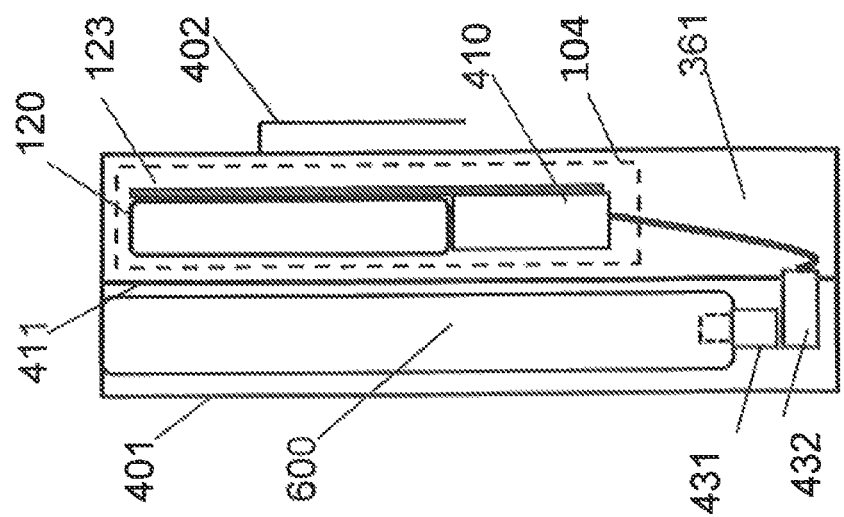
FIG. 19B depicts a side view of the automatic connecting/disconnecting the multimedia device to/from the circuits board of the bag.
Figure 19A:
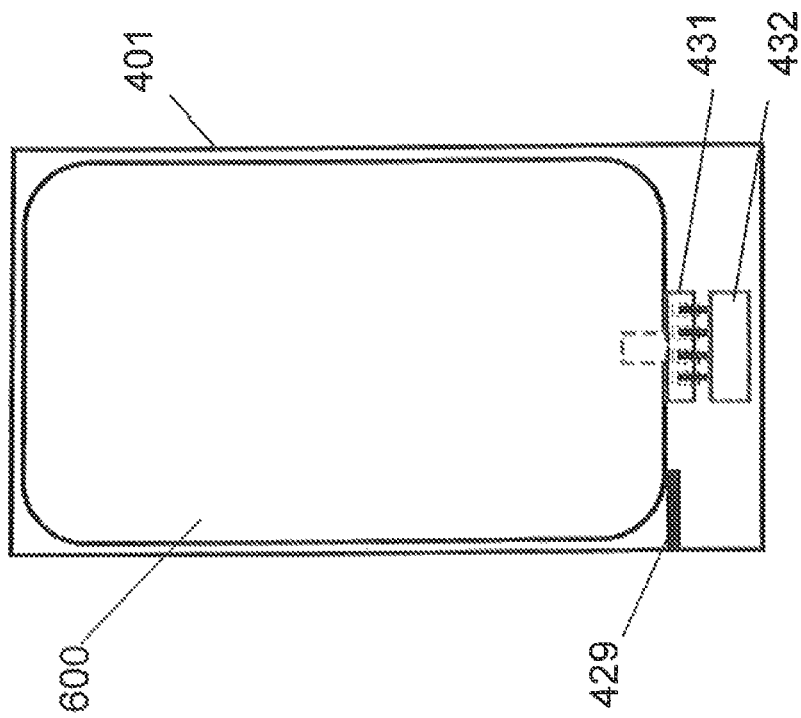
FIG. 19A depicts the automatic connecting/disconnecting the multimedia device to/from the circuit board of the bag simply by plugging it in the bag to the stop.

FIG. 19A depicts the automatic connecting/disconnecting the multimedia device 600 to/from the circuit board 123 of the bag 401 simply by plugging it in the bag 401 to the stop 429. The non-adapted multimedia device with the reduction connector 431 inserted in the USB connector 102 of that multimedia device may be used. The contacts of the reduction connector shall be inserted in the connector 432, designed for automatic guidance of the connector, preferably attached to the counter 411, connected to the circuit board 123 by the cable 361, as shown in the FIG. 16B. In addition, the adjusted multimedia device prepared so as the connector intended for inserting it in the connector 432 forms its part with the latter's configuration being designed for automatic guidance of the connector so as the reduction connector 431 is not used.

FIG. 19B depicts a side view of the automatic connecting/disconnecting the multimedia device 600 to/from the circuits board 123 of the bag 401.

Figure 19C:
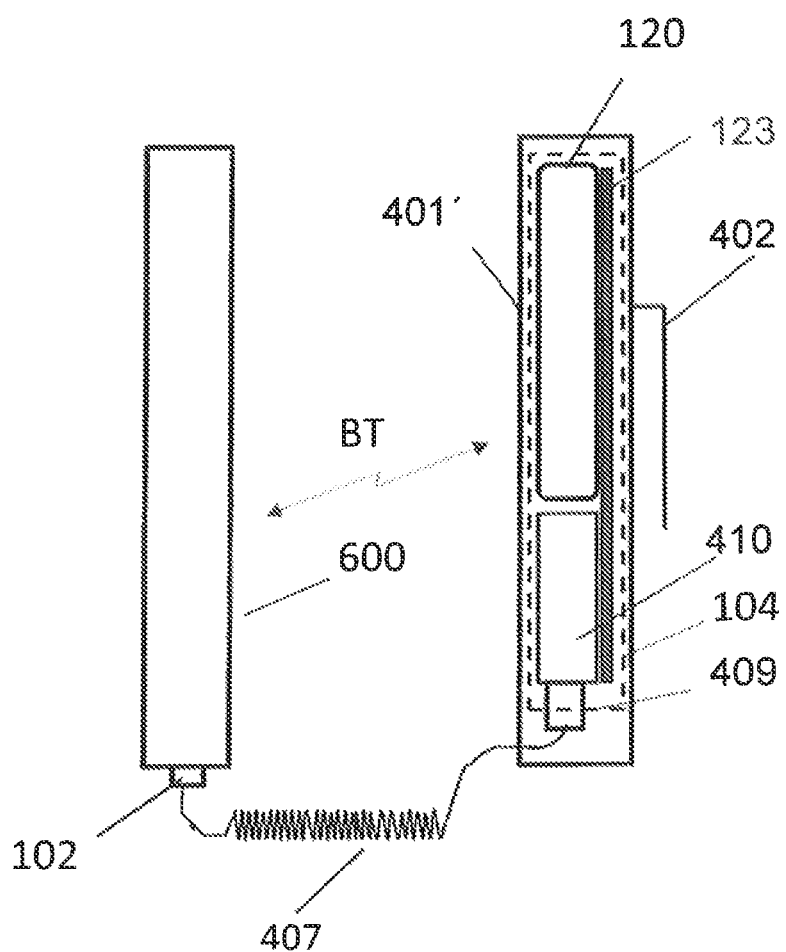
FIG. 19C illustrates a diminished version of the bag, which serves just for placing the accumulator of the circuit board, with the multimedia device placed separately.

FIG. 19C illustrates a diminished version of the bag 401', which serves just for placing the accumulator 120 of the circuit board 123, with the multimedia device placed separately, e.g. in the same pocket, together with the bag 401'. The communication between the multimedia device 600 and the circuit board 123 is pursued by mean of the twisted cord 407, with the connectors on both ends, or the radio connection, preferably via Bluetooth, inserted in the connector 409, and similarly in the connector 102, preferably via USB of multimedia device. Wireless connection of multimedia device with the bag 401' may also be used, albeit the advantage of continuous accumulator charging of the multimedia device is lost.

Figure 19D:
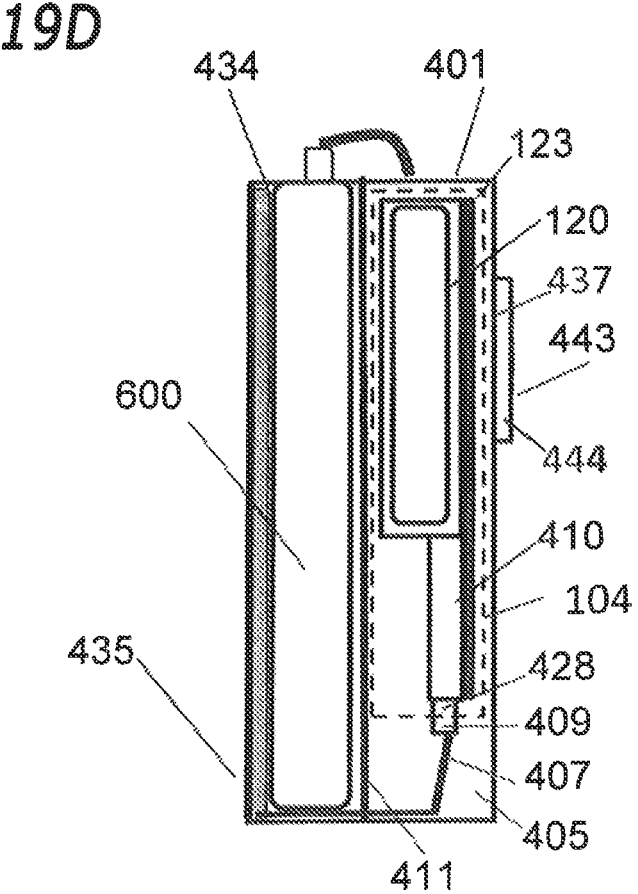
FIG. 19D depicts an enhancement of possibilities of the multimedia device, placed in the bag, by mean of the additional display.

FIG. 19D depicts an enhancement of possibilities of the multimedia device 600, placed in the bag 401, by mean of the additional display 434, preferably protected against scratching by the protective foil 435. The additional display 434, preferably a touch screen, is placed in the bag 401, and it is connected by cable, or via Bluetooth, with the circuit board 123. The bag 401 is attached to the belt of trouser by mean of the fixture mechanism 443, shown in the FIGS. 19E and 19G, enabling easy pull out of the bag to allow viewing the display 434 through the hole 474 in the bag.

Figure 19E:
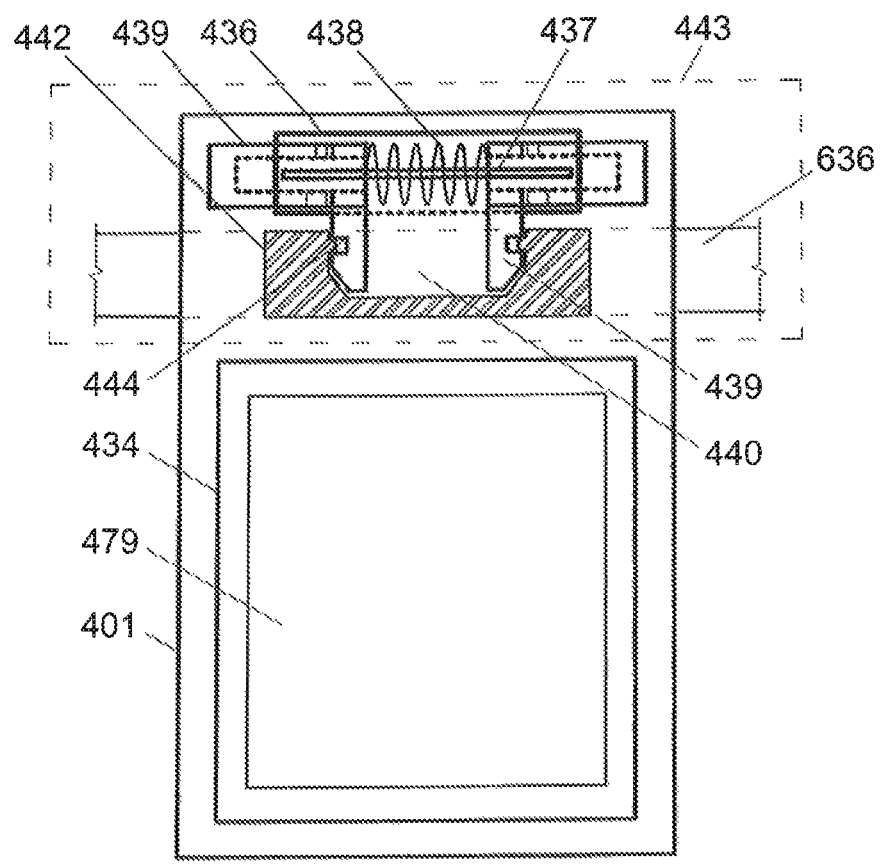
FIG. 19E depicts an example of the fixture mechanism to enable the bag fast pinning/unpinning from the strap attached to the user's body so that the display.

FIG. 19E depicts an example of the fixture mechanism 443 to enable the bag 401 fast pinning/unpinning from the strap attached to the user's body so that the display 434, preferably a touch screen, may be viewed to control the auxiliary device. The lower part of the case 436 of the fixture mechanism, connected with the bag 401, contains the groove 440, with the sliding deadbolts 439 placed therein, put on the guiding rod 437, and pushed by the spring 438 towards extreme positions limited by the groove 440. The auxiliary display 434, visible through the hole 479 in the bag 401, is mounted on the circuit board 123.

Figure 19F:
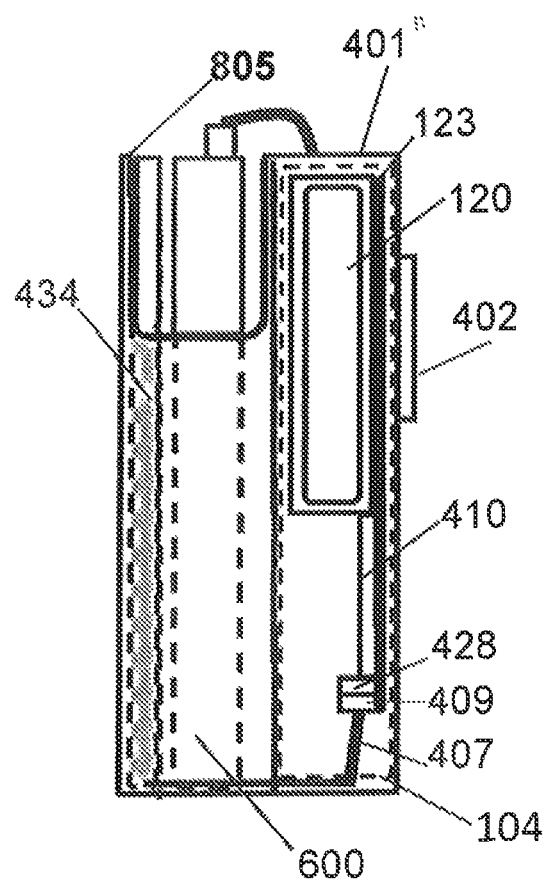
FIG. 19F depicts the bag enlarged by the storage space for controlling the removable additional display.

FIG. 19F depicts the bag 401", enlarged by the storage space for controlling the removable additional display 434', preferably a touch screen, interconnected wirelessly via Bluetooth, or the extendable cord, preferably the twisted cord 407 with the circuit board 123. Take out the multimedia device 600, or the additional display 434 is enabled by the cutout 805 in both sides of the bag 401", with the different width of the multimedia device 600 and the additional display 434 making it possible to distinguish both devices by touch.

FIG. 45G depicts the pin/unpin procedure of the bag by mean of fixture mechanism. By sliding in the bag 401 in direction of arrow, connected firmly with the fixture mechanism, the deadbolts 439 are inserted in the eye 4, firmly attached to the belt 636. The beveling ends 810 of deadbolts 439 of fixture mechanisms 443 cause that the pressure of spring 438 is overcome and compressed to allow inserting them in the eye 442, and subsequently latching the deadbolt 439 in the groove 444. Unpin the bag is easy upon releasing the deadbolts 439 by pressing them in direction of horizontal arrows.

Figure 19H:
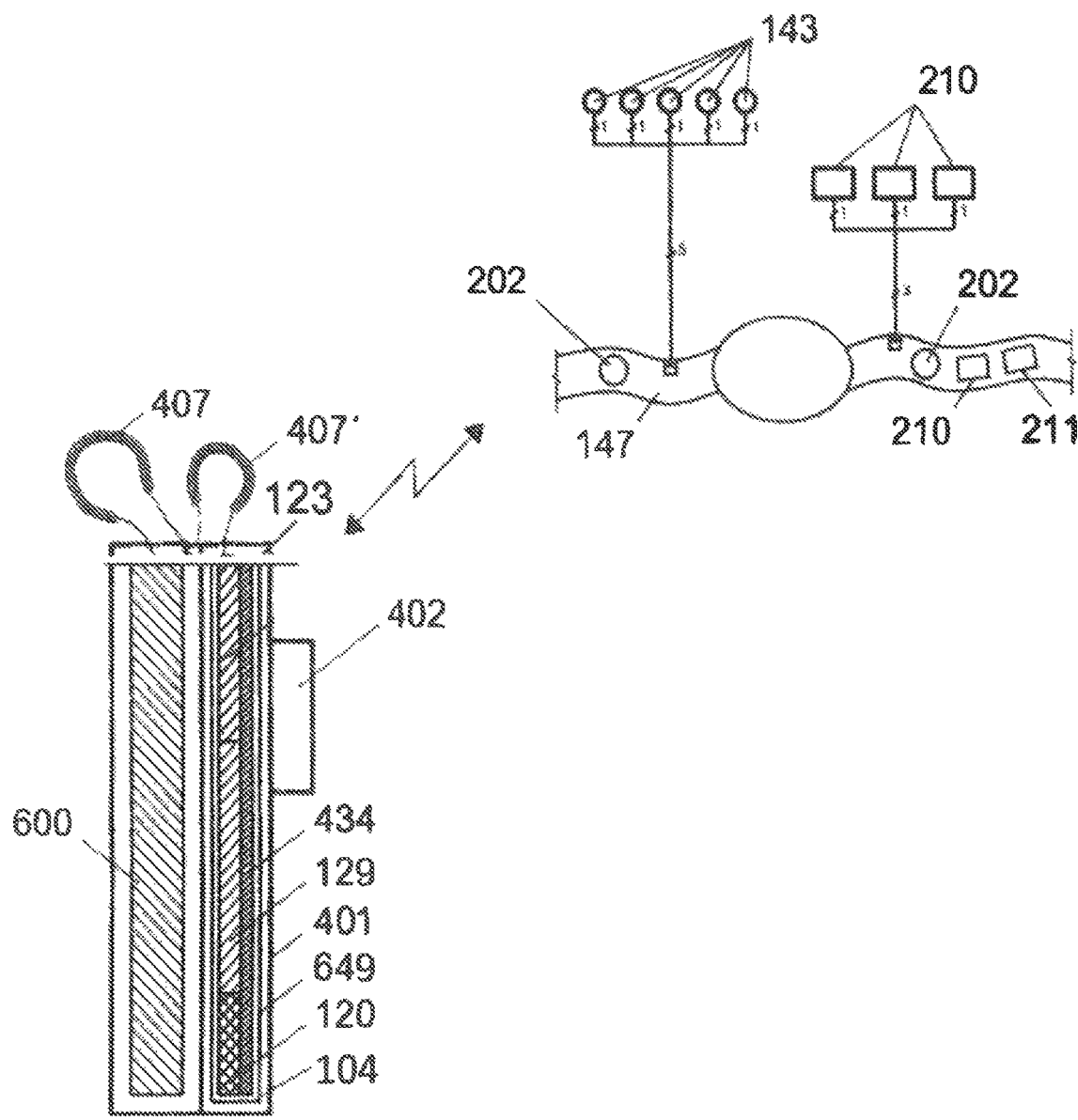
FIG. 19H depicts the removable circuit board of the auxiliary device equipped with the display and the additional removable accumulator placed in the bag.

FIG. 19H depicts the removable circuit board 123 of the auxiliary device 104, preferably equipped with the display 434 and the additional removable accumulator 120 placed in the bag 401, where the circuit board 123 with the basic accumulator 129 is preferably connected to the bag 401 by mean of the twisted cord 407', whereas the multimedia device 600 is connected to the bag 401 by the twisted cord 407, or preferably the circuit board 123 with other wireless connecting devices, preferably via Bluetooth, or the network of mobile operator, or other appropriate media. In this case of wireless connection, the twisted cords are preferably disconnected. The circuit board 123 is preferably placed in the case 649, with the hole therein enabling the view to the display 434, creating by this a separate unit of the auxiliary device 218. The circuit board 123, preferably containing the display 434 is preferably worn separately without the bag 401. In this case, it is wirelessly linked with the multimedia device 600 and other devices. As an example of other wirelessly linked device, there is a link of the chest belt 147 depicted here for the sake of processing the ECG heart signal via Bluetooth to process the heart pulse by mean of the induction circuit in 5.5 kHz band.

FIG. 19I The circuit board 123, preferably equipped with the display 434, is placed in the bag 401, or it may even be used without the bag 401, by placing it in the pocket 230 as an example. In this case, it is linked wirelessly to other device, preferably the ECG, or the heart pulses 146, ECG belt 419 or chest strap 146 heart pulse, by mean of the multimedia device 600, the PC 418, or via the network of mobile operator 803 to the server 806. In the storing mechanism 603 of the accumulator, enabling its replacement and the basic accumulator 129, it preferably contains the additional accumulator 120, which is replaceable in the operation. In case the circuit board 123 is intended for processing the ECG heart signals, it is required to link it, in a galvanic way, to the ECG electrodes 143 by the cable 234, led under the shirt 641, around its end, through the top end of trousers in the pocket 230, preferably to the clip 402, with the extendable cord attached thereto, preferably the twisted one, or the cord with the reel of the cable connecting the circuit board 123 with the ECG electrodes 143'.

FIG. 19J depicts an example of distribution of electrodes of the three-lead ECG sensing, i.e. placing the ECG electrodes 143 on the chest belt 147 with the shoulder straps 232 with the electrodes 231. The interlink of ECG electrodes 143 is also depicted particularly with the circuit board 123, serving in the current example to process the ECG signals, placed in the pocket 230 by mean of the clip 402, the cable 234, preferably by the multi-core and extendable cord, or alternatively, the circuit board 123 is preferably placed in the bag 401, linked to by the cable 234. The electrodes 231, placed on the shoulder straps 232, are linked to by the cable 643, preferably a multi-core one, connected to the cable 234, preferably a multi-core one, in the chest belt 147, linking the electrodes 143. The electrodes 143 placed on the chest belt 147, amounting to 2 to 3 electrodes 143, and may be used separately for the single-lead ECG, albeit without shoulder straps 232 in that case. The three-lead ECG may be achieved in connection with the shoulder straps 232 equipped by the electrodes 231. By adding other two electrodes 143 in the chest belt, totally amounting to 5 pcs, and the electrodes 231, preferably attached to the elastic leg belt 147' on the ankles linked to by the cable 643, the 12-lead ECG may be achieved. Alternatively, the electrodes 231' may be placed under the waist. They are depicted as the electrodes 231" in these positions. The electrodes 231' on the leg belt 147' may preferably be linked to with the chest belt 147' by the cable 643' without the shoulder straps 232, preferably by mean of the connectors 644', similarly with the cables 643 by mean of the connectors 644. From that place, the multi-core cable 234 leads the electrodes through the independent cores in the circuit desk 123. The electrodes 231 are placed on the top of shoulder, or closely thereunder, to enable the elastic shoulder straps be pressed towards the skin to achieve good contact, preferably without glue. This is also enabled by the elastic chest belt 147 and the leg belts 147'. The removable and replaceable electrodes 227, preferably the popper ones and/or glued to the belt, and/or the gel ones, enabling good contact with the skin, albeit without gluing them thereto, using the electrodes pushed towards the skin by the elastic belts 147, 147', and the shoulder straps 232, are preferably used instead of the firmly fixed electrodes 231, 143, 231".

Alternatively, the circuit board 123 may be placed on the wrist 645 on the bracelet and connect it by the cables 233 with the shoulder straps 232, further linked to by the cables 643 with the belt 147. The circuit board 123, preferably includes the display 434, preferably a touch screen, to control it thereby. By mean of wireless connection, preferably via Bluetooth, or in case it is created by the mobile phone on the bracelet 236, alternatively by the cable 646, or preferably placed in the mobile phone on the bracelet 236, it is preferably linked to with the multimedia device 600. The principle of chest belt preferably applies with the sliding sensors 209 stored not only for the chest part described in the FIG. 30, but also for the shoulder straps with the fixing shoulder straps 204" pressed by the sensing belts 201". Alternatively, the circuit board 123 is preferably inserted in the bracelet mobile phone 236, placed on the retractable mechanism 664, depicted in the FIG. 28 with the possibility of withdrawal. In such a case, the metallic link to with electronics, secured by spare cable 233, or the extendable cord.

Figure 20:
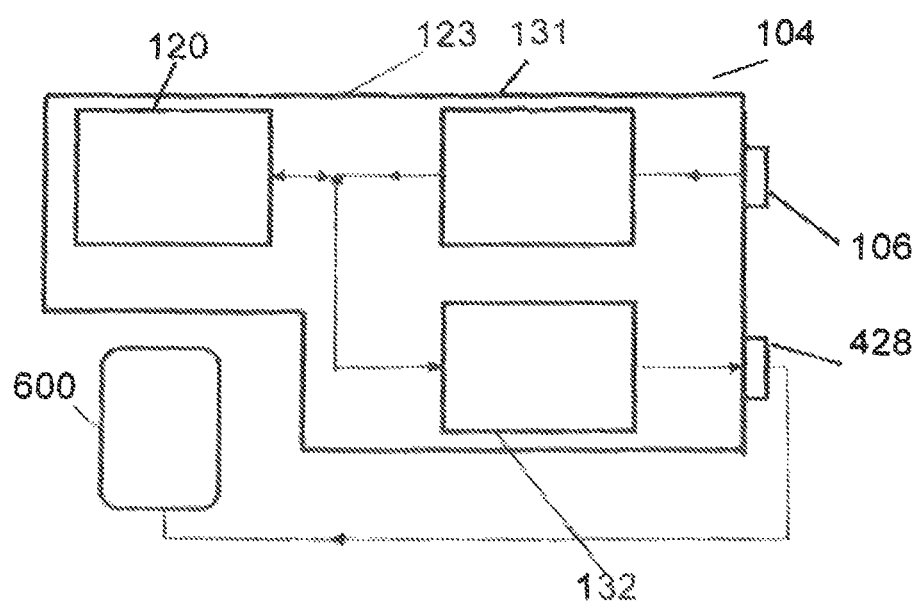
FIG. 20 depicts the block scheme of the circuit board electronics of the auxiliary device with the function of continuous recharging accumulator of the multimedia device via the connector.

FIG. 20 depicts the block scheme of the circuit board 123 electronics of the auxiliary device 104 with the function of continuous recharging accumulator of the multimedia device 600 via the connector 428 without other additional functions. The continuous recharging battery of the multimedia device, via the USB connector 428, enables the continuous and uninterrupted operation of the multimedia device 600 linked to the connector 428 without the necessity to recharge the accumulator of multimedia device by mean of external charger from the network or the notebook, hence to enable the continuous operation of or viewing the given application. Other USB connector 106, reaching the 5V voltage, as a rule, upon connecting it by the cable to the PC, or the charger with the USB connector, enables to charge the accumulator 120 of the bag, and in the same time, through the electronics circuits of the bag, recharge the accumulator of multimedia device. To this end, the accumulator 120, having a substantially larger capacity in comparison with the capacity of accumulator, forming part of the multimedia device 600, applies. The charger 131 of the accumulator 120 with the transformer, being part thereof, transforming the 5V voltage from the USB connector 106, achieved by connecting it to the PC connector, or from the network source, up to the value required to charge the accumulator 120. The voltage transformer 132 is transforming the voltage of accumulator of the multimedia device.

Figure 21:
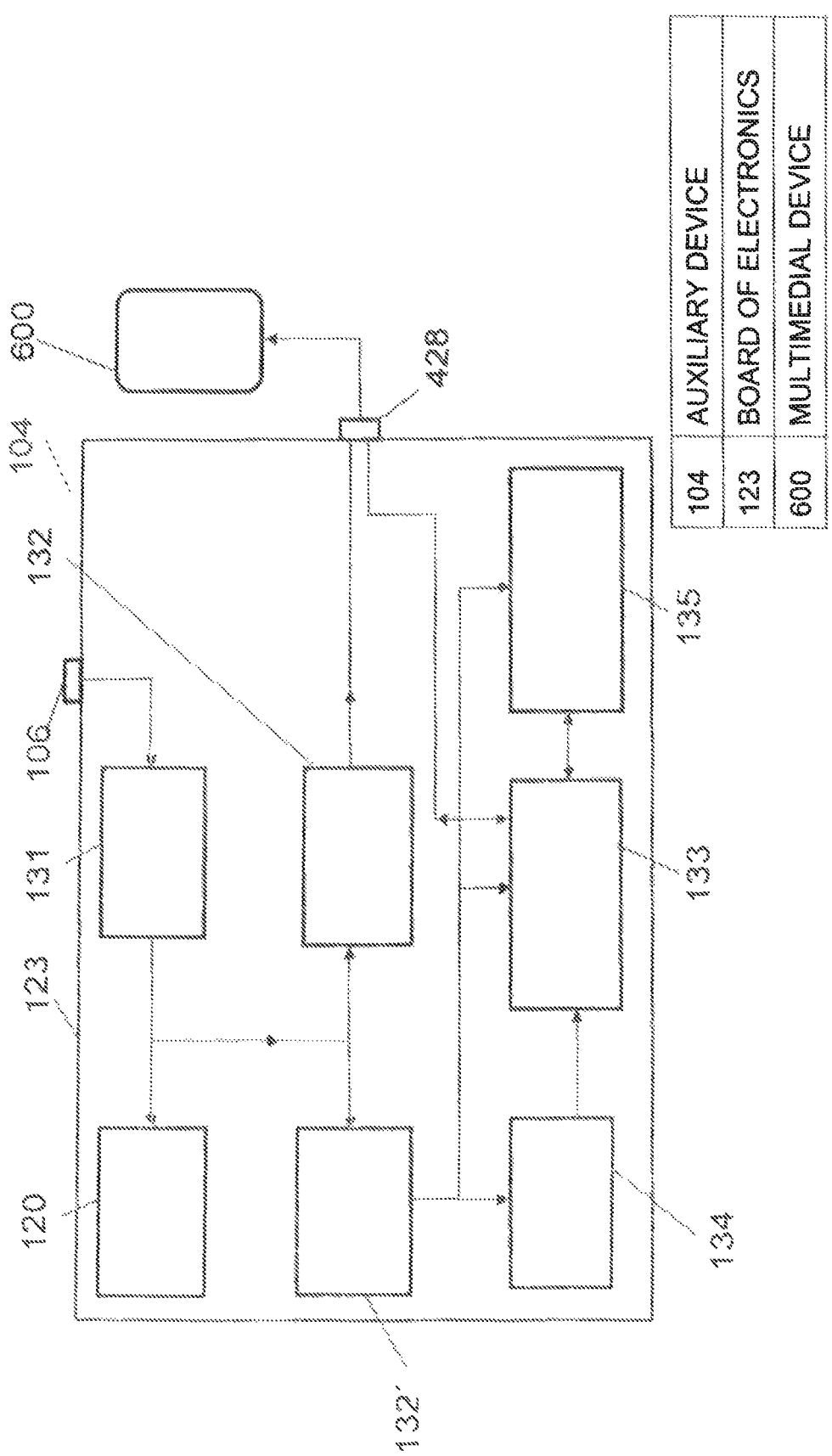
FIG. 21 depicts the block scheme of the electronics of the auxiliary device to enhance the capacity of accumulator of the multimedia device.

FIG. 21 depicts the block scheme of the electronics of the auxiliary device to enhance the capacity of accumulator of the multimedia device 600. In addition thereto, it provides other enhancing functions. The voltage transformer 132' of the accumulator 120 is added to achieve the value required to supply the microprocessor 133, the receiver 134 and the block 135 of BT/BLE/ANT transfers. The receiver 134 of signals transmitted in 5 kHz band may be preferably used to receive signals from the chest belt transmitting data on the heart rate of person using the belt, and similarly the block 135 of transfers BT/BLE/ANT enables the communication with the device transmitting data this way. Thus, the electronics of the bag 401 enables both the two-way wireless communication with the multimedia device 600, and the two-way communication through the connector 428. The data transmitted this way may be assessed by the microprocessor 133, and the results transmitted via the connector 428 to the multimedia device 600, preferably able to view the screen in numeric or graphic form on the display.

Figure 22:
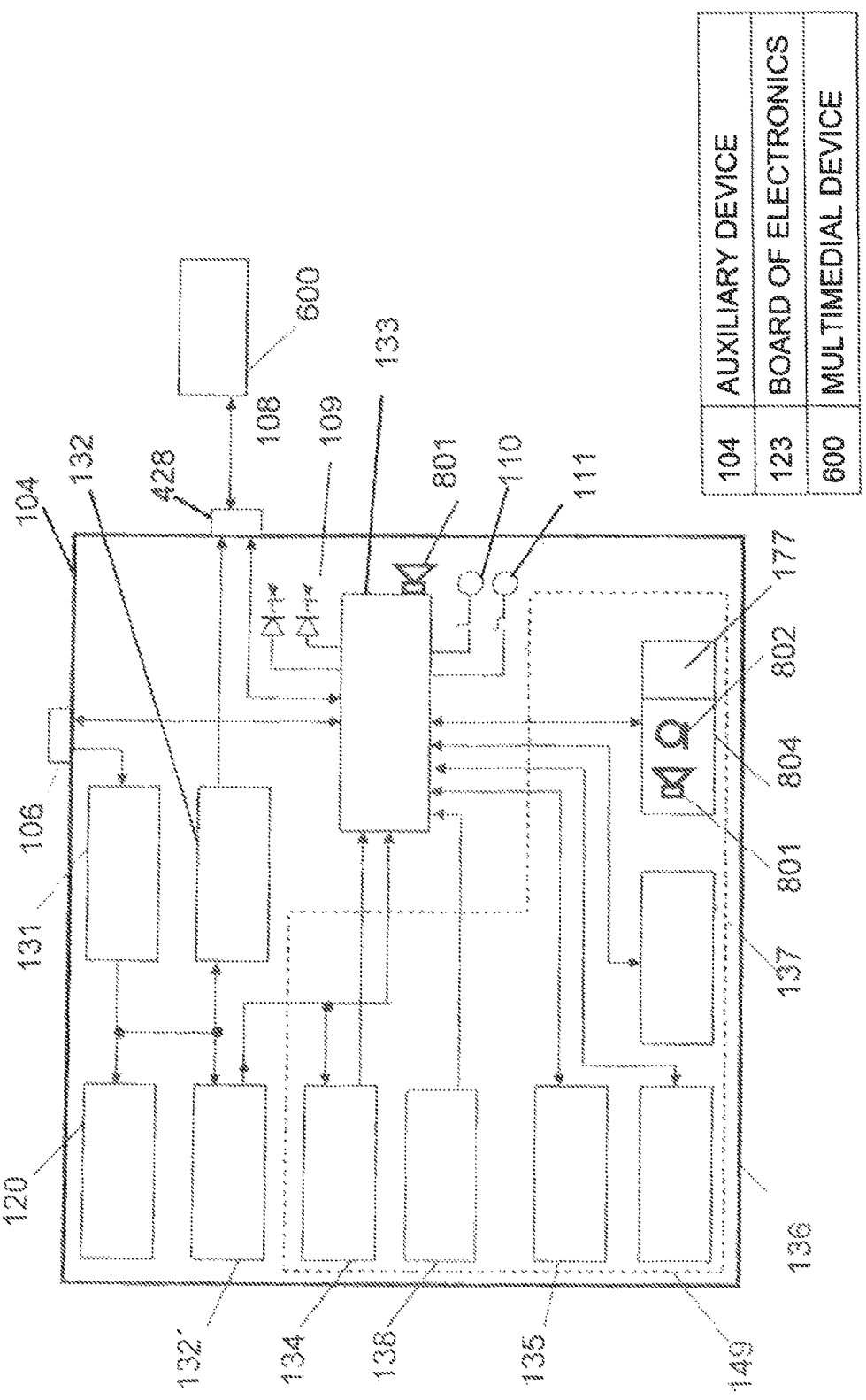
FIG. 22 depicts the block scheme of the electronics of auxiliary device, strengthening the capacity of accumulator of the multimedia device.

FIG. 22 depicts the block scheme of the electronics of auxiliary device, strengthening the capacity of accumulator of the multimedia device 600, it includes the communication block 149, preferably encompassing the receiver 134 of signals in the 5 kHz band, the block 135 of BT/BLE/ANT transfers, the module 136 of RF transfers, the module 137 of Wi-Fi transfers and the module 138 of ZigBee transfers. The receiver 134 of signals in the 5 kHz band, or the block 135 of BT/BLE/ANT transfers may be used, e.g. for the reception of signal from the chest belt processed in the microprocessor 133 and transmitted through the block 135 of BT/BLE/ANT transfers, or the twisted cord, or the cord placed on the reel together with charging 5V voltage in the multimedia device. The possibility to receive and assess data on the heart rate sensed by the chest belts of various producers is an advantage. An important part of the communication block 149 is the block 804 of the GSM communication, enabling the network communication even if the multimedia device was not in active mode. The block 804 contains particularly the SIM card 177 as well as the microphone and the speaker 801 of the voice communication. In addition to the communication block 149, the block scheme depicts the buttons 110, 111 and indicators 108 and 109, preferably the LED ones. These buttons, preferably assigned with the Panic and Reset functions enable to submit the additional instructions of fast activation of mobile phone via the microprocessor 133 such as setting the alarm that is, with the current technology, not feasible to set it in addition fast enough as the application of touch screen of the multimedia device, created preferably by mobile phone, is time consuming for this purpose. The pushed button 110, e.g. with the assigned Panic function, may be assessed by the microprocessor 133 as an emergency request.

To reduce the occurrence of false alarms caused accidentally by pressing the button 110, the indicator 108. e.g. the red LED diode, flashes for few seconds in the adjustable time period. In the same time, the warning acoustic signal is made preferably by the speaker 801. At this time, the alarm mode may be canceled by the button 111, preferably with the Reset function upon expiry of this period of time, unless reset, the microprocessor 133 sends via the connector 428 to the multimedia device 600 the data signal instructing to send preferably the SOS messages prepared in advance and saved to the central prevention desk, or other place prepared to react fast to this emergency call. The communication block 149 is preferably amended by the GSM communicator 463 with the speaker 801 and the microphone 802 to be also preferably used for an emergency calling for the sake of backup by the multimedia device in case of its malfunction. The emergency voice phone communication is preferably pursued, via GSM or other network of the mobile operator, if needed.

Figure 23:
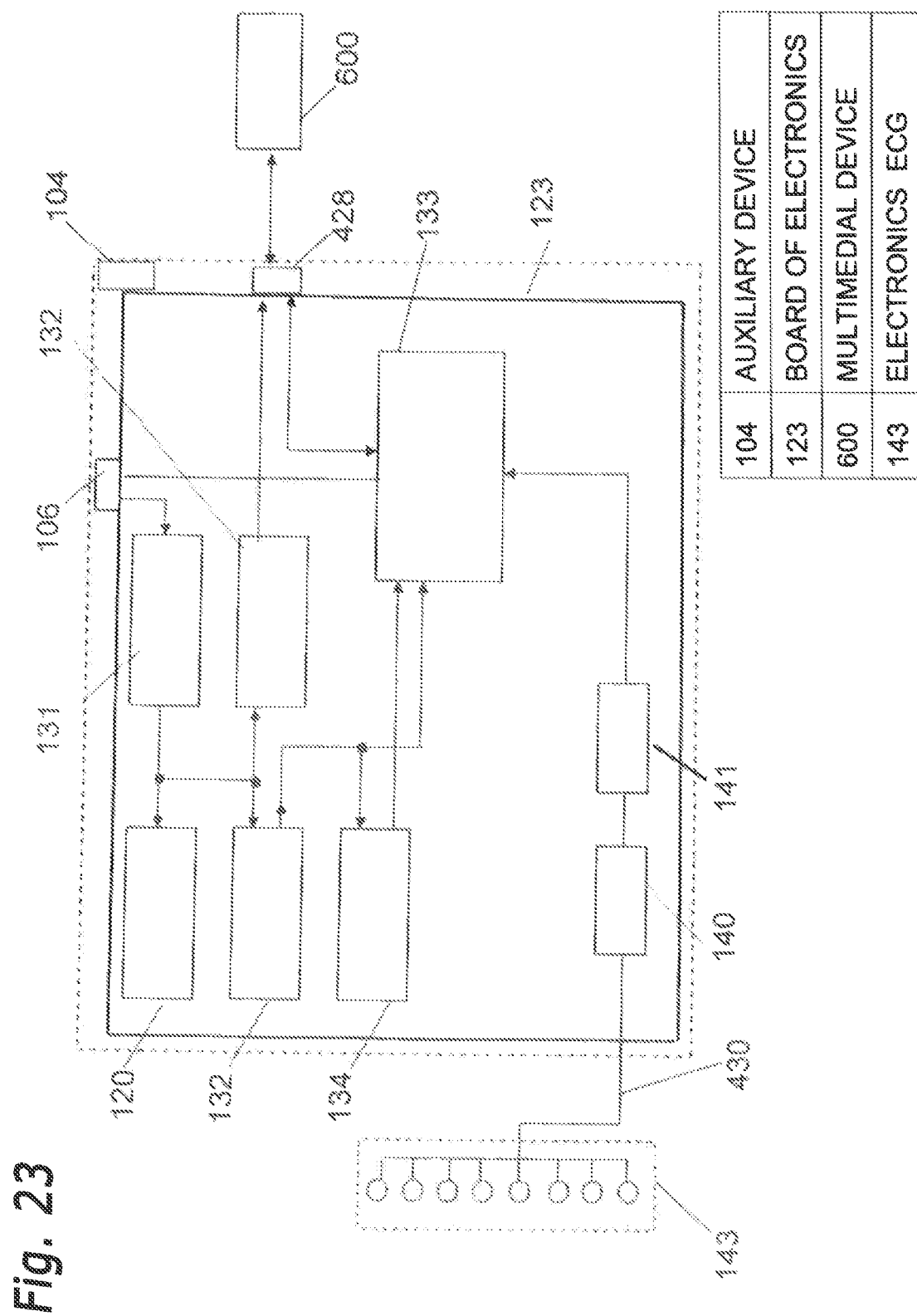
FIG. 23, the block scheme of the auxiliary device, intended to process the analog signals of ECG curve by the module "Front End", placed on the circuit board, and their further processing by the microprocessor upon digitization.

FIG. 23 the block scheme of the auxiliary device, intended to process the analog signals of ECG curve by the module 141 "Front End", placed on the circuit board 123, and their further processing by the microprocessor 133 upon digitization. The ECG leads 430 led from the sensing electrodes 143 are connected to the connector 140, to the module 141 "Front End", to amplify the signals on one hand, filter the interfering signals, and upon digitization, they are digitized by the latter. The signals in the digital form are advanced to the microprocessor 133, whereas, upon being processed, they are led to the connector 428, and further to the multimedia device 600. Moreover, the block scheme depicts the blocks of continuous accumulator charging 120 of the multimedia device 600 through the connector 428.

Figure 24:
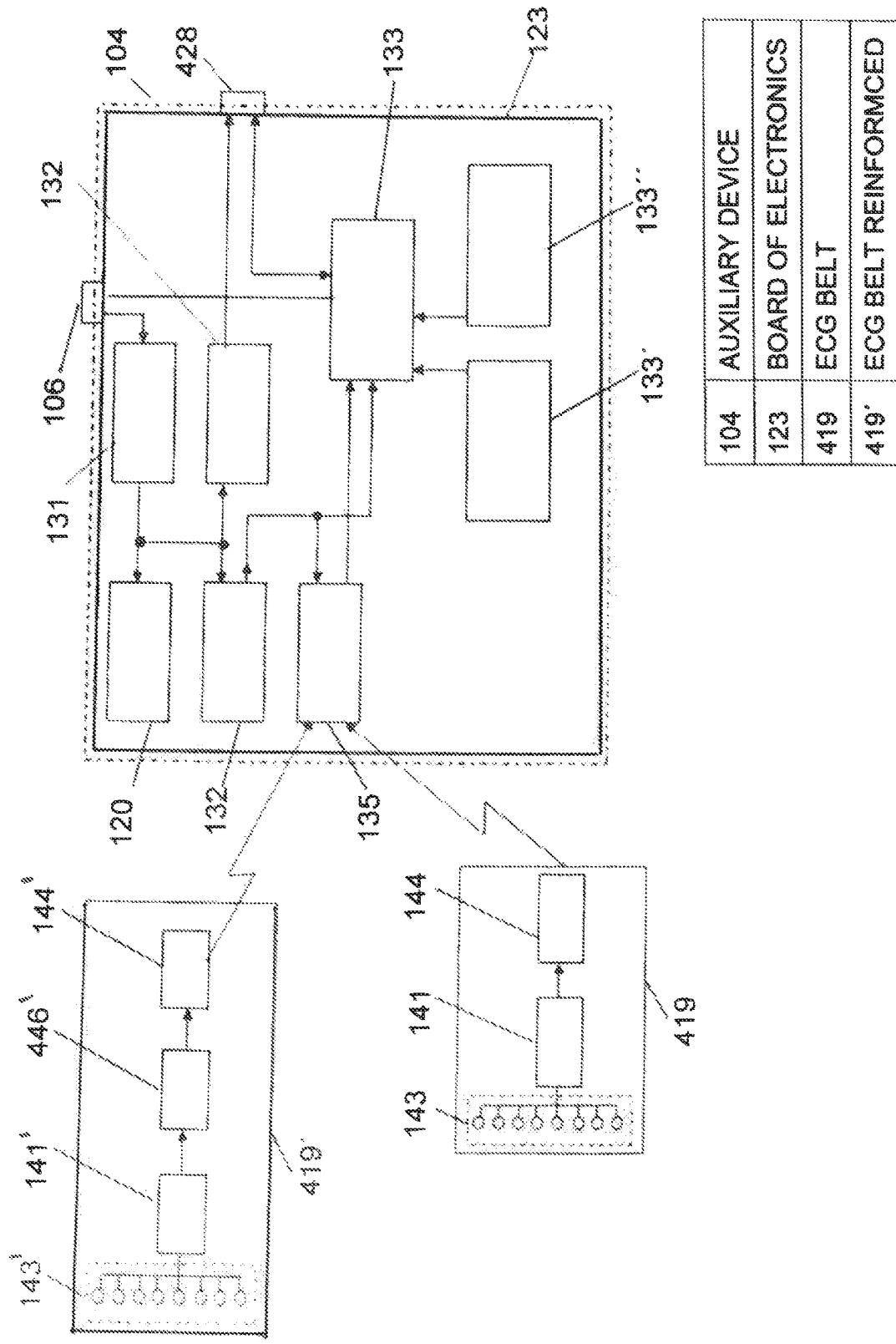
FIG. 24 depicts the block scheme of other option to process the ECG signals by using the auxiliary device forming part of the bag.

FIG. 24 depicts the block scheme of other option to process the ECG signals by using the auxiliary device forming part of the bag. In this case, the electrodes 143 are placed on the ECG belt 419 to enable their connection, and the module 141 "Front End". The ECG sensing signals are amplified and filtered as well as digitized directly on the ECG belt 419. The ECG signals pre-processed in this way are sent wireless through the communication module BT/BLE 144 to the BT/BLE/ANT block 135 of transfers, located in the electronics of the bag to be transmitted therefrom to the microprocessor 133 for further processing the ECG signal. The second microprocessor 133' and other microprocessor 133" may preferably be used to extend the functions. These microprocessors preferably operate with various protocols different from the protocol of multimedia device, bringing about the advantage of working with more databases and programming languages. Other option includes the use of the ECG belt 419, preferably reinforced by the module 446 of the electronics for processing ECG signals completely so that the comprehensive ECG curve in form of data is transmitted to the circuit board 123 to be subject to imaging it. The connection is wire or wireless, preferably via Bluetooth.

Figure 25:
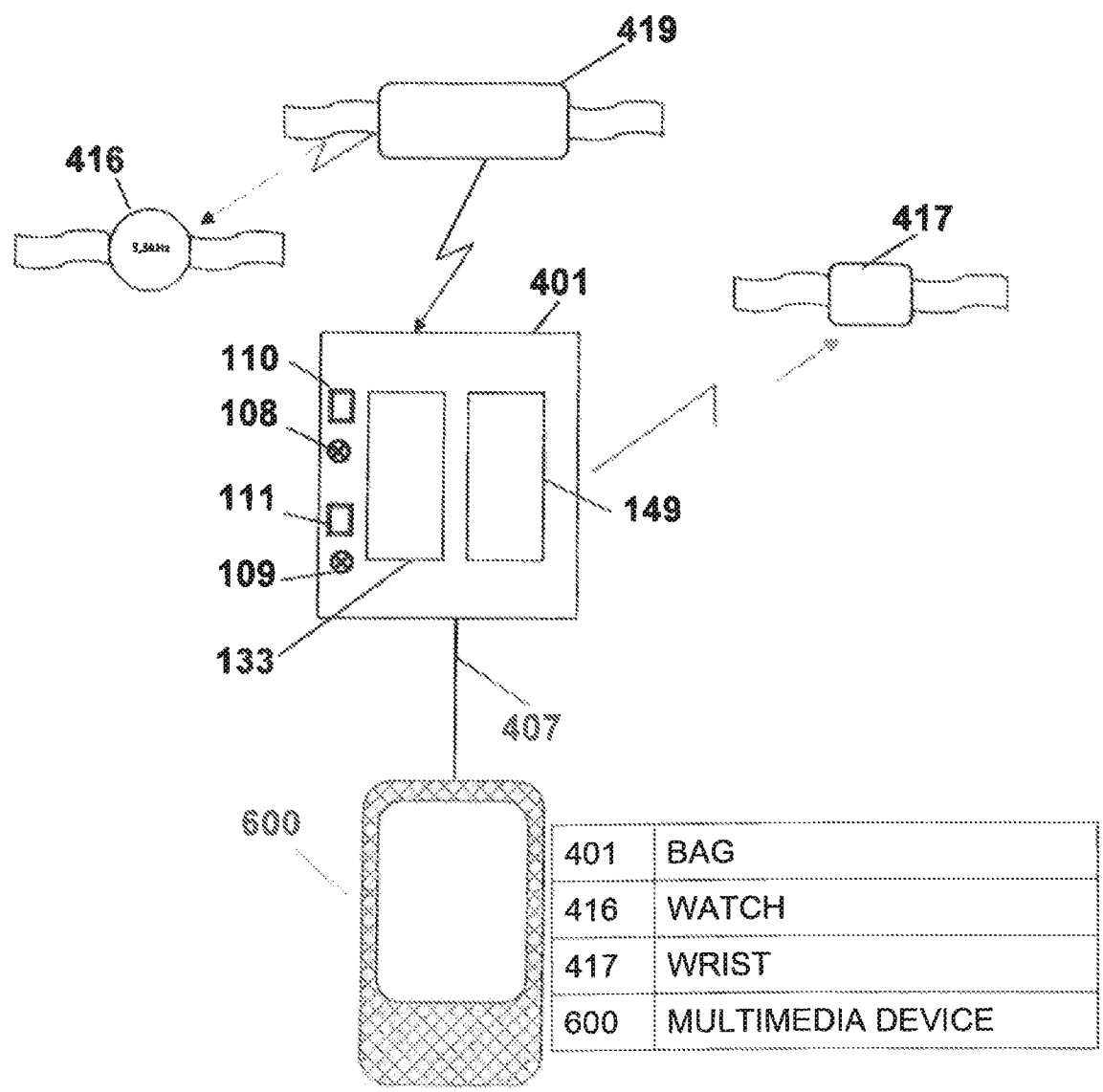
FIG. 25 depicts an example of extending the functions of the multimedia device by mean of the auxiliary device located in the bag to assess the pulse rate.

FIG. 25 depicts an example of extending the functions of the multimedia device 600 by mean of the auxiliary device located in the bag 401 to assess the pulse rate, or ECG by the ECG belt 419 with the possibility of emergency call by pushing the button 110, with the option of resetting the reset button 111. The multimedia device 600 is linked to with the bag 401 by the twisted cord, enabling both the two-way communication, and the continuous charging accumulator of multimedia device. The chest belt may transfer wireless the sensing data to the communication block 149 of the bag 401 by mean of routine communication protocols so that the belts of various producers using various communication protocols may be linked to. Simultaneously, this data are preferably transmitted to the watch 416 with a receiver, preferably operating at 5.5 kHz induction frequency, or 2.4 GHz. The data transmitted to the electronics of the bag 401 is processed by the microprocessor 133, transferred thereafter to the multimedia device 600 to be viewed and controlled, and preferably also in the wrist mobile phone 417 via radio signal, preferably by the BT transfer module, or other suitable communication medium.

Figure 26:
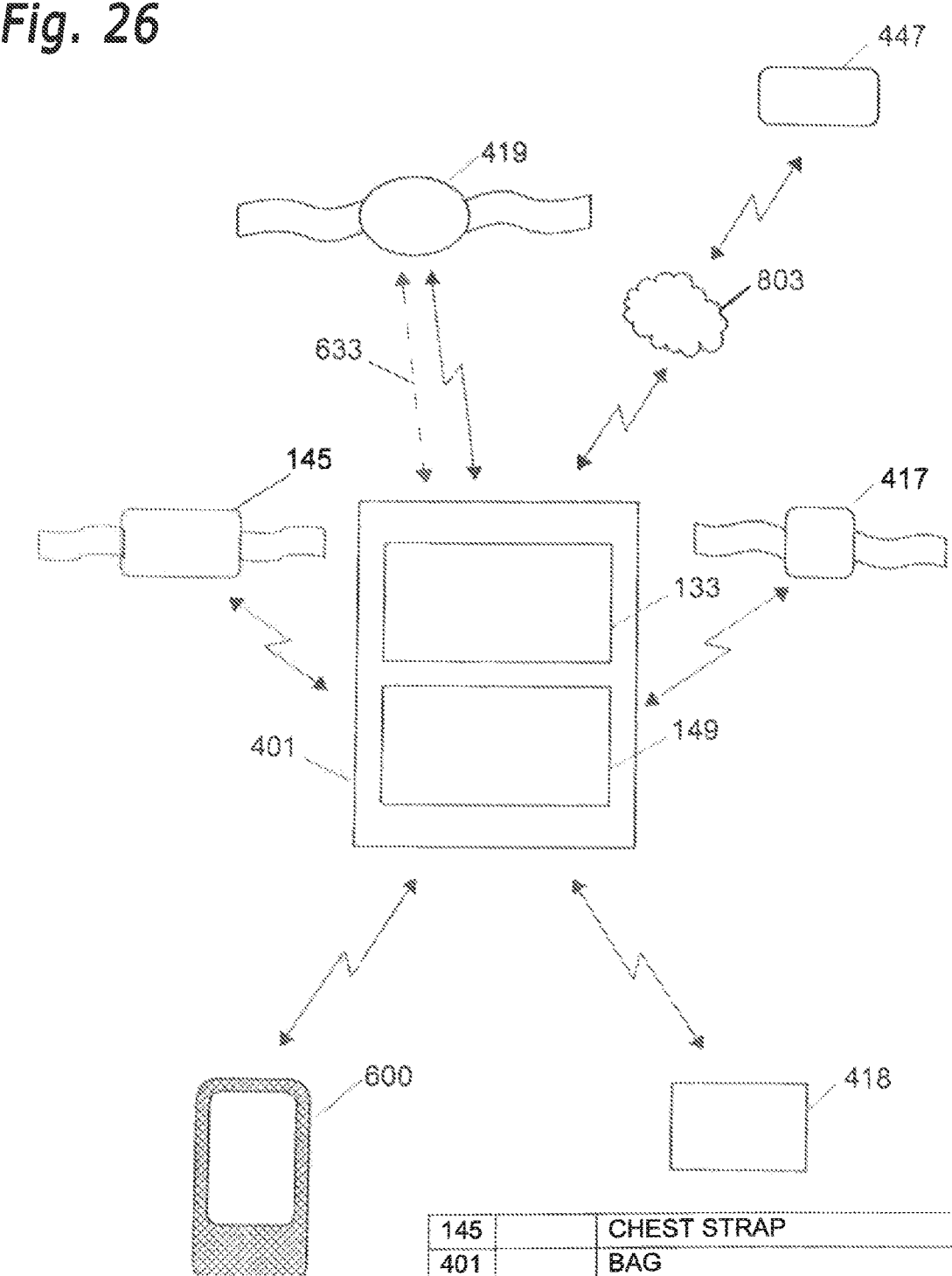
FIG. 26 depicts an example of extending functions of the multimedia device on sensing and assessing ECG with the wireless link to the ECG belt.

FIG. 26 depicts an example of extending functions of the multimedia device 600 on sensing and assessing ECG with the wireless link to the ECG belt 419. The data serving simultaneously to assess the pulse rate are wireless transferred in the electronics circuits of the bag 401, the ECG belt 419, the multimedia device 600, and preferably the PC 418 as well, through the block 149 of transfer, preferably pursuant to the Bluetooth protocol with the multipoint function, or master function. Alternatively, the chest belt 145 transferring data of the pulse rate in 5 kHz band instead of the ECG belt 419 is communicating with the bag 401. Furthermore, the data between the bag 401, and the wrist mobile phone 417, are transferred, preferably by the Bluetooth receiver. The data information is transferred to the surveillance central desk 447, preferably through the network of mobile operator 803 to assess it further. Alternatively, the data are transferred from the ECG belt 419 by mean of the wire circuit 633.

Figure 27:
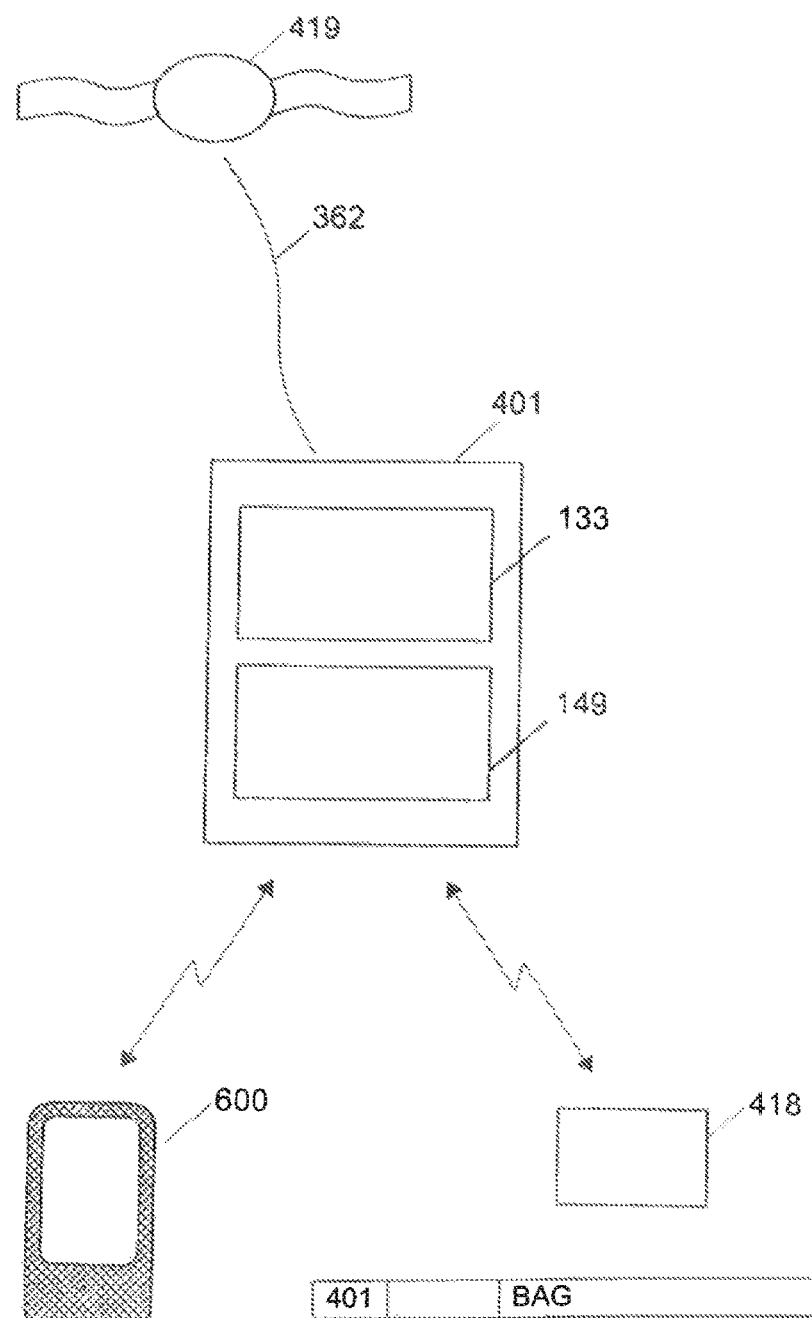
FIG. 27 depicts an example of enhancing the functions of the multimedia device by assessing the ECG signals, transferred from the ECG belt in the electronic circuits of the bag by using the two-core, or four-core cord.

FIG. 27 depicts an example of enhancing the functions of the multimedia device 600 by assessing the ECG signals, transferred from the ECG belt 419 in the electronic circuits of the bag 401 by using the two-core, or four-core cord 362, whereas two wires to transfer data and other two wires may be used for continuous recharging accumulator of the ECG belt 419.

FIG. 28 depicts the bracelet 620 with the eject mechanism 664 for the ejecting attachment of multimedia device 600, adjusted or non-adjusted, preferably with the groove ducts 621, used for moving the sliding sledge 622 thereon, with the position fixed in the limit positions by the small stopping ball 623 pressed on by the spring placed in the bottom part of the sledge 622 snapping shut in the stopping depressions 624 on the surface. The sledges 622 contain the groove 625 with the small rail 626 snapping shut therein; the sledges 622 eject out of the bracelet is ensured by the end stops 627, 627'. The multimedia device 600 is plotted in the ejecting position, while the detail 513 depicts the retracting position. The advantage is the ability to wear the multimedia device in the standby position, on the bracelet, hidden under the shirt, and in case of use to eject it in the visible position. To pull out the multimedia device 600, if required, it shall preferably be adjusted by the ejecting mechanism 664, and it preferably removes the stopper 627, and upon the resistance of the stopping depression on the surface 624' is overcome, the multimedia device 600 may be pulled out from the sledge 622 for free use. Easy insertion in the groove 625 preferably enables the extended lead-in 637. The described design of the ejecting mechanism 664, preferably adjusted for pulling out the multimedia device 600, serves just an example so that it may be executed by other appropriate mechanism.

FIG. 29 depicts the side view of the ejecting mechanism 664 with the placement of the multimedia device 600 made visible, may be non-adjusted, preferably on the movable sledges 622 with them mounted to the rear cover of the multimedia device 600, additionally mechanically interconnected by a suitable joint such as screw, glue, dry zip or alike. The multimedia device 600' adjusted already at the factory is preferably used so that the back cover contains grooves and the rear wall adjusted this way assumes the function and replaces the moveable sledges 622. The advantage is the possibility of inserting the multimedia device 600 into the sleeve of coat or jacket fast, thereby hiding it when not used and pulling it out fast, if required.

The multimedia device 600 preferably wears the attached auxiliary device 104, depicted in the previous figures, with the circuit board 123, the additional accumulator 129 removable through the door 466 upon extrusion by the spring 422, preferably mounted on the rear cover 101 of non-adjusted multimedia device consisting of the mobile phone.

Figure 30:
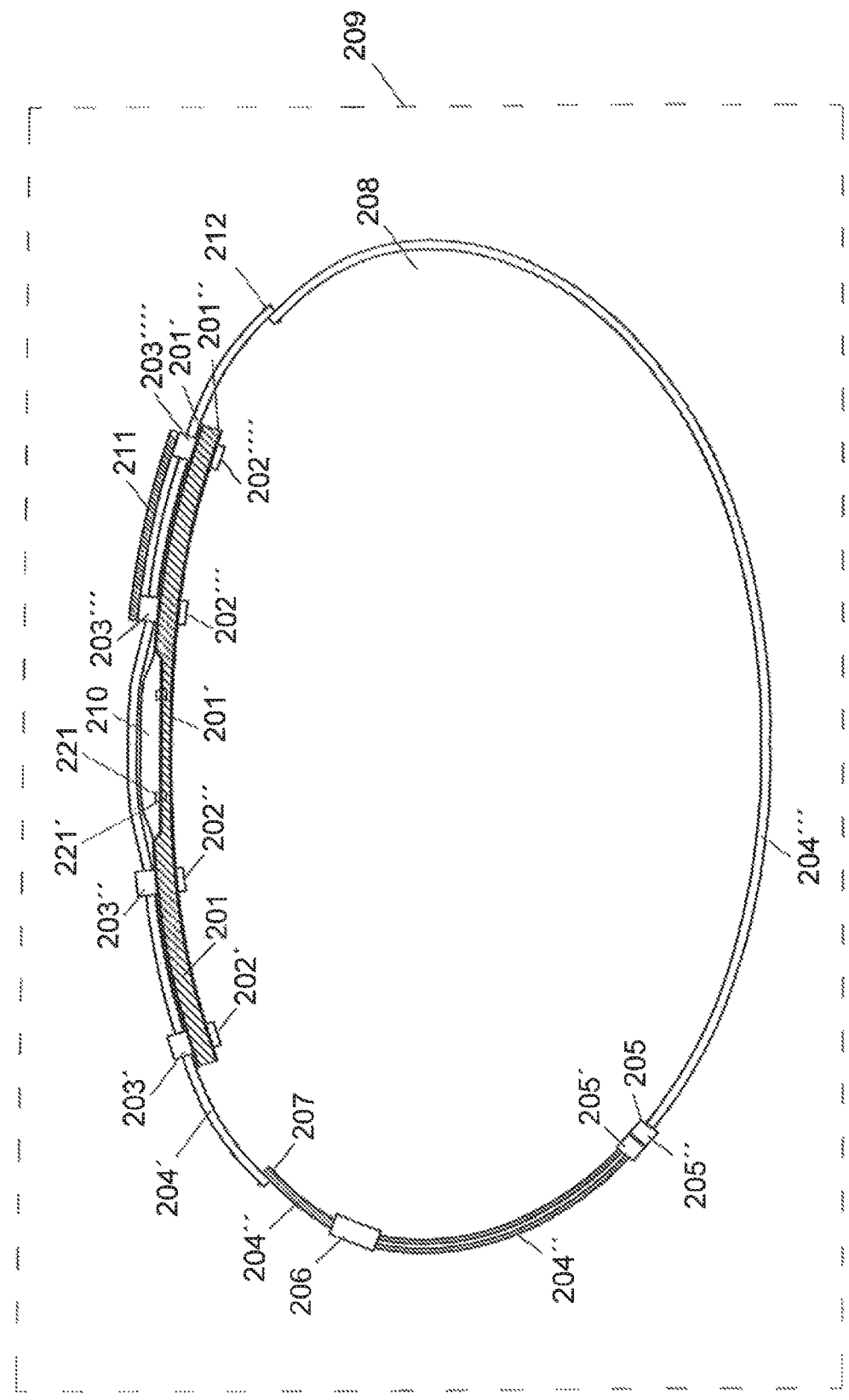
FIG. 30 depicts the belt for continuous sensing the electric activity of the heart muscle, showing itself in the form of biomedical signals of very low voltage travelling on the surface of the body which can be sensed by using the electrodes placed in the appropriate points of the body of examined person.

FIG. 30 depicts the belt intended for continuous sensing the electric activity of the heart muscle, showing itself in the form of biomedical signals of very low voltage travelling on the surface of the body which can be sensed by using the electrodes placed in the appropriate points of the body of examined person, preferably for the heart rate and/or ECG measuring. In terms of achieving reliable contact of the electrodes sensing the biomedical signals, particularly for the long-term continuous sensing, it is important to minimize the occurrence of interfering signals caused by moving the contacts on the surface of body. Due to this, the position of contacts on the surface of body should not be changed due to the movement of the person in the sensing session. This problem is dealt with by the chest belt 209, with the sensors stored to allow the sliding movement, arranged according to FIG. 30, by replacing the commonly used belt with the electrodes, firmly attached to the fixing fastening belt, by mean of the system of two belts sliding mutually at each other's surface that is composed of the sensing belt 201 with the electrodes 202, and the fixing belt 204 surrounding the entire chest of the monitored person which presses the sensor belt 201, and thus its electrodes 202 towards the body surface 208 of the monitored person either. The individual electrodes are marked by the reference code of the electrodes 202, amended by the apostrophe ('), i.e. the electrode 202' up to the electrode 202''''. The flexible fixing belt is composed of three parts, particularly the part of the fixing belt 204', the part of the fixing belt 204", and the part of the fixing belt 204'''. The first side of the sensing belt 201' with the electrodes 202 must have a surface that best adheres to the body 208 to avoid sliding the sensing belt 201 on the body, thus ensure the invariable reliable contact of the electrodes 202 with the body 208. The other way around, the other side of the sensing strip 201", with the loops 203, must have a sliding surface, preferably made of Teflon, to achieve the slightest rubbing between its surface and the surface of the sliding part of the fixing belt 204'. With regard to the first side of the sensing belt 201' and the side 201", there are different requirements offered in this way. Due to this, they are preferably covered by the layers of different materials, and/or the sensing belt 201 is composed of two connecting layers of different materials. Similarly to the contact surface, the electrodes 202 may be composed of the electric power conductive material which are glued to, steamed to the sensing belt 20, and/or created directly on the first side of the sensing belt 201' made of the electric power non-conductive material. The conductive and non-conductive plastic which, in the same time, may form the first side of the sensing belt 201', with the conductive regions made of the electric power conductive plastic, having the function of the electrodes, may preferably be combined. The sliding part of the fixing belt 204' is preferably made of the material with a low friction coefficient, e.g. Teflon, or it is coated by such a material, and it is connected to the sensing belt 201 by mean of several loops 203. The individual loops are marked by the reference code of the loops 203, with apostrophes such as the loop 203', or the loop 203'''', firmly connected to the sensing belt 201, with them passed through on the sliding part of the fixing belt 204 thus creating the mutually slightly sliding connection. In the movement of the fixing belt 204, moving on the surface of the sensing belt, due to impact of the movement of the body, it slides on the sensing belt 201 so that the position of the sensing belt 201 against the body 208 remains unchanged. The sliding part of the fixing belt 204' is connected with the part of the fixing belt 204" by the expandable clip 207, with that clip being expanded only at the passing part of the fixing belt 204' through on the loops 203, e.g. during the repair, and thus being constantly joined to when using the belt 204'. The other end of the part of the fixing belt 204' is connected to the fixed connection 212 to the part of the fixing belt 204". Other two parts of the fixing belt 204" and 204''' are made of a flexible material, preferably the rubber-textile strip. The total length of the fixing belt 204, and thus also the pressure imposed to push the sensing belt 201 towards the body 208, can be set up in the mentioned example by the movable clasp 206, enabling to adjust and fix the length of the loop created by passing the fixing belt 204" through on the clasp 206. The connection/disconnection of the part of the fixing belt 204" of the part of the fixing belt 204''' is ensured by the two-piece disconnecting conjunction 205. Two or more contact surfaces, mechanically connected to the sensing belt 201, are electrically connected with one, or more sensors, e.g. the sensor 210, and the sensor 211, processing the biomedical signals sensed by the electrodes 202 for further processing. The electrodes 202 may be positioned on the sensing belt 201, or directly in the sensing belt 201, or the sliding part of the fixing belt 204'. There are possible different ways of using the electrodes 202 and the combination of connecting them to the sensors. In the depicted configuration, the electrodes 202' and 202''' are connected to the sensor 211, and the electrodes 202" and 202'''' are connected to the sensor 210.

Figure 31:
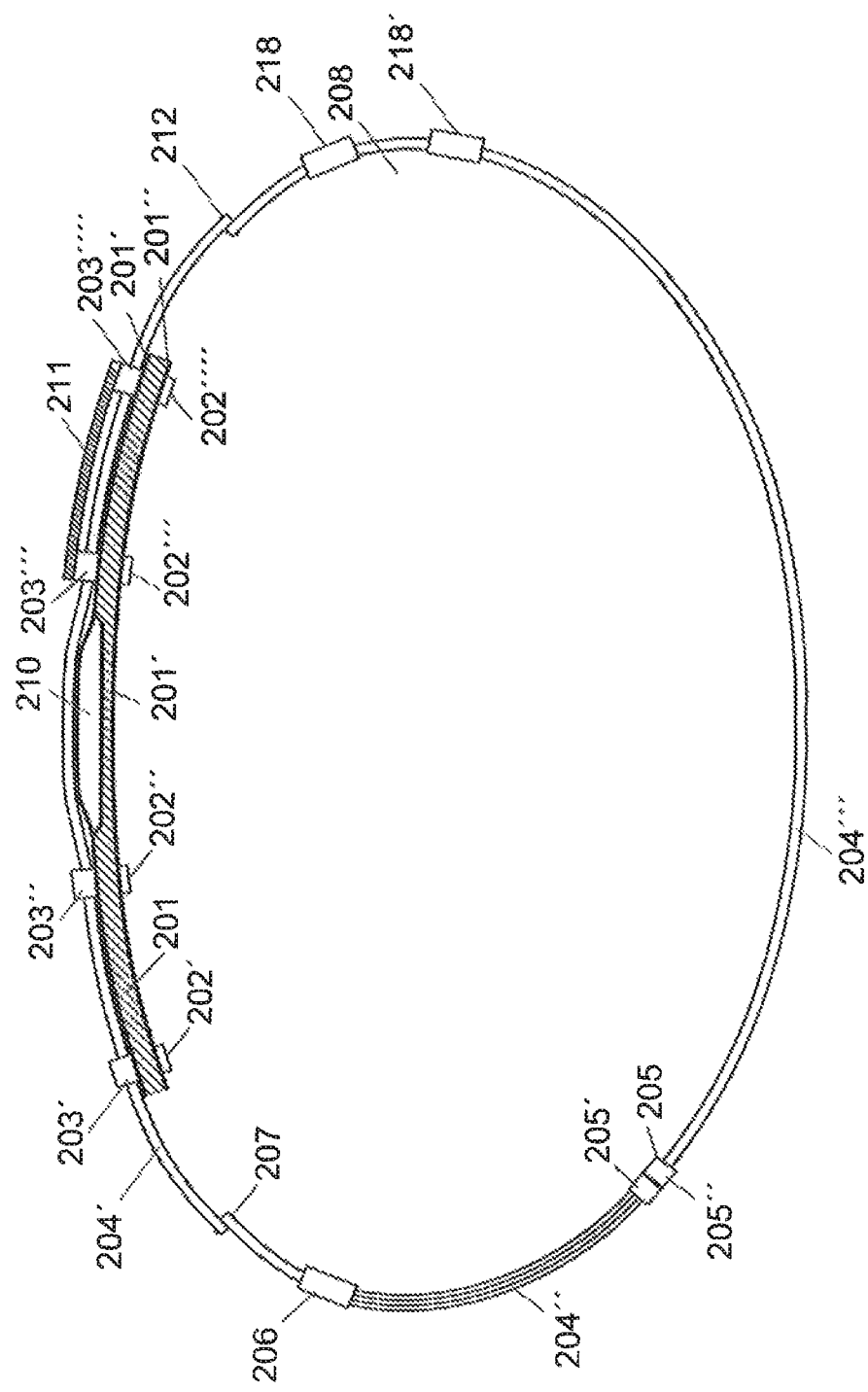
FIG. 31 depicts the option of the previous configuration of the chest belt with the sensors stored so as to allow the sliding movement, with the sensor integrated in the sensing belt.

FIG. 31 depicts the option of the previous configuration of the chest belt with the sensors stored so as to allow the sliding movement, with the sensor 210 integrated in the sensing belt 201, with the surface shaped so as to enable the sliding part of the fixing belt 204' to slide perfectly on the surface of the sensing belt 201. The auxiliary device 218 composed of the easy replaceable accumulator to supply the sensors 210 and 211 with power, or recharge their accumulators respectively, extends the operation time of the depicted sensors 210 and 211 without charging, or replacing the built-in accumulators of sensors. With advantage could be used other auxiliary device 218' too, which may contain the electronic circuits, e.g. for further processing of the sensed biomedical signals.

Figure 32:
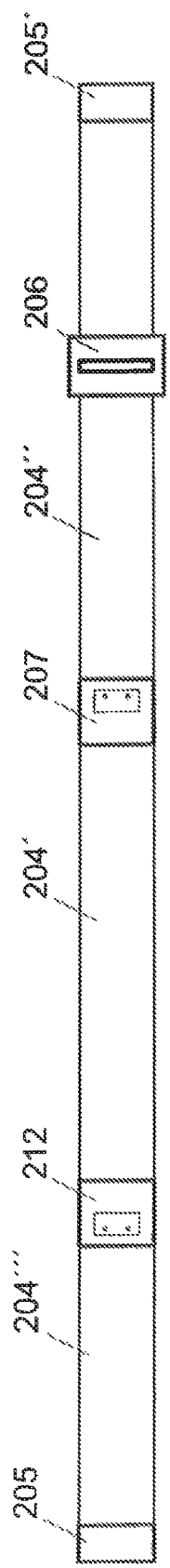
FIG. 32 depicts the disconnected fixing belt in the straighten form.

FIG. 32 depicts the disconnected fixing belt 204 in the straighten form, the conjunction 205 is disengaged, the part of conjunction 205', connected with the part of the fixing belt 204", is detached from the conjunction part 205" connected with the part of the fixing belt 204". The sliding buckle 206 is intended for setting the length of the fixing belt 204, and thus the pressure used to push the electrodes 202 to the body 208 through the sensing belt 201 either. Other depicted parts were described in FIG. 30.

Figure 33:
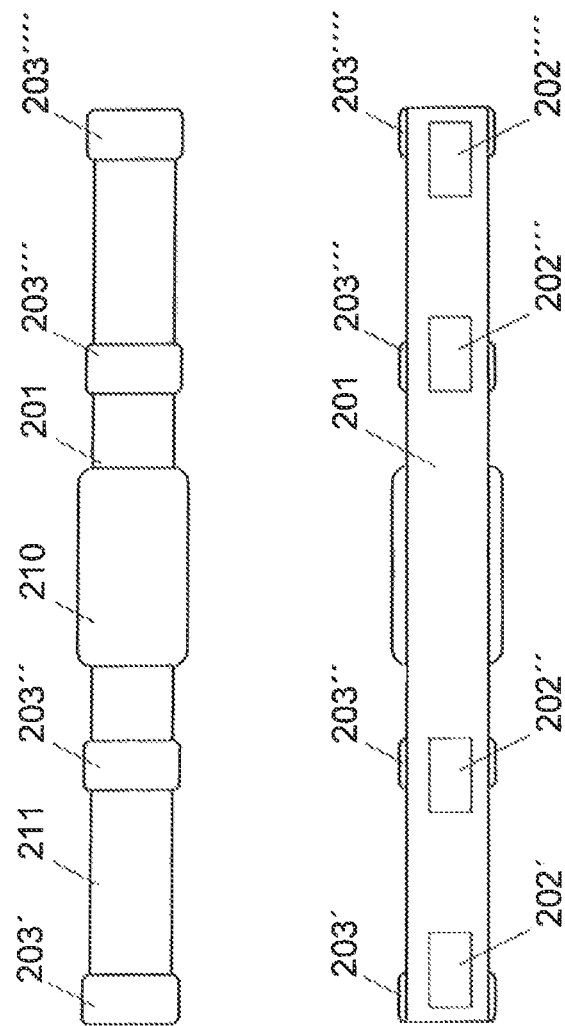
FIG. 33 depicts a view of the sensing belt from the side of loops and the side of the electrodes.

FIG. 33 depicts a view of the sensing belt 201 from the side of loops 203 and the side of the electrodes 202. In this case, the sensor 210 is placed on the sensing belt 201.

Figure 34:
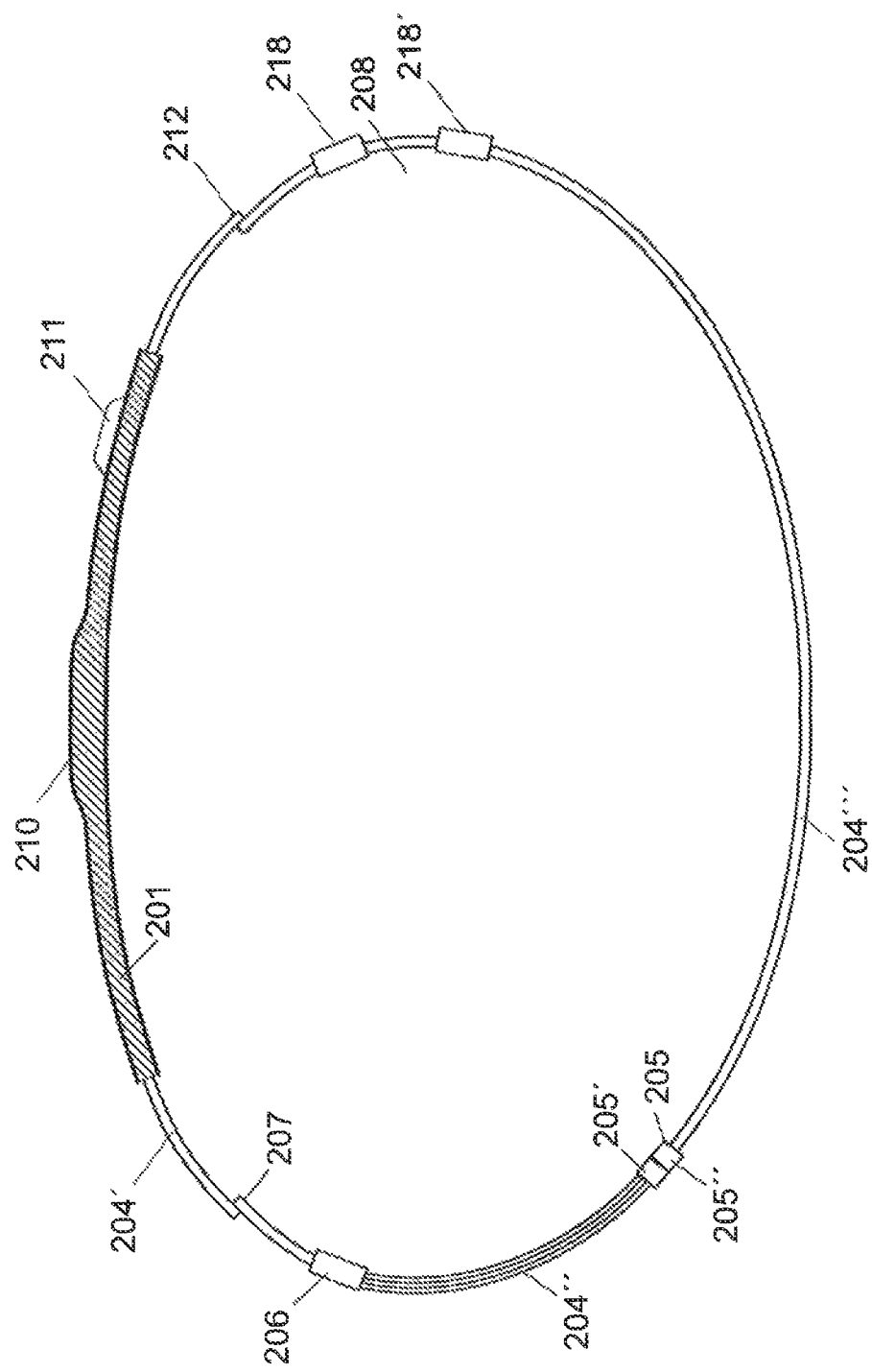
FIG. 34 depicts a simplified chest belt with the sensors, used in combination with the shoulder straps so as the chest belts.

FIG. 34 depicts a simplified chest belt with the sensors 210 and 211, preferably able to be used in combination with the shoulder straps 232, 204' so as the chest belts depicted in FIGS. 1 to 33.

Figure 35:
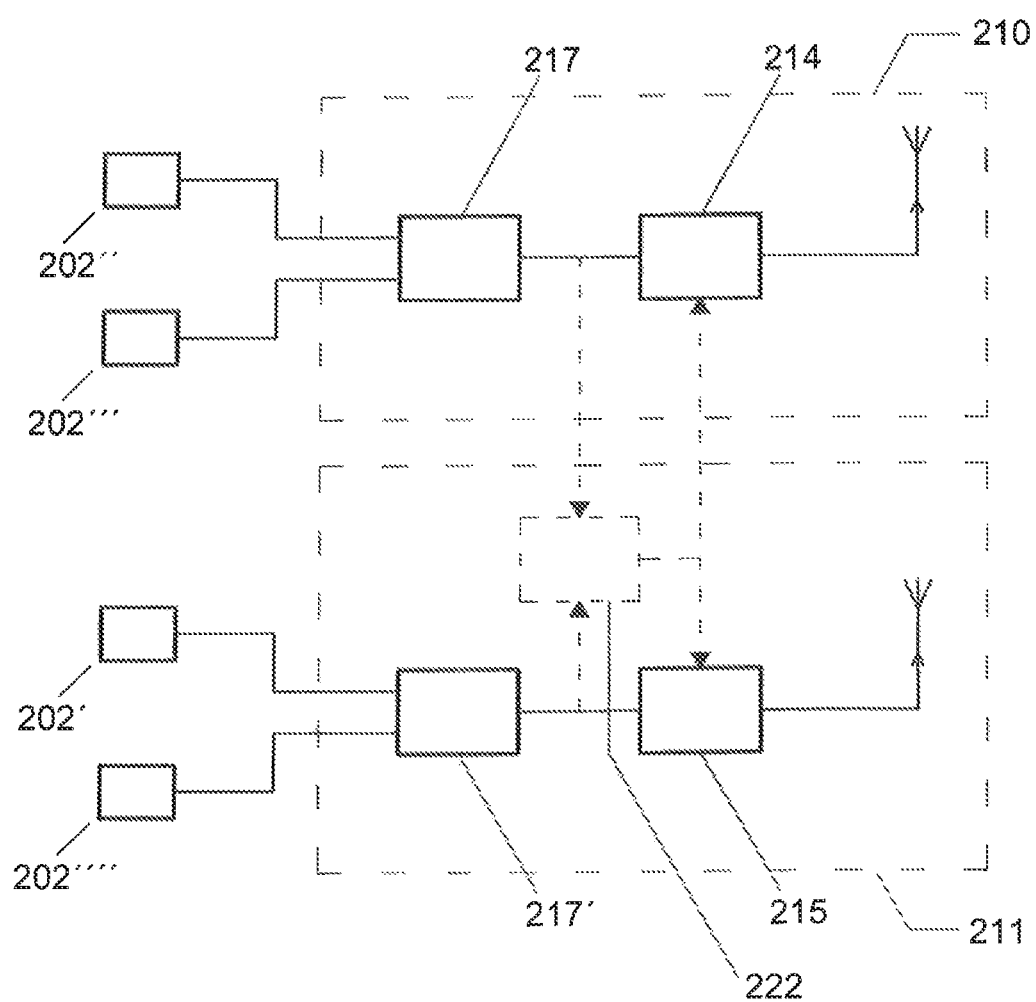
FIG. 35 depicts the block scheme of using the electrodes, and sensors of the chest belt.

FIG. 35 depicts the block scheme of using the electrodes 202, and sensors 210 and 211 of the chest belt 209, preferably with the sensors stored so as to allow the sliding movement, with an example of execution shown in FIG. 32. The mentioned configuration enables the assessment of bio-signals sensed by the selected electrodes, placed on the chest belt with two independent sensors stored so as to allow the sliding movement, and the results sent wireless by two or more independent transmission paths preferably by using different transmission protocols. The pair of the electrodes comprised of the electrode 202" and the electrode 202" is connected to the sensor 217 inputs placed in the independent sensor 210, together with the transmitter 214, preferably operating in 5 kHz band. The electrodes 202' and 202'" are connected to the inputs of other sensor 217', located in the second independent sensor 210, together with the transmitter 215, preferably operating in 2.4 GHz band, preferably by use of the transmission Bluetooth protocol. The connection enables the sensors 217 and 217' to assess simultaneously the bio-signals, sensed by the pair of the electrodes, formed by the electrode 202" and the electrode 202, and via the second pair, consisting of the electrode 202' and the electrode 202" ", with the results transmitted for further use as a data by mean of the transmitter 214, and in the same time, through the transmitter 215. The jamming resistance may preferably be improved by the control unit 222 which compares the signals at the outputs of the sensors 217 and 217', and at the moment of assessing the failure, it disables the transmitter 214, or the transmitter 214'. The jamming resistance may similarly be improved by using the receiver 214', operating in 5 kHz band, and simultaneously the receiver 215', operating in 2.4 GHz band, with their output data being assessed by the control unit 222'.

Figure 36:
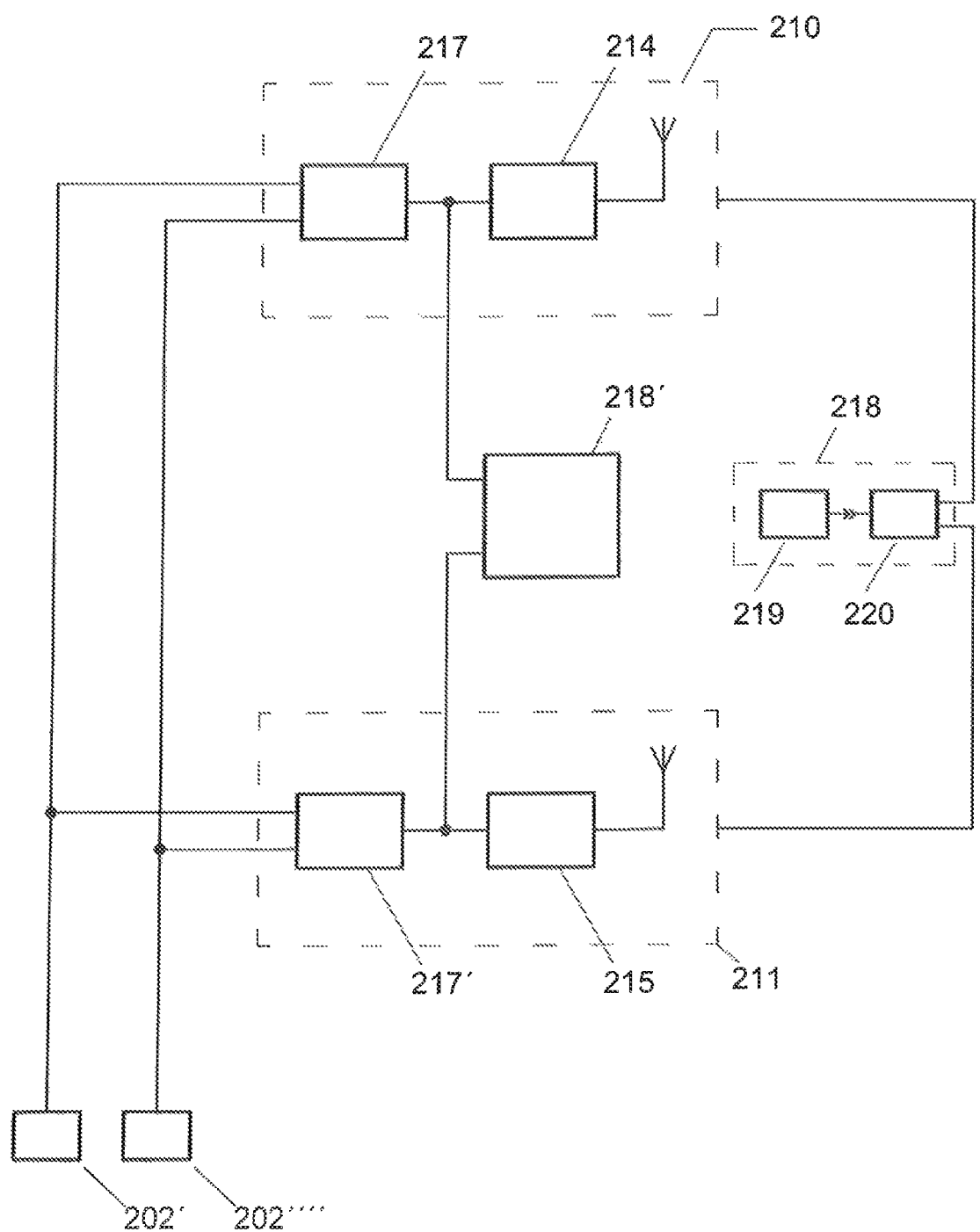
FIG. 36 depicts the block scheme option just using the electrodes, connected with the parallel linked inputs of the sensor and the sensor.

FIG. 36 depicts the block scheme option just using the electrodes 202' and 202" ", connected with the parallel linked inputs of the sensor 210 and the sensor 211. In this case, the sensors 210 and 211 evaluate bio-signals sensed by one pair of electrodes 202' and 202"", assessed by the various sensors 217 and 217', with the results transmitted by two independent transmitters 214 and 215. Furthermore, the auxiliary device 218, containing the readily replaceable accumulator 219, with the electronics 220, to supply the auxiliary devices by the power from the backup accumulator 219, is also depicted. Other auxiliary device 218', may also preferably be used, with the electronic circuits, e.g. for further processing of the sensed biomedical signals.

Figure 37:
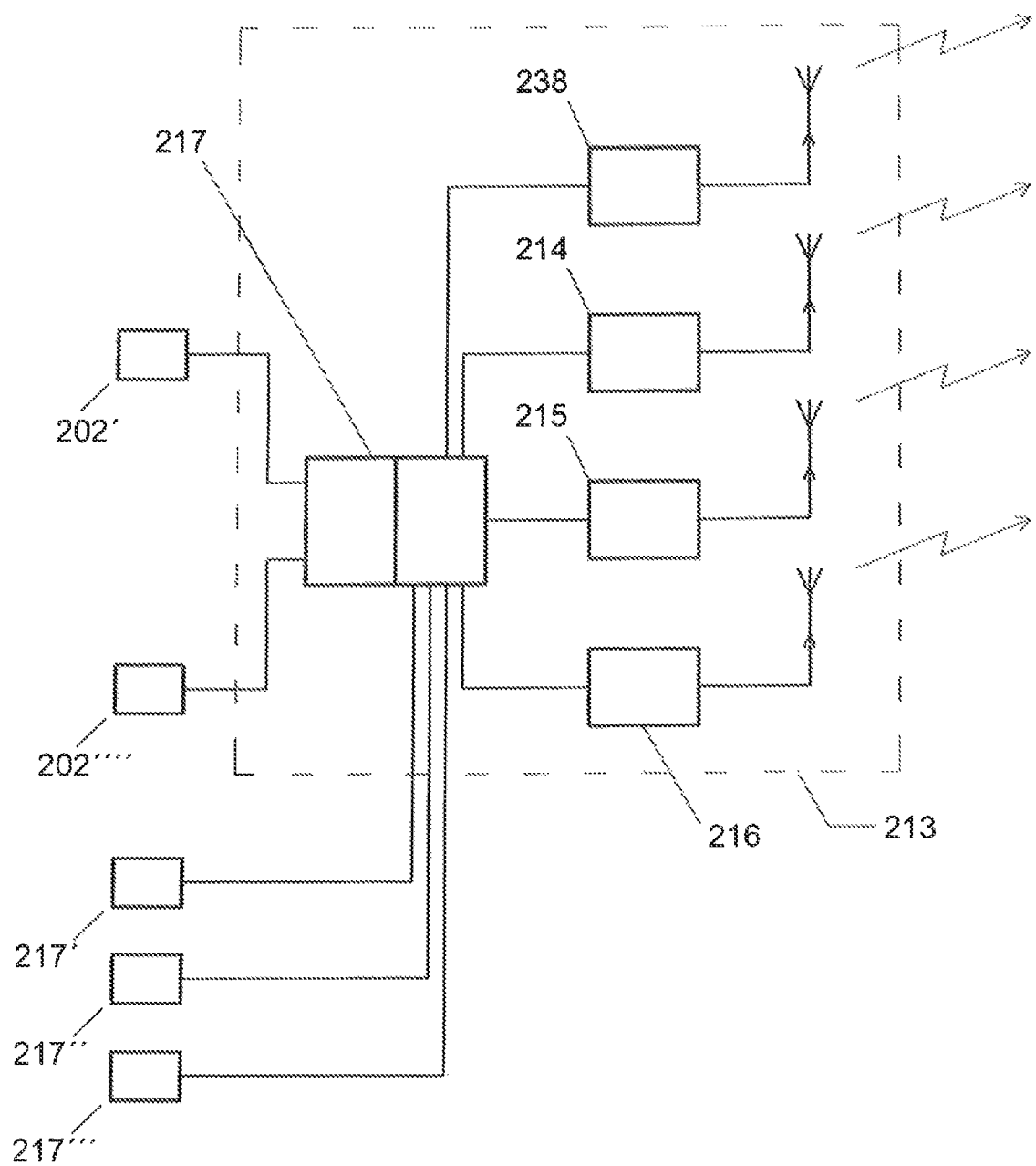
FIG. 37 depicts the block scheme of the probe with communication block.

FIG. 37 depicts the block scheme of the probe 213 with communication block, preferably formed by the transmitter 214, operating in 5 kHz band, and the transmitter 215, operating in 2.4 GHz band, using the Bluetooth transmission protocol and the transmitter 216, operating in 2.4 GHz band using the ANT transmission protocol, and preferably other transmitters 238, operating in other protocols. The signals sensed by the pair of electrodes formed by the electrode 202' and the electrode 202" " of the sensor 217.

Figure 38A:
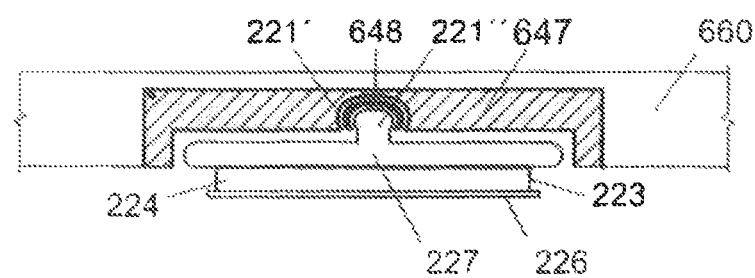
FIG. 38A depicts the electrodes, the snap fastener or the gel ones.
Figure 38B:
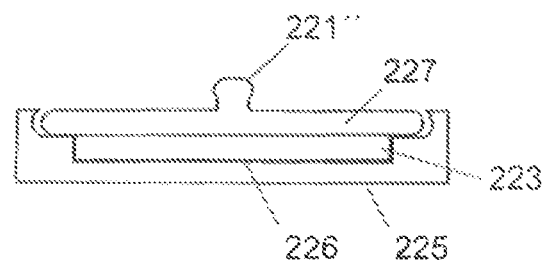
FIG. 38B depicts electrode pulled on in the plastic cartridge
Figure 38C:
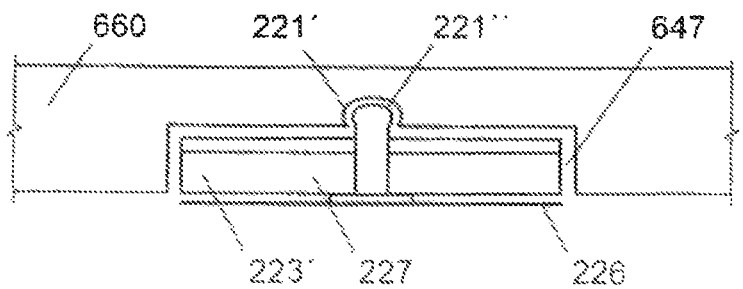
FIG. 38C depicts the electrodes with the protusion mounted directly on the gel material

FIG. 38A depicts the electrodes 227, preferably the popper, or the gel ones. Their conductive connection to the sensors ensures the connection of the popper sleeve 221"— the popper-thorn 221' system that can be dismantled, with the thorn 221' located on the side of the electrode, and the sleeve 221" on the side of the pushing element 660, preferably of the chest or leg belt, shoulder straps, elastic clothes, or harness, particularly in its conductive part 653 linked to the input of heart rate detector, or eventually the circuit board. The sleeve is preferably filled by the female part of the clip 648. The electrodes 227 are designed to have the contact surface 224 intended for contact with the human skin. The contact is improved by the conductive gel layer 223 laid on this surface. In the configuration of FIG. 38A-38C, there is the gel layer covered by the sensing cover foil 226. By pressing the finger on the foil, the electrode snaps in the counter connector, a sleeve in the belt 147.

Thereafter, the cover foil 226 is removed and the electrode is put in the required position on the body of sensing person.

FIG. 38B depicts electrode pulled on in the plastic cartridge 225 to be removed upon the snapping the electrode on the belt. This configuration prevents the gel leakage from the contact surface at the handling and snapping the electrode in the belt.

FIG. 38C depicts the electrodes 227 with the thorn 221' mounted directly on the gel material 223 and fit in the sleeve 647 of the chest belt, preferably made of the elastic material. An easy removal capability and the high conductivity of the gel 223, and in the same time, the adhesion to the skin, hold in the belt on the body in the position without slippery, is an advantage.

Figure 39:
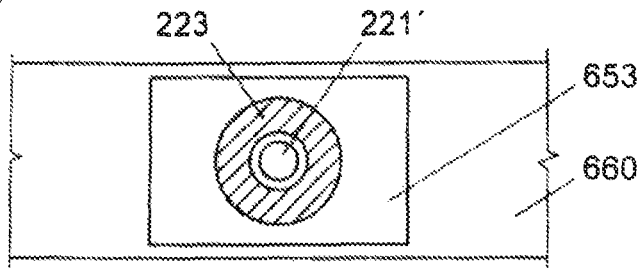

FIG. 39 depicts the portion of the pushing element 660 to enable that the electrodes 202 are pulled on, and it provides the conductive connection to the body of the sensing person and the heart rate, or the ECG detector. The sensing portion of the electrode, i.e. the popper-thorn 221', connected with the skin, is preferably a metallic one and preferably laid by the conductive gel 223. In the pushing element, there is a conductive part of the pushing element connected with the electrode that creates the electrode fixing mechanism 654 described in the following figures.

Figure 40:
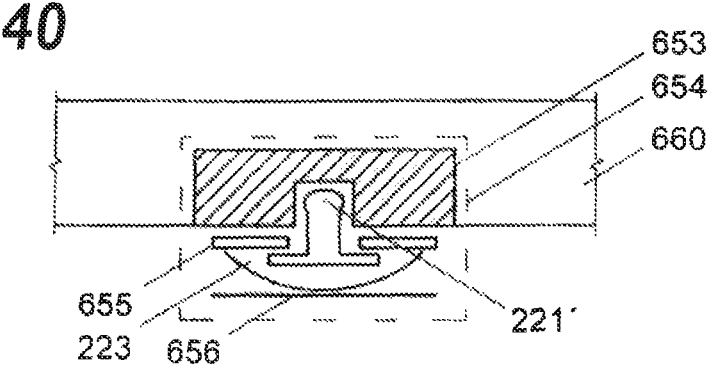
FIG. 40 depicts the fixing mechanism of the electrode, composed of the conductive element of the pushing element.

FIG. 40 depicts the fixing mechanism 654 of the electrode, composed of the conductive element of the pushing element 660, with the sleeve of conductive element 658 latched by the popper-thorn 221'. Before setting the electrode to the sensing position on the body, the plastic cover 656 of gel of the electrode is removed.

The plastic foil 655 of the electrode includes the composition with the popper-thorn 221, and it may preferably be furnished by an adhesive layer to secure stronger connection with the pushing element 660.

Figure 41:
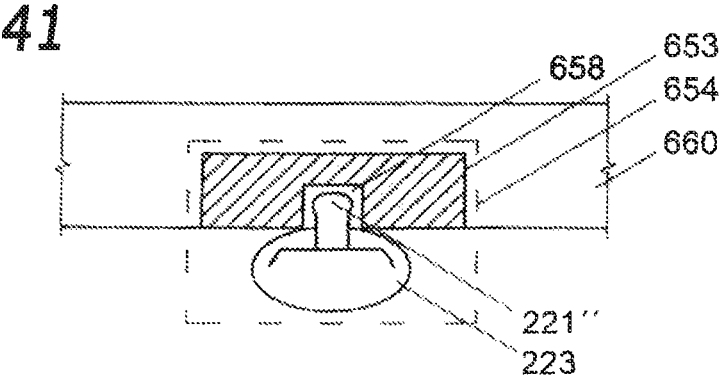
FIG. 41 depicts the execution of the gel electrode in the identical configuration of the fixing mechanism of the electrode.

FIG. 41 depicts the execution of the gel electrode in the identical configuration of the fixing mechanism 654 of the electrode. In this case, the plastic foil 655 of the electrode is omitted and the entire body of the electrode is created by the popper-thorn 221 with the contact body formed by the gel 223.

Figure 42:
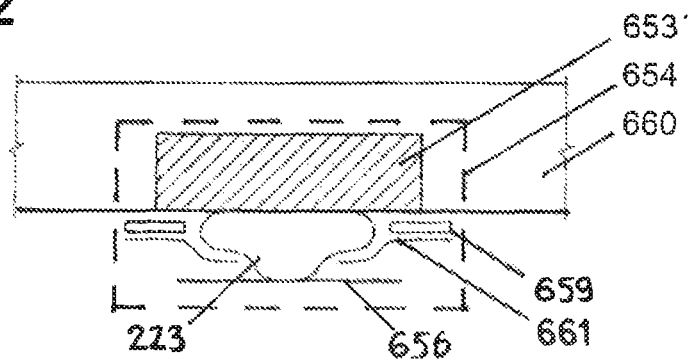
FIG. 42 depicts the solution of the electrode fixing mechanism of the covering shaped annulus with its adhesive layer.

FIG. 42 depicts the solution of the electrode fixing mechanism of the covering shaped annulus 661, with its adhesive layer 659, revealed upon the electrode unpacking from the package and the cover foil removing, adheres to the conductive portion 653' of the pushing element. Upon removing the plastic cap 656' of the electrodes, and pressing the electrode by the pushing element towards the body, the gel 223 leaks from beneath the covering shaped ring 661 to ensure the conductive contact link.

The invention claimed is:

1. Auxiliary device for multimedia, health and sport equipment comprising a chest belt sensor for sensing heart signals from a body of a monitored person, said chest belt sensor having a sensing belt, electrodes disposed on the sensing belt, and a sensor, for sensing of heart signals for heart rate and/or electrocardiogram (ECG) the electrodes and chest belt sensor being placed on the chest of monitored person from the front; and the auxiliary device further comprises a fixing belt, which encircles the chest of monitored person over the sensing belt and presses the sensing belt and thus the electrodes to the chest where the fixing belt has a sliding part, wherein the sensing belt and the fixing belt are a system of two belts adapted for mutually sliding against each other freely, so that the position of sensing belt against the body remains unchanged during motions of the person, and while the sliding part of the fixing belt slides over the sensing belt.

2. Auxiliary device for multimedia, health and sport equipment according to claim 1 further comprising at least one of:
- loops connected to the sensing belt through which the sliding part of the fixing belt passes thereby creating a mutually sliding connection;
- a two-piece disconnecting conjunction for connection or disconnection of a part of the fixing belt with or from a part of the fixing belt;
- a movable clasp for adjusting of the length of the fixing belt;
- an expandable clip for connection of the sliding part of the fixing belt with the part of the fixing belt;
- a fixed connection for connection of a part of the fixing belt to the part of the fixing belt;
- at least one of the electrodes includes a protrusion on one side of the electrode.

3. Auxiliary device for multimedia, health and sport equipment according claim 1 comprising at least two independent transmission paths for heart signals.

4. Auxiliary device for multimedia, health and sport equipment according claim 3, wherein the at least two independent transmission paths are for heart signals from the body of the monitored person through the electrodes, a first path is from electrodes pressed against the chest of the monitored person through the sensor and the second path is from electrodes pressed against the chest of the monitored person through a different sensor where each path has an independent transmitter.

5. Auxiliary device for multimedia, health and sport equipment according claim 1, wherein the sensing belt comprises a pushing element connected to the electrodes, at least one of the electrodes includes a protrusion on a side of the electrode, a conducting gel layer, and a cover foil, and the connection between electrodes and pushing element is achieved by the protrusion, conducting gel layer and cover foil.

6. Auxiliary device for multimedia, health and sport equipment according claim 5, wherein the at least one electrode covered by conductive gel is placed in a plastic cartridge, to be removed upon snapping the at least one electrode on the sensing belt.

7. Auxiliary device for multimedia, health and sport equipment according claim 1, wherein the sensing belt comprises a pushing element including a fixing mechanism having a sleeve made of conductive material disposed on the pushing element, at least one of the electrodes includes a protrusion on the side of the electrode and the conducting gel layer, the at least one electrode is fastened to the pushing element by means of the fixing mechanism formed by the sleeve of the pushing element into which the protrusion of the at least one electrode fits in and the other side of the at least one electrode is furnished by the conducting gel, which is advantageously uncovered by removing of a plastic cover, just before applying the at least one electrode on a skin of the monitored person.

8. Auxiliary device for multimedia, health and sport equipment according claim 7, wherein the fixing mechanism further includes an adhesive layer in the shape of a ring, and the protrusion is fixed to a conductive part of the sleeve by the adhesive layer prior to being removed, the plastic cover creates space for the conducting gel, which, after removal of the plastic cover of the electrode and by pressing the conducting gel by pushing element to the body of the monitored person, gets into contact with the skin on one side of the protrusion and with conductive part of pushing element on the other side of the protrusion.

9. Auxiliary device for multimedia, health and sport equipment according claim 1, wherein the electrodes are placed on the sensing belt for sensing heart signals for at least one ECG from one lead from the monitored person, which can be extended by adding additional electrodes for chest, legs and arms.

* * * * *